US012655216B2

(12) United States Patent
Lamba et al.

(10) Patent No.: US 12,655,216 B2
(45) Date of Patent: Jun. 16, 2026

(54) CD33 ANTIBODIES

(71) Applicant: University of Florida Research Foundation, Incorporated, Gainesville, FL (US)

(72) Inventors: Jatinder Kaur Lamba, Gainesville, FL (US); Mohammed Olusoji Gbadamosi, Gainesville, FL (US); Vivek Shastri, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 592 days.

(21) Appl. No.: 18/026,195

(22) PCT Filed: Sep. 15, 2021

(86) PCT No.: PCT/US2021/050449
§ 371 (c)(1),
(2) Date: Mar. 14, 2023

(87) PCT Pub. No.: WO2022/060832
PCT Pub. Date: Mar. 24, 2022

(65) Prior Publication Data
US 2023/0365676 A1     Nov. 16, 2023

Related U.S. Application Data

(60) Provisional application No. 63/078,686, filed on Sep. 15, 2020.

(51) Int. Cl.
*C07K 16/28* (2006.01)
*A61K 47/68* (2017.01)
*A61P 35/02* (2006.01)

(52) U.S. Cl.
CPC ...... *C07K 16/2803* (2013.01); *A61K 47/6803* (2017.08); *A61K 47/6849* (2017.08); *A61K 47/6867* (2017.08); *A61P 35/02* (2018.01); *C07K 2317/24* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 9,066,928 | B1 | 6/2015 | Estus et al. |
| 10,239,941 | B2 | 3/2019 | Westerman et al. |
| 2017/0002074 | A1 | 1/2017 | Yu et al. |
| 2019/0203299 | A1 | 7/2019 | Lamba et al. |

FOREIGN PATENT DOCUMENTS

| | | |
|---|---|---|
| WO | WO 2014/074942 A1 | 5/2014 |
| WO | WO 2015/036583 A2 | 3/2015 |
| WO | WO 2015/089344 A1 | 6/2015 |
| WO | WO 2015/089344 A9 | 6/2015 |

OTHER PUBLICATIONS

Extended European Search Report mailed Dec. 3, 2019 in connection with EP Patent Application No. 17779829.5.
International Search Report and Written Opinion mailed Jul. 20, 2017 in connection with PCT/US2017/026369.
International Preliminary Report on Patentability mailed Oct. 18, 2018 in connection with PCT/US2017/026369.
Invitation to Pay Additional Fees for Application No. PCT/US2021/050449, mailed Nov. 24, 2021.
International Search Report and Written Opinion for Application No. PCT/US2021/050449, mailed Jan. 31, 2022.
International Preliminary Report on Patentability for Application No. PCT/US2021/050449, mailed Mar. 30, 2023.
Gbadamosi et al., Novel CD33 antibodies unravel localization, biology and therapeutic implications of CD33 isoforms. Blood. 2019; 134 (Supplement_1): 908. https://doi.org/10.1182/blood-2019-122596.
Lamba et al., Clinical Significance of CD33 Non-Synonymous Single Nucleotide Polymorphisms (SNPs) in Pediatric Patients with Acute Myeloid Leukemia Treated with Gemtuzumab Ozogamicin-Containing Chemotherapy. Blood. Nov. 18, 2011;118(21):3489. doi: https://doi.org/10.1182/blood.V118.21.3489.3489.
Lamba et al., Coding polymorphisms in CD33 and response to gemtuzumab ozogamicin in pediatric patients with AML: a pilot study. Leukemia. Feb. 2009;23(2):402-4. doi: 10.1038/leu.2008.185. Epub Jul. 10, 2008.
Lourdusamy et al., Identification of cis-regulatory variation influencing protein abundance levels in human plasma. Hum Mol Genet. Aug. 15, 2012;21(16):3719-26. Epub May 16, 2012.
Mortland et al., Clinical significance of CD33 non-synonymous single nucleotide polymorphism (SNPs) in pediatric patients with acute myeloid leukemia treated with gemtuzumab-ozogamicin-containing chemotherapy. Clin Cancer Res. Mar. 15, 2013;19(6):1620-7. doi: 10.1158/1078-0432.CCR-12-3115.

(Continued)

*Primary Examiner* — Phuong Huynh

(57)     ABSTRACT

Aspects of the disclosure relate to compositions and methods for treating certain (e.g., CD33-positive) cancers. In some aspects, the disclosure provides antibodies that specifically bind to CD33 protein variants that lack an IgV domain. In some aspects, the disclosure provides adaptable cell engagers (ACEs) and recombinant proteins (e.g., BiTEs) comprising an anti-CD33 antibody of the disclosure and an anti-CD3 antibody. In some embodiments, the disclosure provides methods of treating cancer by administering the antibodies, ACEs, or recombinant proteins (e.g., BiTEs) to a subject in need thereof.

6 Claims, 33 Drawing Sheets

Specification includes a Sequence Listing.

(56) References Cited

OTHER PUBLICATIONS

Sherva et al., Genome-wide association study of the rate of cognitive decline in Alzheimer's disease. Alzheimers Dement. Author manuscript; available in PMC Jan. 1, 2015. Published in final edited form as: Alzheimers Dement. Jan. 2014; 10(1): 10.1016/j.jalz.2013.01.008. Published online Mar. 25, 2013. doi: 10.1016/j.jalz.2013.01.008.

Sleegers et al., A 22-single nucleotide polymorphism Alzheimer's disease risk score correlates with family history, onset age, and cerebrospinal fluid $A\beta_{42}$. Alzheimers Dement. 2015;1452-60. doi: http://dx.doi.org/10.1016/j.jalz.2015.02.013.

Walker et al., Association of CD33 polymorphism rs3865444 with Alzheimer's disease pathology and CD33 expression in human cerebral cortex. Neurobiol Aging. Author manuscript; available in PMC Feb. 1, 2016. Published in final edited form as: Neurobiol Aging. Feb. 2015; 36(2): 571-582. Published online Oct. 2, 2014. doi: 10.1016/j.neurobiolaging.2014.09.023.

Walter et al., Acute myeloid leukemia stem cells and CD33-targeted immunotherapy. Blood. Jun. 28, 2012;119(26):6198-208. doi: 10.1182/blood-2011-11-325050. Epub Jan. 27, 2012. Review.

EP 17779829.5, Dec. 3, 2019, Extended European Search Report.

PCT/US2017/026369, Jul. 20, 2017, International Search Report and Written Opinion.

PCT/US2017/026369, Oct. 18, 2018, International Preliminary Report on Patentability.

PCT/US2021/050449, Nov. 24, 2021, Invitation to Pay Additional Fees.

PCT/US2021/050449, Jan. 31, 2022, International Search Report and Written Opinion.

PCT/US2021/050449, Mar. 30, 2023, International Preliminary Report on Patentability.

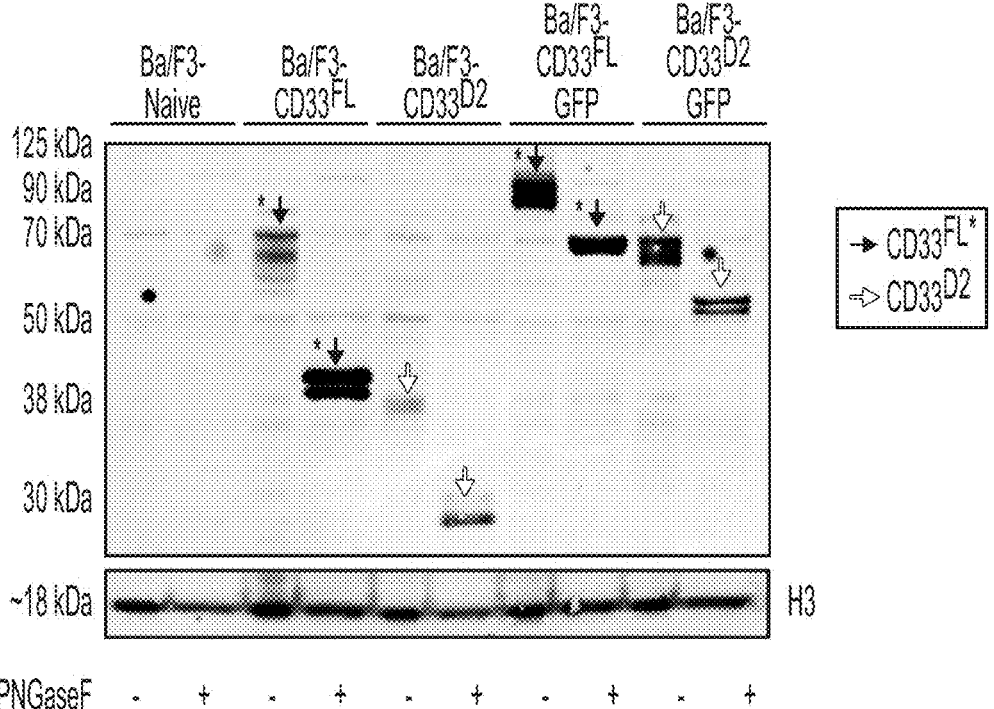
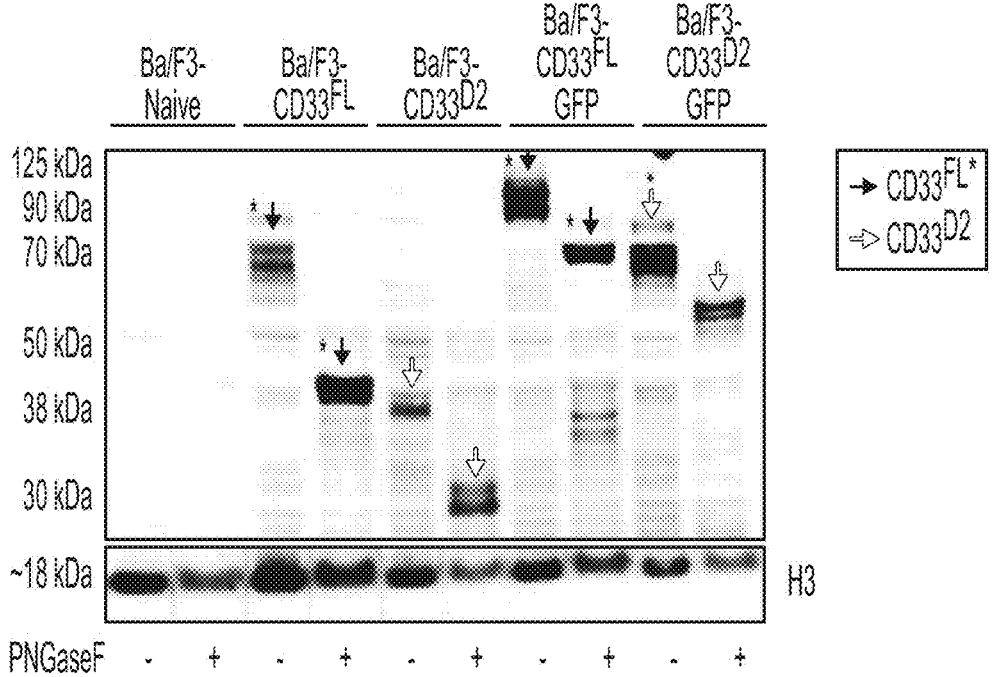
FIG. 1C

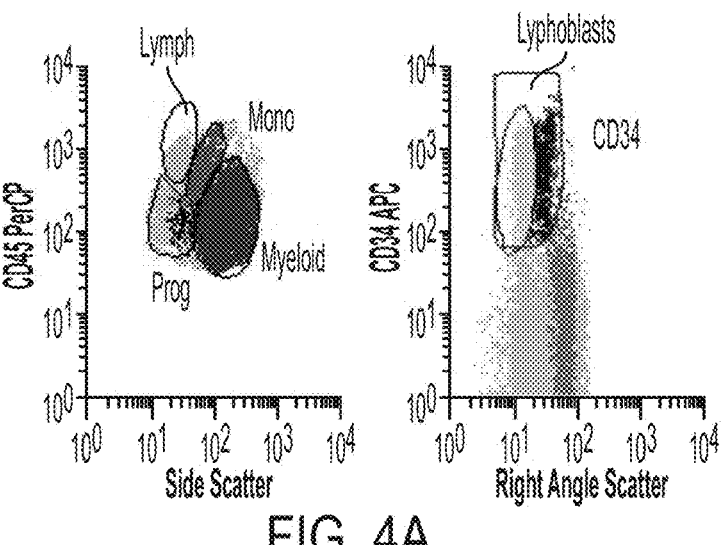
FIG. 4A
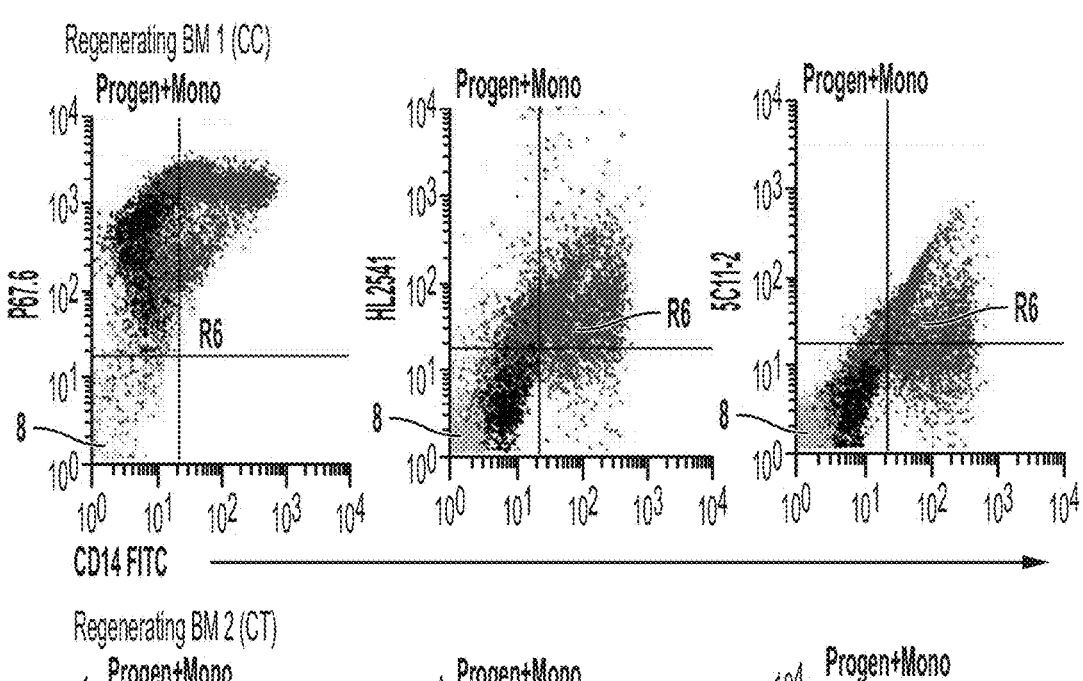
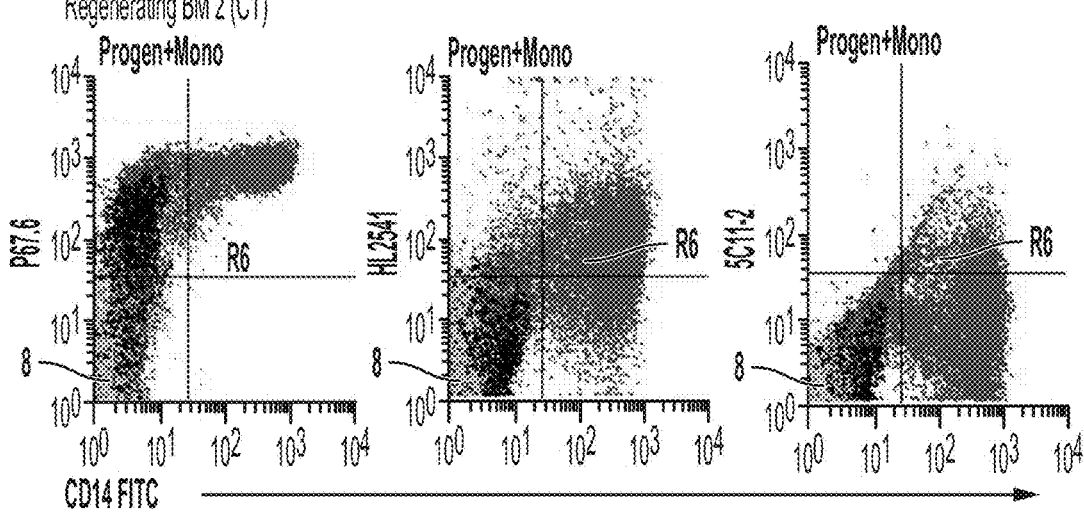
FIG. 4B

```
 10         20         30         40         50         60         70         80
MPLILLLPLI WAGALAMDPN FWLQVQESVT VQEGLCVLVP CTFFHPIPYY DKNSPVHGYW FREGATISRD SPVATNKLDQ 90        100        110        120        130        140        150        160
EVQEETQGRF RLLGDPSRNN CSLSIVDARR RDNGSYFFRM ERGSTKYSYK SPQLSVHVTD LTHRPKILIPG TILEPGHSKN 170        180        190        200        210        220        230        240
LTCSVSWACE QGTPPIFSWL SAAPTSLGPR TTHSSVLIIT PRPQDHGTNL TCQVKFAGAG VTTERTIQLN VTYVPQNPTT 250        260        270        280        290        300        310        320
GIFPGDGSGK QETRAGVVHG AIGGAGVTAL LALCLCLIFF IVKTHRRKAA RTAVGRNDTH PTTGSASPKH QKKSKLHGPT 330        340        350        360
ETSSCSGAAP TVEMDEELHY ASINFHGMNP SKDTSTEYSE VRTQ
```

IgV-like domain
IgC-like domain
5C11-2 Epitope *
HL2541 Epitope **

FIG. 6

CD33 ANTIBODIES

CROSS REFERENCE TO RELATED APPLICATIONS

This application is a national stage filing under 35 U.S.C. 371 of International Patent Application Serial No. PCT/US2021/050449, filed Sep. 15, 2021, entitled "CD33 ANTIBODIES", which claims priority to U.S. provisional Application No. 63/078,686, filed Sep. 15, 2020, the contents of each of which are herein incorporated by reference in their entirety.

STATEMENT OF NON-GOVERNMENT FUNDING

This invention was created in part by funding received from Grant No. 6610-20 awarded by the Leukemia & Lymphoma Society.

SEQUENCE LISTING

The instant application contains a Sequence Listing which has been submitted in ASCII format via EFS-Web and is hereby incorporated by reference in its entirety. Said ASCII copy, created on Feb. 14, 2023, is named U119570166US01-SEQ-KZM and is 18,562 bytes in size.

BACKGROUND

The re-approval and success of the anti-CD33 immunoconjugate gemtuzumab ozogamicin (GO) has spurred advances in the development of other CD33-directed immunotherapies for acute myeloid leukemia (AML). GO recognizes an epitope present in exon 2 of CD33. Thus, patients expressing a variant T (CT and TT) allele at splicing SNP rs12459419, which results in expression of a CD33 variant lacking an IgV domain (CD33$^{D2}$), show no clinical benefit from GO whereas the patients with CC genotype demonstrate significant reduction in relapse risk and improved survival when given GO. The reliance of current CD33-directed immunotherapies on binding to the IgV domain necessitates the development of alternative strategies for patients expressing the CD33$^{D2}$ isoform.

SUMMARY

Aspects of the disclosure relate to compositions and methods for treating certain cancers (e.g., CD33$^+$) cancers, for example leukemias or lymphomas. The disclosure is based, in part, on antibodies and antigen binding fragments that bind to CD33 protein isoforms (e.g., CD33$^{D2}$ isoform) that are present in patients expressing a variant T allele at splicing SNP rs12459419. In some embodiments, antibodies described by the disclosure are useful for targeting agents, such as detectable agents and therapeutic agents, to CD33$^{D2}$-expressing cancer cells for the purposes of diagnosing and/or treating cancer. In some embodiments, antibodies or antigen binding fragments described by the disclosure are joined (e.g., conjugated or expressed as a fusion protein) with one or more additional antibodies or antigen binding fragments to produce an adaptable cell engager (ACE) or bispecific T cell engager (BiTE).

Accordingly, in some aspects, the disclosure provides an antibody or antigen binding fragment that specifically binds an amino acid sequence having at least 85% identity to SEQ ID NO: 1 or 2.

In some embodiments, an antibody specifically binds an amino acid sequence set forth as: SEQ ID NO: 3

In some aspects, the disclosure provides an antibody or antigen binding fragment that specifically binds to a CD33 protein, wherein the antibody or antigen binding fragment comprises a heavy chain variable region having a sequence set forth in SEQ ID NO: 16 (e.g., an amino acid sequence encoded by a nucleic acid set forth in SEQ ID NO: 18).

In some embodiments, the antibody further comprises a light chain variable region having a sequence set forth in SEQ ID NO: 17 (e.g., an amino acid sequence encoded by a nucleic acid sequence set forth in SEQ ID NO 19).

In some aspects, the disclosure provides an antibody that comprises a heavy chain variable region having a sequence set forth in SEQ ID NO 16 and a light chain variable region having a sequence set forth in SEQ ID NO: 17.

In some aspects, the disclosure provides an antibody or antigen binding fragment that specifically binds to a CD33 protein, wherein the antibody or antigen binding fragment comprises variable heavy chain region comprising a complementarity determining region 1 (CDRH1) having a sequence set forth in SEQ ID NO: 4 (e.g., an amino acid sequence encoded by a nucleic acid sequence set forth in SEQ ID NO: 5).

In some aspects, the disclosure provides an antibody or antigen binding fragment that specifically binds to a CD33 protein, wherein the antibody or antigen binding fragment comprises variable heavy chain region comprising a complementarity determining region 2 (CDRH2) having a sequence set forth as: SEQ ID NO: 6 (e.g., an amino acid sequence encoded by a nucleic acid sequence set forth in SEQ ID NO: 7).

In some aspects, the disclosure provides an antibody or antigen binding fragment that specifically binds to a CD33 protein, wherein the antibody or antigen binding fragment comprises variable heavy chain region comprising a complementarity determining region 3 (CDRH3) having a sequence set forth as: SEQ ID NO: 8 (e.g., an amino acid sequence encoded by a nucleic acid sequence set forth in SEQ ID NO: 9).

In some aspects, the disclosure provides an antibody or antigen binding fragment that specifically binds to a CD33 protein, wherein the antibody or antigen binding fragment comprises variable light chain region comprising a complementarity determining region 1 (CDRL1) having a sequence set forth as: SEQ ID NO: 10 (e.g., an amino acid sequence encoded by a nucleic acid sequence set forth in SEQ ID NO: 11)

In some aspects, the disclosure provides an antibody or antigen binding fragment that specifically binds to a CD33 protein, wherein the antibody or antigen binding fragment comprises variable light chain region comprising a complementarity determining region 2 (CDRL2) having a sequence set forth as: SEQ ID NO: 12 (e.g., an amino acid sequence encoded by a nucleic acid sequence set forth in SEQ ID NO: 13).

In some aspects, the disclosure provides an antibody or antigen binding fragment that specifically binds to a CD33 protein, wherein the antibody or antigen binding fragment comprises variable light chain region comprising a complementarity determining region 3 (CDRL3) having a sequence set forth as: SEQ ID NO: 14 (e.g., an amino acid sequence encoded by a nucleic acid sequence set forth in SEQ ID NO: 15).

In some embodiments, a CD33 protein is a CD33$^{D2}$ protein.

In some aspects, the disclosure provides an antibody, or antigen binding fragment, that specifically binds to CD33 and that comprises six complementarity determining regions (CDRs): CDRH1, CDRH2, CDRH3, CDRL1, CDRL2, and CDRL3, wherein CDRH1 comprises a sequence as set forth in SEQ ID NO: 4, CDRH2 comprises a sequence as set forth in SEQ ID NO: 6, CDRH3 comprises a sequence as set forth in SEQ ID NO: 8, CDRL1 comprises a sequence as set forth in SEQ ID NO: 10, CDRL2 comprises a sequence as set forth in SEQ ID NO: 12, and CDRL3 comprises a sequence as set forth in SEQ ID NO: 14.

In some embodiments, the antibody comprises the heavy chain variable domain sequence of SEQ ID NO: 16. In some embodiments, the antibody comprises the light chain variable domain sequence of SEQ ID NO: 17.

In some embodiments, an antibody is a chimeric antibody, optionally a human/mouse chimeric antibody. In some embodiments, an antibody is a humanized antibody. In some embodiments, an antibody is a monoclonal antibody. In some embodiments, an antibody or antigen binding fragment, is a monoclonal antibody, a humanized antibody, a diabody, a chimeric antibody, a Fab fragment, a F(ab')2 fragment, affibody, or an Fv fragment.

In some embodiments, an antibody or antigen binding fragment comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains.

In some aspects, the disclosure provides an isolated nucleic acid encoding a protein comprising three complementarity determining regions (CDRs): CDRH1, CDRH2, and CDRH3, wherein CDRH3 comprises a sequence as set forth in SEQ ID NO: 8. In some embodiments, a CDRH1 comprises a sequence as set forth in SEQ ID NO: 4. In some embodiments, a CDRH2 comprises a sequence as set forth in SEQ ID NO: 6.

In some aspects, the disclosure provides an isolated nucleic acid encoding a protein comprising three complementarity determining regions (CDRs): CDRL1, CDRL2, and CDRL3, wherein CDRL3 comprises a sequence as set forth in SEQ ID NO: 14. In some embodiments, a CDRL1 comprises a sequence as set forth in SEQ ID NO: 10. In some embodiments, a CDRL2 comprises a sequence as set forth in SEQ ID NO: 12.

In some aspects, the disclosure provides an isolated nucleic acid comprising a sequence as set forth in a sequence selected from the group consisting of SEQ ID NO: 5, 7, 9, 11, 13, 15, 18, and 19.

In some aspects, the disclosure provides a cell comprising an isolated nucleic acid as described herein. In some embodiments, a cell is a bacterial cell, a yeast cell, a mammalian cell, or an insect cell. In some embodiments, a cell is a hybridoma cell. In some embodiments, a hybridoma cell is a B-cell. In some embodiments, a cell is in vitro.

In some embodiments, the disclosure provides a composition comprising an antibody or antigen binding fragment as described herein, and a pharmaceutically acceptable excipient.

In some aspects, the disclosure provides a method for targeting an agent to a cancer cell in a subject, the method comprising administering to the subject a composition comprising an antibody, or the composition as described herein, coupled to a targeted agent, wherein the antibody binds to a CD33 protein on the surface of the cancer cell in the subject.

In some embodiments, an antibody comprises a heavy chain variable region having a sequence set forth as: SEQ ID NO: 16. In some embodiments, an antibody further comprises a light chain variable region having a sequence set forth as: SEQ ID NO: 17.

In some embodiments, an antibody comprises a heavy chain variable region having a sequence set forth as: SEQ ID NO 16 and a light chain variable region having a sequence set forth as: SEQ ID NO: 17.

In some embodiments, a targeted agent is a detectable moiety. In some embodiments, a detectable moiety is selected from the group consisting of a radioactive isotope, a magnetic compound, an x-ray absorber, a chemical compound, a biological tag, and a fluorescent molecule.

In some embodiments, a targeted agent is a therapeutic agent. In some embodiments, a therapeutic agent is a cytotoxic moiety or an immunomodulatory moiety. In some embodiments, a therapeutic agent is calicheamicin.

In some embodiments, a cancer cell is a CD33 positive (CD33$^+$) cancer cell. In some embodiments, a CD33 protein is CD33$^{D2}$.

In some embodiments, the cancer is a leukemia or a lymphoma. In some embodiments, the cancer is acute myeloid leukemia (AML).

In some embodiments, a subject comprises a variant T allele at rs12459419. In some embodiments, a subject is a mammal. In some embodiments, a subject is a human.

In some aspects, the disclosure provides a method for treating cancer, the method comprising administering to a subject having cancer an effective amount of an antibody or an effective amount composition as described herein.

In some embodiments, administration of the effective amount of the antibody or the composition reduces the number of cancer cells in the subject. In some embodiments, a cancer cell is a CD33 positive (CD33$^+$) cancer cell. In some embodiments, a CD33 protein is CD33$^{D2}$.

In some embodiments, the cancer is a leukemia or a lymphoma. In some embodiments, the cancer is acute myeloid leukemia (AML).

In some embodiments, a subject comprises a variant T allele at rs12459419. In some embodiments, a subject is a mammal. In some embodiments, a subject is a human.

Aspects of the disclosure relate to an adaptable cell engager (ACE) comprising an anti-CD33$^{D2}$ antibody of the disclosure, and an anti-CD3 antibody. Aspects of the disclosure relate to a recombinant protein in a BiTE format comprising an anti-CD33$^{D2}$ antibody of the disclosure, and an anti-CD3 antibody. In some embodiments, the anti-CD33$^{D2}$ antibody of the ACE or recombinant protein (e.g., BiTE) has a polypeptide sequence set forth as: SEQ ID NO: 21. In some embodiments, the anti-CD33$^{D2}$ antibody of the ACE or recombinant protein (e.g., BiTE) comprises one or more polypeptides selected from the amino acid sequences set forth as: SEQ ID NOs: 4, 6, 8, 10, 12, or 14. In some embodiments, the anti-CD33$^{D2}$ antibody of the ACE or recombinant protein (e.g., BiTE) comprises SEQ ID NOs: 4, 6, 8, 10, 12, and 14. In some embodiments, the anti-CD3 antibody of the ACE or recombinant protein (e.g., BiTE) comprises a polypeptide sequence having 90%, 95%, or 99% sequence identity to the amino acid sequence set forth as: SEQ ID NO: 22. In some embodiments, the anti-CD3 antibody of the ACE or recombinant protein (e.g., BiTE) comprises the polypeptide sequence set forth as: SEQ ID NO: 22.

In some embodiments, the anti-CD33$^{D2}$ antibody and the anti-CD3 antibody of the ACE or recombinant protein (e.g., BiTE) are conjugated by a linker. In some embodiments, the linker comprises a streptavidin linker or a biotin linker.

Aspects of the disclosure relate to an isolated nucleic acid encoding a recombinant protein (e.g., BiTE) comprising an anti-CD33$^{D2}$ antibody as described herein, and an anti-CD3 antibody, as described herein. Aspects of the disclosure relate to a cell comprising said isolated nucleic acid.

Aspects of the disclosure relate to compositions comprising an ACE or recombinant protein (e.g., BiTE) comprising an anti-CD33$^{D2}$ antibody as described herein, and an anti-CD3 antibody, as described herein.

Aspects of the disclosure relate to methods for targeting an agent to a cancer cell in a subject, the method comprising administering to the subject a composition comprising an ACE or recombinant protein (e.g., BiTE) comprising an anti-CD33$^{D2}$ antibody as described herein, and an anti-CD3 antibody, as described herein, coupled to a targeted agent, wherein the ACE or the recombinant protein (e.g., BiTE) binds to a CD33 protein isoform on the surface of the cancer cell in the subject. In some embodiments, the targeted agent is a detectable moiety. In some embodiments, the detectable moiety is selected from the group consisting of a radioactive isotope, a magnetic compound, an x-ray absorber, a chemical compound, a biological tag, and a fluorescent molecule. In some embodiments, the targeted agent is a therapeutic agent. In some embodiments, the therapeutic agent is a cytotoxic moiety or an immunomodulatory moiety. In some embodiments, the therapeutic agent is calicheamicin. In some embodiments, the cancer cell is a CD33 positive cancer cell. In some embodiments, the CD33 is CD33$^{D2}$. In some embodiments, the cancer is a leukemia or a lymphoma, optionally wherein the cancer is acute myeloid leukemia. In some embodiments, the subject comprises a variant T allele at rs12459419. In some embodiments, the subject is a mammal, optionally a human.

Aspects of the disclosure relate to methods for treating cancer, the method comprising administering to a subject having cancer an effective amount of the ACE or recombinant protein (e.g., BiTE) comprising an anti-CD33$^{D2}$ antibody as described herein, and an anti-CD3 antibody, as described herein, or an effective amount of a composition comprising said ACE or recombinant protein (e.g., BiTE), as described herein. In some embodiments, administration of the ACE, recombinant protein, or composition increases T cell killing of cancer cells in the subject. In some embodiments, the cancer cell is a CD33 positive cancer cell. In some embodiments, the CD33 is CD33$^{D2}$. In some embodiments, the cancer is a leukemia or a lymphoma, optionally wherein the cancer is acute myeloid leukemia. In some embodiments, the subject comprises a variant T allele at rs12459419. In some embodiments, the subject is a mammal, optionally a human.

BRIEF DESCRIPTION OF DRAWINGS

FIGS. 1A-1F show generation and confirmation of IgC-specific CD33 antibodies. FIG. 1A shows flow cytometry screen for GFP expression on Naïve and engineered Ba/F3 cells. FIG. 1B shows flow cytometry screen for CD33$^{FL}$ by P67.6-PE (500 ng) on engineered Ba/F3 cells. FIG. 1C shows recognition of CD33 is confirmed by western blotting analysis of engineered BaF3 cells using anti-CD33 C-terminus mAb E6 (ITIM-directed; 1:100) and IgC specific HL2541 (1:50). FIGS. 1D-1E show recognition of CD33 in flow cytometry assays using 5C11-2-PE and HL2541-PE mAbs (500 ug each) and engineered Ba/F3 cells. FIG. 1F shows recognition of CD33 in confocal microscopic immunofluorescence assays using 5C11-2 and HL2541 mAbs (2 µg each) and engineered Ba/F3 cells.

FIG. 2A shows AML cell lines of different rs12459419 genotypes stained with either P67.6-PE, HL2541-PE, or 5C11-2-PE antibodies (500 ng each). FIGS. 2B and 2C show Western blotting of AML cell lines using anti-CD33 C-terminus mAb E6 (1:100) and IgC specific mAbs HL2541 (1:50) and 5C11-2 (1:250). Immunophenotyping of AML cell lines revealed CD34, CD14, and CD45 cell surface expression.

FIG. 3A shows a gating strategy for analysis of CD33$^{D2}$ expression on CD34$^+$CD14$^-$CD45$^{dim}$ AML progenitors, CD14$^+$ mature monocytes, and other CD45$^{high}$ lymphocytes using CD34-APC (100 ng), CD14-Pacific Blue (800 ng), and CD45-Super Bright 600 antibodies (150 ng). Cells were first gated by size and viability. Subsequently, CD14$^-$ cells were gated, followed by a gate set to capture the CD14 CD45$^{dim}$ and CD14$^-$CD45$^{high}$ (other lymphocytes), and finally a gate to capture CD14$^-$CD45$^{dim}$CD34$^+$ cells (AML progenitors). All gates were set using unstained samples as a negative. FIG. 3B shows staining for CD33$^{D2}$ using HL2541-PE and 5C11-2-PE (500 ng each) on CD34$^+$CD14$^-$ CD45$^{dim}$ AML progenitors from primary BM AML specimen of different rs12459419 genotypes. FIG. 3C shows staining for CD33$^{C2}$ using HL2541-PE and 5C11-2-PE on CD14$^+$ mature monocytes from primary BM AML specimen of different rs12459419 genotypes.

FIGS. 4A-4B show profiling of CD33$^{D2}$ cell surface expression on bone marrow specimens obtained at remission. FIG. 4A shows a gating strategy for analysis of CD33$^{D2}$ expression on CD34$^+$CD14$^-$CD45$^{dim}$ progenitors (both lymphoblastic and myeloblastic as gated based on right angle scatter properties) and CD14$^+$ mature monocytes as well as other myeloid cells. All gates were set using unstained samples as a negative. Circled cells represent CD34$^+$CD14$^-$CD45$^{dim}$ myeloblastic progenitors, CD34$^+$ CD14$^-$CD45$^{dim}$ lymphoblastic progenitors, CD14$^+$ monocytes, and other myeloid cells respectively. FIG. 4B shows a dot plot of overlay of progenitor cells and monocytes stained with P67.6 to measure CD33$^{FL}$ expression and HL2541 and 5C11-2 to measure CD33$^{D2}$ expression.

FIG. 5A (left) shows a flow cytometry screen for GFP expression on Ba/F3-naïve cells and Ba/F3 cells engineered to express CD33$^{FL}$, CD33$^{D2}$, and their respective fusion proteins. FIG. 5B (right) shows flow cytometry screens for cell surface CD33$^{FL}$ by P67.6-PE (500 ng) on all B a/F3 cells confirming that GFP does not disrupt native folding or surface expression.

FIG. 6 shows epitopes targeted by HL2451 and 5C11-2, CD33$^{FL}$, sequence with IgV domain, IgC domain, HL2541, and 5C11-2 noted. Epitopes shown are based on peptides used as immunogens for developments of each antibody.

FIG. 9A shows cell surface expression on AML progenitors from primary BM AML specimens from rs12459419 "CC" genotype patients. FIG. 9B shows cell surface expression on AML progenitors from primary BM AML specimens from rs12459419 "CT" genotype patients. FIG. 9C shows cell surface expression on AML progenitors from primary BM AML specimens from rs12459419 "TT" genotype patients.

FIG. 10A shows cell surface expression on CD14$^+$ mature monocytes from primary BM AML specimens from rs12459419 "CC" genotype patients. FIG. 10B shows cell surface expression on CD14$^+$ mature monocytes from primary BM AML specimens from rs12459419 "CT" genotype patients. FIG. 10C shows cell surface expression on CD14$^+$ mature monocytes from primary BM AML specimens from rs12459419 "TT" genotype patients.

FIG. 12A shows a dot plot overlay of progenitor cells and monocytes stained with P67.6 to show CD33$^{FL}$ expression and HL2541 and 511C-2 to measure CD33$^{D2}$ expression. FIG. 12B shows a dot plot overlay of progenitor cells and monocytes stained with HL2541 to measure CD33$^{D2}$ expression.

FIG. 17A shows toxicity at 1:1 E:T. FIG. 17B shows toxicity at 2:1 E:T. FIG. 17C shows toxicity at 5:1 E:T.

FIG. 19A shows 1×ACE. FIG. 19B shows 2×ACE. FIG. 19C shows 5×ACE.

FIG. 21A shows the percentage of dead cells at 1:1 E:T. FIG. 21B shows the percentage of dead cells at 2:1 E:T. FIG. 21C shows the percentage of dead cells at 5:1 E:T.

FIG. 24A shows 1×ACE. FIG. 24B shows 2×ACE. FIG. 24C shows 5×ACE.

DETAILED DESCRIPTION

Figure 1A:
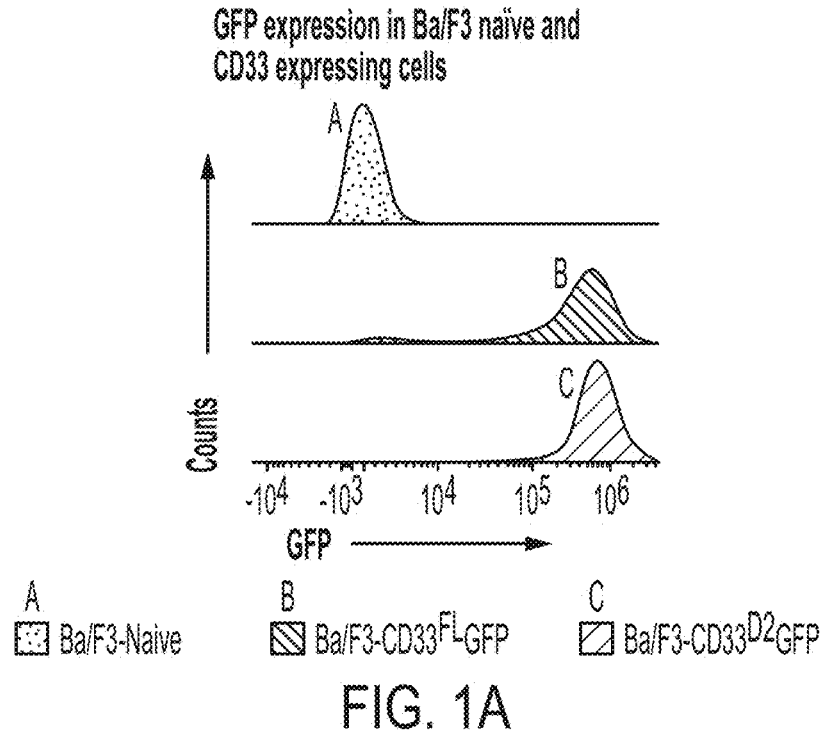

Aspects of the disclosure relate to methods and compositions for treating certain cancers, (e.g., CD33$^+$ cancers, such as leukemias and lymphomas). The disclosure is based, in part, on antibodies that specifically bind to CD33 (e.g., full length CD33, CD33$^{D2}$, etc.) isoforms that are present in patients expressing a variant T allele at splicing single nucleotide polymorphism (SNP) rs12459419.

As used herein, "specifically binds" refers to a binding agent's (e.g., antibody's) preferential interaction with (e.g., affinity to) a given ligand over other agents in a sample. For example, a specific binding agent that specifically binds a given ligand binds the given ligand under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

The ability of an antigen binding molecule (e.g., an antibody or antigen binding fragment of the disclosure) to bind to a specific antigen (e.g., full length CD33 or CD33$^{D2}$) can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., *Glyco J* 17, 323-329 (2000)), and traditional binding assays (Heeley, *Endocr Res* 28, 217-229 (2002)). The affinity of a molecule×(e.g., an antibody or antigen binding fragment of the disclosure) for its partner Y (e.g., the specific antigen or ligand of interest; e.g., full length CD33 or CD33$^{D2}$) can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

In one embodiment, the extent of binding of an antigen binding molecule (e.g., an antibody or antigen binding fragment of the disclosure) to an unrelated protein (e.g., not the specific antigen or ligand of interest; e.g., not full length CD33 or CD33$^{D2}$) is less than about 10% of the binding of the antigen binding molecule to the antigen as measured, e.g. by SPR. In certain embodiments, a molecule (e.g., an antibody or antigen binding fragment of the disclosure) that binds to the antigen (e.g., the specific antigen or ligand of interest; e.g., full length CD33 or CD33$^{D2}$) has a dissociation constant (Kd) of ≤1 μM, ≤100 nM, ≤10 nM, ≤1 nM, ≤0.1 nM, ≤0.01 nM, or ≤0.001 nM (e.g. 10$^{-7}$ M or less, e.g. from 10$^{-7}$ M to 10$^{-13}$ M, e.g. from 10$^{-9}$ M to 10$^{-13}$ M). As used herein, the term "high affinity" of an antibody refers to an antibody having a Kd of 10$^{-9}$ M or less and even more particularly 10$^{-10}$ M or less for a target antigen. The term "low affinity" of an antibody refers to an antibody having a Kd of 10$^{-8}$ or higher. In some embodiments, an antibody or antigen binding fragment of the disclosure has a Kd for CD33$^{D2}$ which is lower than other anti-CD33 antibodies known in the art (e.g., has high affinity for CD33$^{D2}$, or specifically binds CD33$^{D2}$). In some embodiments, an antibody or antigen binding fragment of the disclosure has a Kd for CD33$^{D2}$ which is 1-fold, 2-fold, 3-fold, 4-fold, or 5-fold lower than other anti-CD33 antibodies known in the art.

Anti-CD33 Antibodies

CD33 is a transmembrane receptor expressed on cells of myeloid lineage and functions as an inhibitor of apoptosis. In some embodiments, a CD33 protein is a human CD33 protein, and is encoded by the nucleic acid sequence set forth in NCBI Reference Sequence NM_001772.4. CD33 has been observed to have several isoforms, including CD33$^{D2}$ (also referred to as CD33$^{ΔE2}$), and CD33$^{E7a}$ (which contains an alternative exon 7). In some embodiments, CD33$^{D2}$ comprises the sequence set forth in NCBI Reference Sequence NM_001082618.2 (SEQ ID NO: 2; e.g., an amino acid sequence encoded by the nucleic acid sequence set forth in SEQ ID NO: 20).

Accordingly, in some embodiments, the disclosure provides antibodies and antigen binding fragments that bind to CD33 isoforms, such as CD33$^{D2}$, on the surface of cancer cells. As used herein, the term "antibody" generally refers to an immunoglobulin. All derivatives thereof which maintain or possess specific binding ability are also provided herein. An antibody preparation may be monoclonal or polyclonal. As used herein, the term "antibody fragment" or "antigen binding fragment" refers to any derivative of an antibody which is less than full-length. Generally, an antigen binding fragment retains at least a significant portion of the full-length antibody's specific binding ability. Examples of antigen binding fragments include, but are not limited to, Fab, Fab', F(ab')2, scFv, Fv, dsFv diabody, affibodies, and Fd fragments. Antigen binding fragments may be produced by any appropriate means. For instance, an antigen binding fragment may be enzymatically or chemically produced by fragmentation of an intact antibody, or it may be recombinantly produced from a gene encoding the partial antibody sequence. Alternatively, an antigen binding fragment may be wholly or partially synthetically produced. An antigen binding fragment may optionally be a single chain antibody fragment. Alternatively, a fragment may comprise multiple chains which are linked together, for instance, by disulfide linkages. An antigen binding fragment may also optionally be a multimolecular complex. A functional antigen binding fragment will typically comprise at least about 50 amino acids and more typically will comprise at least about 200 amino acids.

In some embodiments, antibodies, also known as immunoglobulins, are tetrameric glycosylated proteins composed of two light (L) chains of approximately 25 kDa each and two heavy (H) chains of approximately 50 kDa each. Two types of light chains, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG$_1$, IgG$_2$, IgG$_3$, IgG$_4$, IgA$_1$, and IgA$_2$. In some embodiments, an anti-CD33 antibody is of an IgG$_1$ subclass. In some embodiments, an anti-CD33 antibody is of an IgG$_2$ subclass.

Each light chain typically includes an N-terminal variable (V) domain (V$_L$) and a constant (C) domain (C$_L$). Each heavy chain typically includes an N-terminal V domain (V$_H$), three or four C domains (C$_H$1-3), and a hinge region. The C$_H$ domain most proximal to V$_H$ is designated as C$_H$1. In some embodiments, a constant (C) domain is a mouse constant domain. In some embodiments, a constant domain is a human constant domain. The V$_H$ and V$_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Eds.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

In some embodiments, anti-CD33 antibodies of the present disclosure and the nucleic acid molecules of the present disclosure that encode the antibodies include the CDR amino acid and nucleic acid sequences shown in Table 1 below.

TABLE 1

| Exemplary amino acid and nucleic acid sequences for the CDRs of the disclosure. | | | | | | |
|---|---|---|---|---|---|---|
| Antibody | CDRH1 | CDRH2 | CDRH3 | CDRL1 | CDRL2 | CDRL3 |
| HL2541 | SEQ ID NO: 4 | SEQ ID NO: 6 | SEQ ID NO: 8 | SEQ ID NO: 10 | SEQ ID NO: 12 | SEQ ID NO: 14 |
| | SEQ ID NO: 5 | SEQ ID NO: 7 | SEQ ID NO: 9 | SEQ ID NO: 11 | SEQ ID NO: 13 | SEQ ID NO: 15 |

In some embodiments, anti-CD33 antibodies (e.g., anti-CD33$^{D2}$ antibodies) of the disclosure include any antibody or antigen binding fragment that includes a CDRH1, CDRH2, CDRH3, CDRL1, CDRL2, or CDRL3, or combinations thereof, as shown in Table 1. In some embodiments, anti-CD33 antibodies (e.g., anti-CD33$^{D2}$ antibodies) include the CDRH1, CDRH2, CDRH3, CDRL1, CDRL2, and CDRL3 of any one of the antibodies shown in Table 1. The disclosure also includes any nucleic acid sequence that encodes a CDRH1, CDRH2, CDRH3, CDRL1, CDRL2, or CDRL3 as shown in Table 1. Antibody heavy and light chain CDR3 domains may play a particularly important role in the binding specificity/affinity of an antibody for an antigen. Accordingly, the anti-CD33 antibodies (e.g., anti-CD33$^{D2}$ antibodies) of the disclosure, or the nucleic acid molecules thereof, may include at least the heavy and/or light chain CDR3s as shown in Table 1 or as set forth by SEQ ID NOs: 8 and 14.

The complete amino acid and nucleic acid sequences for the heavy chain variable region and light chain variable region of the antibodies are listed in Table 2.

TABLE 2

Exemplary complete amino acid and nucleic acid sequences for the heavy and light chain variable regions of the disclosure.

| Antibody | Heavy Chain Variable Region | Light Chain Variable Region |
|----------|------------------------------|------------------------------|
| HL2541 | SEQ ID NO: 16 | SEQ ID NO: 17 |
| | SEQ ID NO: 18 | SEQ ID NO: 19 |

In some embodiments, anti-CD33 antibodies (e.g., anti-CD33$^{D2}$ antibodies) of the disclosure include any antibody that includes a heavy chain variable domain or a light chain variable domain, or both, as shown in Table 2, or as described in the sequence listing of this disclosure (e.g., SEQ ID NOs: 16 or 17). The disclosure also includes any nucleic acid molecule encoding an antibody that includes a heavy chain variable domain or a light chain variable domain nucleic acid sequence, or both, as shown in Table 2, or as described in the sequence listing of this disclosure (e.g., SEQ ID NOs: 18 or 19).

Anti-CD33 antibodies (e.g., anti-CD33$^{D2}$ antibodies) of this disclosure may optionally comprise antibody constant regions or parts thereof. For example, a V$_L$ domain may be attached at its C-terminal end to a light chain constant domain like Cη or Cλ. Similarly, a V$_H$ domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include V$_H$ and V$_L$ domains, or an antigen binding portion thereof, combined with constant regions known in the art.

In certain embodiments, the V$_H$ and/or V$_L$ domains may be reverted to germline sequence, e.g., the framework region (FR) of these domains are mutated using conventional molecular biology techniques to match those produced by the germline cells. In other embodiments, the FR sequences remain diverged from the consensus germline sequences. In some embodiments, anti-CD33 antibodies are chimeric or humanized antibodies.

It should be appreciated that, in some embodiments, the disclosure contemplates variants (e.g., homologs) of amino acid and nucleic acid sequences for the heavy chain variable region and light chain variable region of the antibodies. "Homology" refers to the percent identity between two polynucleotides or two polypeptide moieties. The term "substantial homology", when referring to a nucleic acid, or fragment thereof, indicates that, when optimally aligned (with appropriate gaps, insertions, or deletions) with another nucleic acid (or its complementary strand), there is nucleotide sequence identity in about 90 to 100% of the aligned sequences. For example, in some embodiments, nucleic acid sequences sharing substantial homology have at least 90%, at least 91%, at least 92% at least 93%, at least 94%, at least 95%, at least 96%, at least 97%, at least 98%, or at least 99% sequence identity to one another. When referring to a polypeptide, or fragment thereof, the term "substantial homology" indicates that, when optimally aligned (with appropriate gaps, insertions or deletions) with another polypeptide, there is nucleotide sequence identity in about 90 to 100% of the aligned sequences. The term "highly conserved" means at least 80% identity, preferably at least 90% identity, and more preferably, over 97% identity. For example, in some embodiments, highly conserved proteins share at least 85%, at least 90%, at least 91%, at least 92% at least 93%, at least 94%, at least 95%, at least 96%, at least 97%, at least 98%, or at least 99% identity. In some cases, highly conserved may refer to 100% identity. Identity is readily determined by one of skill in the art by, for example, the use of algorithms and computer programs known by those of skill in the art.

In some embodiments, an anti-CD33 antibody (e.g., anti-CD33$^{D2}$ antibody) of the disclosure can bind to CD33 (e.g., CD33$^{D2}$) with high affinity, e.g., with a Kd less than $10^{-7}$ M, $10^{-8}$M, $10^{-9}$M, $10^{-10}$ M, $10^{-11}$ M, or lower. For example, anti-CD33 antibodies or antigen binding fragments thereof can bind to CD33 (e.g., CD33$^{D2}$) with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to CD33 and that have an affinity of 50 nM or lower (e.g., 20 nM or lower, 10 nM or lower, 500 pM or lower, 50 pM or lower, or 5 pM or lower). The affinity and binding kinetics of the anti-CD33 antibody can be tested using any method known in the art including but not limited to biosensor technology (e.g., OCTET or BIACORE).

Aspects of the disclosure relate to anti-CD33 antibodies that are conjugated (e.g., connected) to one or more modifying agents. Accordingly, in some embodiments, antibodies or antigen binding fragments of the disclosure may be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of CD33$^+$ cells. The detectable substance may be coupled or conjugated either directly to the polypeptides of the disclosure or indirectly, through an intermediate (such as, for example, a linker known in the art) using techniques known in the art. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes. The detectable substance may be coupled or conjugated either directly to the anti-CD33 antibodies of the disclosure or indirectly, through an intermediate (such as, for example, a linker known in the art) using techniques known in the art. Anti-CD33 antibodies conjugated to a detectable substance may be used for diagnostic assays.

In some embodiments, an anti-CD33 antibody of the disclosure (or antigen binding fragment thereof) is conjugated (e.g., connected) to an anti-CD3 antibody (or antigen binding fragment thereof). Two antibodies or antigen binding fragments may be directly connected (e.g., expressed as a single fusion protein without a linker region) or indirectly connected (e.g., conjugated together using a linker, for example an amino acid (e.g., peptide) linker or post-translational chemical linkers). As used herein, the term "linker" refers to a molecule or sequence, such as an amino acid sequence, that attaches, as in a bridge, one molecule or sequence to another molecule or sequence. "Linked," "conjugated," or "coupled" means attached or bound by covalent bonds, or non-covalent bonds, or other bonds, such as van der Waals forces.

In some embodiments, the two antibodies (or antigen binding fragments thereof) of an ACE or recombinant protein (e.g., BiTE) are conjugated by a linker. In some embodiments, the two or more antibodies (or antigen binding fragments thereof) of an ACE or recombinant protein (e.g., BiTE) are conjugated by two or more linkers, for example streptavidin/biotin linkers, click chemistry linkers, etc. Linkers may be of a length and sequence sufficient to ensure that each of the first and second domains can, independently from one another, retain their differential binding specificities. In some embodiments, the linker is of sufficient length to enable the domains of the antibodies or antigen binding fragments to fold in such a way as to permit binding to target antigen and/or not destroy the desired properties of the antibodies or antigen binding fragments.

In some embodiments, the linker is a streptavidin linker. In some embodiments, the linker is a biotin linker. Streptavidin is a 60 KDa tetrameric protein with a globular subunit organization of 5 nm in size (Kuzuya et al., *Nucleic Acids Symp Ser (Oxf)*. 2008; (52):681-2). Streptavidin homotetramers have an extraordinarily high affinity for biotin (also known as vitamin B7 or vitamin H). With a dissociation constant (Kd) on the order of $\approx 10^{-14}$ mol/L, the binding of biotin to streptavidin is one of the strongest non-covalent interactions known in nature. Streptavidin is broadly utilized as linker in biotechnology because the conjugation scheme using the wild-type (WT) streptavidin provides a very stable bond under well-preserved biological conditions (Kd~$10^{-15}$, pH 3-13) (Weber et al., *Science*, Jan. 6, 1989; 243(4887): 85-8; Katz, *J Mol Biol*, Dec. 19, 1997; 274(5):776-800). The strong streptavidin-biotin interaction can be used to attach various biomolecules to one another, for example the conjugation of an anti-CD33 antibody of the disclosure (or antigen binding fragment thereof) to an anti-CD3 antibody (or antigen binding fragment thereof), as described herein.

As will be understood, in some embodiments, a light chain variable region (or a portion thereof) is conjugated (e.g., connected) to a heavy chain variable region (or a portion thereof) for each antibody or antigen binding fragment thereof comprised in an ACE or recombinant protein (e.g., BiTE) of the disclosure. In some embodiments, the light chain variable region (or a portion thereof) is conjugated (e.g., connected) to the heavy chain variable region (or a portion thereof) via a linker. In some embodiments, the linker is a flexible linker. In some embodiments, the linker is a rigid linker. In some embodiments, the linker is a streptavidin linker, a biotin linker, a cleavable linker (e.g., chemically cleavable, enzymatically cleavable, photocleavable, etc.), a chemical linker, a photolinker (e.g., ketyl-reactive benzophenone (BP), anthraquinone (AQ), nitrene-reactive nitrophenyl azide (NPA), and carbene-reactive phenyl-(trifluoromethyl)diazirine (PTD)), a poly(ethylene glycol) (PEG) linker, or an amino acid (e.g., peptide) linker.

In some embodiments, the linker is an amino acid (e.g., peptide) linker. The amino acid linker may be of variable length and composition so long as the two variable domains are bridged without serious steric interference. The amino acid linker may comprise between 1 and 50 amino acids, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 amino acids. Suitable linkers may include, for example, those listed in Kortt, 1999, *J. Immunol. Meth.*, 231:177 and in Volkel et al., 2001, *Protein Eng.*, 14(10):

815-823. Typically, flexible amino acid linkers are comprised primarily of stretches of glycine and serine residues with some glutamic acid or lysine residues interspersed for solubility, while rigid peptide linkers are comprised of poly-proline (poly-P), poly-proline threonine (poly-PT), or poly-alanine (poly-A) motifs. In some embodiments, the amino acid linker is comprised of glycine residues (e.g., poly-Gly). In some embodiments, the amino acid linker is comprised of glycine and serine residues (e.g., poly-GlySer; e.g., a $(Gly_4Ser)_n$ repeat linker). In some embodiments, the amino acid linker is comprised of proline residues (e.g., poly-Pro). In some embodiments, the amino acid linker is comprised of proline and threonine residues (e.g., poly-ProThr). In some embodiments, the amino acid linker is comprised of alanine residues (e.g., poly-Ala).

In some embodiments, an anti-CD33 and an anti-CD3 antibody are conjugated post-translation, and the antibody-antibody conjugate (e.g., the recombinant antibody) is referred to as an "adaptable cell engager" or "ACE". In some embodiments, an ACE comprises two or more (e.g., 2, 3, 4, or more) antibodies (e.g., an anti-CD33 antibody and an anti-CD3 antibody). In some embodiments, an ACE comprises three antibodies (e.g., an anti-CD33 antibody, an anti-CD3 antibody, and a third antibody targeting a third tumor antigen). In some embodiments, an ACE comprises four antibodies (e.g., an anti-CD33 antibody, an anti-CD3 antibody, a third antibody targeting a third tumor antigen, and a fourth antibody targeting a fourth tumor antigen). In embodiments where an ACE comprises three or four antibodies, the ACE is referred to as a "multi-adaptable cell engager" or "MACE".

In other instances, the anti-CD33 and anti-CD3 antibodies may translated into a recombinant (e.g., fusion) protein. Such recombinant proteins are referred to as a "bi-specific T cell engagers" or "BiTEs". BiTEs, including anti-CD33/anti-CD3 BiTEs, have been previously described, and typically comprise a fusion protein having two single-chain variable fragments (scFvs) of different antibodies (e.g., an anti-CD33 and an anti-CD3 antibody) on a single peptide chain. In some embodiments, the size of a BiTE is about 55 kilodaltons. Further examples of BiTEs are described, for example in Nair-Gupta, et al. (2020), A novel C2 domain binding CD33×CD3 bispecific antibody with potent T-cell redirection activity against acute myeloid leukemia, *Blood Adv.*, 4(5):906-919; Godwin, et al. (2021), Targeting the membrane-proximal C2-set domain of CD33 for improved CD33-directed immunotherapy, *Leukemia*, 35(9):2496-2507; and Hoseini, et al. (2021), T cell engaging bispecific antibodies targeting CD33 IgV and IgC domains for the treatment of acute myeloid leukemia, *J Immunother Cancer*, 9(5):e002509.

As will be understood, each antibody or antigen binding fragment comprised within an ACE or recombinant protein (e.g., BiTE) of the disclosure will comprise an N terminus and a C terminus. The N-terminus is the start of a protein or polypeptide referring to the free amine group located at the end of a polypeptide. The C-terminus is the end of an amino acid chain (protein or polypeptide), terminated by a free carboxyl group (—COOH). According to conventional technique in the art, the peptide sequences herein are written (from left to right) N- to C-terminus. Within an ACE or recombinant protein (e.g., BiTE) of the disclosure, the anti-CD33 antibody or the anti-CD3 antibody may be situated in any order and in any orientation. In some embodiments, the anti-CD33 antibody or antigen binding fragment thereof is located N-terminal to the anti-CD3 antibody or antigen binding fragment thereof within the ACE or recombinant protein (e.g., BiTE). In some embodiments, the anti-CD33 antibody or antigen binding fragment thereof is located C-terminal to the anti-CD3 antibody or antigen binding fragment thereof within the ACE or recombinant protein (e.g., BiTE). In some embodiments, the anti-CD33 and anti-CD3 antibodies, or antigen binding fragments thereof, of the ACE or recombinant protein (e.g., BiTE) are oriented in the same direction within the ACE or recombinant protein (e.g., BiTE). For example, in some embodiments the anti-CD33 antibody or antigen binding fragment thereof is oriented from N- to C-terminus and the anti-CD3 antibody or antigen binding fragment thereof is oriented from N- to C-terminus. In such embodiments, if a linker is present, the linker is located between the C-terminus of the anti-CD33 antibody or antigen binding fragment thereof and the N-terminus of the anti-CD3 antibody or antigen binding fragment thereof. In other embodiments, wherein both the anti-CD33 and anti-CD3 antibodies, or antigen binding fragments thereof, are oriented N- to C-terminus, the linker is located between the C-terminus of the anti-CD3 antibody or antigen binding fragment thereof and the N-terminus of the anti-CD33 antibody or antigen binding fragment thereof. In other embodiments, the anti-CD33 and anti-CD3 antibodies, or antigen binding fragments thereof, of the ACE or recombinant protein (e.g., BiTE) are oriented in different directions within the ACE or recombinant protein (e.g., BiTE). For example, in some embodiments the anti-CD33 antibody or antigen binding fragment thereof is oriented from C- to N-terminus and the anti-CD3 antibody or antigen binding fragment thereof is oriented from N- to C-terminus. In other embodiments the anti-CD33 antibody or antigen binding fragment thereof is oriented from N- to C-terminus and the anti-CD3 antibody or antigen binding fragment thereof is oriented from C- to N-terminus. In such embodiments, if a linker is present, the linker is located between the N-terminus of the anti-CD33 antibody or antigen binding fragment thereof and the N-terminus of the anti-CD3 antibody or antigen binding fragment thereof. In other embodiments, wherein the anti-CD33 and anti-CD3 antibodies, or antigen binding fragments thereof, are oriented in different directions, the linker is located between the C-terminus of the anti-CD33 antibody or antigen binding fragment thereof and the C-terminus of the anti-CD3 antibody or antigen binding fragment thereof.

In some embodiments, the anti-CD33 antibody of the ACE or recombinant protein (e.g., BiTE) comprises an anti-CD33 antibody or antigen binding fragment thereof, as described herein. In some embodiments, the anti-CD33 antibody of the ACE or recombinant protein (e.g., BiTE) comprises one or more CDRs of the HL2541 antibody as described herein. In some embodiments, the anti-CD33 antibody of the ACE or recombinant protein (e.g., BiTE) comprises three light chain CDRs and three heavy chain CDRs of the HL2541 antibody as described herein. In some embodiments, the anti-CD33 antibody of the ACE or recombinant protein (e.g., BiTE) is encoded by one or more of SEQ ID NOs: 5, 7, 9, 11, 13, or 15. In some embodiments, the anti-CD33 antibody of the ACE or recombinant protein (e.g., BiTE) comprises one or more of SEQ ID NOs: 4, 6, 8, 10, 12, or 14. In some embodiments, the anti-CD33 antibody of the ACE or recombinant protein (e.g., BiTE) is encoded by all of SEQ ID NOs: 5, 7, 9, 11, 13, or 15. In some embodiments, the anti-CD33 antibody of the ACE or recombinant protein (e.g., BiTE) comprises all of SEQ ID NOs: 4, 6, 8, 10, 12, or 14. In some embodiments, the anti-CD33 antibody of the ACE or recombinant protein (e.g., BiTE) comprises a polypeptide having about 85%, 86%, 87%, 88%, 89%, 90%, 91%, 92%, 93%, 94%, 95%, 96%, 97%, 98%, or 99% sequence identity to the amino acid sequence as shown in SEQ ID NO: 21. In some embodiments, the anti-CD33 antibody of the ACE or recombinant protein (e.g., BiTE) comprises a polypeptide having no more than 37, no more than 35, no more than 30, no more than 25, no more than 20, no more than 15, no more than 10, no more than 5, or no more than 1 amino acid(s) different than (e.g., substituted, added or deleted relative to) SEQ ID NO: 21. In some embodiments, the anti-CD33 antibody of the ACE or recombinant protein (e.g., BiTE) comprises a polypeptide having the amino acid sequence as shown in SEQ ID NO: 21.

In some embodiments, the anti-CD3 antibody of the ACE or recombinant protein (e.g., BiTE) is an anti-CD3 antibody capable of inducing T cell activation. Such anti-CD3 antibodies are known in the art, and include, for example, the anti-CD3 antibody of blinatumomab (described in International Application No. PCT/US2014/046436) or as described in US Patent Pub. No. US20160317657A1. In some embodiments, the anti-CD3 antibody of the ACE or recombinant protein (e.g., BiTE) comprises a polypeptide having 85%, 86%, 87%, 88%, 89%, 90%, 91%, 92%, 93%, 94%, 95%, 96%, 97%, 98%, or 99% sequence identity to the amino acid sequence as shown in SEQ ID NO: 22. In some embodiments, the anti-CD3 antibody of the ACE or recombinant protein (e.g., BiTE) comprises a polypeptide having no more than 37, no more than 35, no more than 30, no more than 25, no more than 20, no more than 15, no more than 10, no more than 5, or no more than 1 amino acid(s) different than (e.g., substituted, added or deleted relative to) SEQ ID NO: 22. In some embodiments, the anti-CD3 antibody of the ACE or recombinant protein (e.g., BiTE) comprises a polypeptide having the amino acid sequence as shown in SEQ ID NO: 22.

In some embodiments, antibodies or antigen binding fragments of the disclosure may be modified with a therapeutic moiety (e.g., therapeutic agent). As used herein, the term "therapeutic agent" refers to chemicals or drugs or proteins that are able to inhibit cell function, inhibit cell replication or kill mammalian cells, preferably human cells. Examples of therapeutic agents include, but are not limited to, cytotoxic moieties, radioisotopes, molecules of plant, fungal, or bacterial origin (e.g., plant-derived toxins (e.g., secondary metabolites)), glycosides, antimicrobial compounds (e.g., streptomycin, penicillin, etc.), biological proteins (e.g., protein toxins), particles (e.g., recombinant viral particles, e.g., via a viral coat protein), or mixtures thereof. The therapeutic agent can be an intracellularly active drug or other agent, such as short-range radiation emitters, including, for example, short-range, high-energy alpha-emitters (e.g., 1311). In some embodiments, the therapeutic agent is Gemtuzumab Ozogamicin (GO).

Antibody Production

Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228: 1315-1317; Clackson et al. (1991) Nature, 352: 624-628; Marks et al. (1991) J. Mol. Biol., 222: 581-597WO92118619; WO 91/17271; WO 92/20791; WO 92/15679; WO 93/01288; WO 92/01047; WO 92/09690; and WO 90/02809.

In addition to the use of display libraries, the specified antigen (e.g., CD33, CD33$^{D2}$, etc.) can be used to immunize a non-human animal, e.g., a rodent, e.g., a mouse, hamster, or rat. In some embodiments, the non-human animal is a mouse. In some embodiments, the non-human animal is a guinea pig.

In another embodiment, a monoclonal antibody is obtained from the non-human animal, and then modified, e.g., made chimeric, using recombinant DNA techniques known in the art. A variety of approaches for making chimeric antibodies have been described. See e.g., Morrison et al., Proc. Natl. Acad. Sci U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

Antibodies can also be humanized by methods known in the art. For example, monoclonal antibodies with a desired binding specificity can be commercially humanized (Scotgene, Scotland; and Oxford Molecular, Palo Alto, Calif.). Fully humanized antibodies, such as those expressed in transgenic animals, are within the scope of the invention (see, e.g., Green et al. (1994) Nature Genetics 7, 13; and U.S. Pat. Nos. 5,545,806 and 5,569,825).

For additional antibody production techniques, see Antibodies: A Laboratory Manual, Second Edition. Edited by Edward A. Greenfield, Dana-Farber Cancer Institute, ©2014. The present disclosure is not necessarily limited to any particular source, method of production, or other special characteristics of an antibody.

Some aspects of the present invention relate to isolated cells (e.g., host cells) transformed with a polynucleotide or vector. Host cells may be prokaryotic or eukaryotic cells. The polynucleotide or vector which is present in the host cell may either be integrated into the genome of the host cell, or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as HEK293 and CHO cells. Depending upon the host employed in a recombinant production procedure, the antibodies or immunoglobulin chains encoded by the polynucleotide may be glycosylated or may be non-glycosylated.

Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, e.g., Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large-scale production of the antibody or antibody fragments.

The transformed host cells can be grown in fermenters and cultured according to techniques known in the art to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, e.g., Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially-expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As used herein, a "hybridoma cell" refers to an immortalized cell derived from the fusion of B lymphoblasts with a myeloma fusion partner. For preparing monoclonal antibody-producing cells (e.g., hybridoma cells), an individual animal whose antibody titer has been confirmed (e.g., a mouse) is selected, and, 2 days to 5 days after the final immunization, its spleen or lymph node is harvested and the antibody-producing cells contained therein are fused with myeloma cells to prepare the desired monoclonal antibody producer hybridoma. Measurement of the antibody titer in antiserum can be carried out, for example, by reacting the labeled protein, as described hereinafter, and antiserum, and then measuring the activity of the labeling agent bound to the antibody. The cell fusion can be carried out according to known methods, for example, the method described by Kochler and Milstein (Nature 256:495 (1975)). As a fusion promoter, for example, polyethylene glycol (PEG) or Sendai virus (HVJ), preferably PEG, is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C., for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate), to which antibody is adsorbed directly or together with a carrier, and then an anti-immunoglobulin antibody (e.g., if mouse cells are used in cell fusion, anti-mouse immunoglobulin antibody is used) or Protein A labeled with a radioactive substance, or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance, or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20%, fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C., for about 5 days to 3 weeks, preferably 1 week to 2 weeks, under about 5% $CO_2$ gas. The antibody titer of the supernatant of a hybridoma culture can be measured according to the same manner as described above with respect to the antibody titer of the anti-protein in the antiserum.

As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vector which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA, synthetically-produced DNA or RNA, or a recombinantly-produced chimeric nucleic acid molecule comprising any of those polynucleotides either alone or in combination. In some embodiments, a polynucleotide is part of a vector. Such vectors may comprise further genes, such as marker genes, which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription, and, optionally, poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in E. coli, and examples of regulatory elements permitting expression in eukaryotic host cells are the AOX1 or GAL1 promoter in yeast, or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription, such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and are well known in the art. The leader sequence(s) is (are) assembled in appropriate phase with translation, initiation and termination sequences, and, preferably, a leader sequence capable of directing secretion of translated protein, or a portion thereof, into, for example, the extracellular medium. Optionally, a heterologous polynucleotide sequence can be used that encodes a fusion protein, including a C- or N-terminal identification peptide, imparting desired characteristics, e.g., stabilization or simplified purification of expressed recombinant product.

In some embodiments, polynucleotides encoding at least the variable domain of the light and/or heavy chain may encode the variable domains of both immunoglobulin chains, or only one. Likewise, a polynucleotide may be under the control of the same promoter or may be separately controlled for expression. Furthermore, some aspects relate to vectors, particularly plasmids, cosmids, viruses and bacteriophages used conventionally in genetic engineering, that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses, such as retroviruses, vaccinia virus, adeno-associated virus, herpes viruses, or bovine papilloma virus, may be used for delivery of the polynucleotide or vector into targeted cell populations (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain (s) of the immunoglobulin chain encoding sequences and expression control sequences) can be transferred into the host cell by suitable methods, which vary depending on the type of cellular host.

Compositions

In some aspects, the disclosure relates to pharmaceutical compositions comprising anti-CD33 antibodies (e.g., anti-CD33$^{D2}$ antibodies), ACEs (as described herein), or recombinant proteins (e.g., BiTEs, as described herein). In some embodiments, the composition comprises an anti-CD33 antibody (e.g., anti-CD33$^{D2}$ antibody), an ACE, or a recombinant protein, and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

Typically, pharmaceutical compositions are formulated for delivering an effective amount of an agent (e.g., an anti-CD33 antibody, such as an anti-CD33$^{D2}$ antibody, an ACE, or a recombinant protein (e.g., BiTEs)). In general, an "effective amount" of an active agent refers to an amount sufficient to elicit the desired biological response (e.g., killing of a cancerous cell or suppression of tumor growth). An effective amount of an agent may vary depending on such factors as the desired biological endpoint, the pharmacokinetics of the compound, the disease being treated (e.g., certain cancers characterized by surface expression of CD33), the mode of administration, and the patient.

A composition is said to be a "pharmaceutically acceptable carrier" if its administration can be tolerated by a recipient patient. Sterile phosphate-buffered saline (PBS) is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed, and which is inert with respect to the active agent, may be utilized for preparing and administering the pharmaceutical compositions of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

An effective amount, also referred to as a therapeutically effective amount, of a compound (for example, an anti-CD33$^{D2}$ antibody, an ACE, or a recombinant protein) is an amount sufficient to ameliorate at least one adverse effect associated with cancer (e.g., tumor growth, metastasis). The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and selected mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

Treatment

Aspects of the disclosure relate to methods and compositions for treating subjects having certain cancers, such as CD33+ cancers. To "treat" a disease or disorder, as the term is used herein, means to prevent, or reduce the frequency or severity of, at least one sign or symptom of a disease or disorder (e.g. a cancer) experienced by a subject. As used herein, "treating cancer" refers to decreasing the number of cancer cells in a subject, preventing or slowing the growth of cancer cells in a subject, and/or preventing or reducing the metastasis of cancer cells in a subject, and includes any type of response for either relieving cancer symptoms or increasing the life-span of a subject. In some embodiments, the cancer is a leukemia or a lymphoma. In some embodiments, the leukemia is acute myeloid leukemia (AML).

In some aspects, the disclosure provides a method for treating cancer, the method comprising administering to a subject having cancer an effective amount an antibody, ACE, recombinant protein, or composition as described by the disclosure (e.g., an anti-CD33 antibody, an ACE, or a recombinant protein (e.g., BiTE), or a composition comprising an anti-CD33 antibody, ACE, or recombinant protein (e.g., BiTE)).

A "subject" refers to a mammal, such as a human, a nonhuman primate, a dog, a cat, a sheep, a horse, a cow, a pig or a goat. In an important embodiment, the mammal is a human. The subject as used herein can be an adult subject or a pediatric subject.

Gemtuzumab Ozogamicin (GO) recognizes an epitope present in exon 2 of CD33. Thus, patients expressing a variant T (CT and TT) allele at splicing SNP rs12459419, which results in expression of a CD33 variant lacking an IgV domain (CD33$^{D2}$), show no clinical benefit from GO, whereas the patients with CC genotype demonstrate significant reduction in relapse risk and improved survival when given GO. The reliance of current CD33-directed immunotherapies on binding to the IgV domain necessitates the development of alternative strategies for patients expressing the CD33$^{D2}$ isoform. Thus, aspects of the disclosure relate to anti-CD33 antibodies, ACEs, and recombinant proteins (e.g., BiTE) that are considered likely to benefit those subjects expressing CD33$^{D2}$ isoform. In some embodiments, a subject is considered likely to benefit from treatment with an anti-CD33$^{D2}$ antibody, ACE, or recombinant protein (e.g., BiTE) if the subject exhibits a genotype of CC for the CD33 SNP rs12459419. In some embodiments, a subject is considered likely to benefit from treatment with an agent that selectively binds to CD33, such as an anti-CD33$^{D2}$ antibody, ACE, or recombinant protein (e.g., BiTE) as described herein, if the subject exhibits a genotype of CC for the CD33 SNP rs12459419. Accordingly, in some embodiments, an agent that selectively binds to CD33, such as an anti-CD33$^{D2}$ antibody, ACE, or recombinant protein (e.g., BiTE), as described herein, is administered to a subject who exhibits a genotype of CC for the CD33 SNP rs12459419.

In some embodiments, a subject is treated with an effective amount of an anti-CD33 (e.g., anti-CD33$^{D2}$) antibody, ACE, or recombinant protein (e.g., BiTE) described herein. An "effective amount" of an agent generally refers to an amount sufficient to elicit the desired biological response, i.e., treat the condition. As will be appreciated by those of ordinary skill in this art, the effective amount of an agent described herein may vary depending on such factors as the condition being treated, the mode of administration, the therapy, if any, with which it is combined, and the age and health of the subject.

Generally, antibodies and pharmaceutical compositions of the disclosure preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally.

The pharmaceutical compositions containing an anti-CD33 antibody, ACE, or recombinant protein (e.g., BiTE), and/or other compounds, can be administered by any suitable route for administering medications. A variety of administration routes are available. The particular mode selected will depend, of course, upon the particular agent or agents selected, the particular condition being treated, and the dosage required for therapeutic efficacy. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the anti-CD33 antibody, ACE, or recombinant protein (e.g., BiTE), and/or other therapeutic agent, can be administered to a subject by any mode that delivers the agent to the desired surface, e.g., mucosal, systemic.

EXAMPLES

Example 1

Cell Lines, Antibodies and Other Reagents

The CD33-murine pro-B cell Ba/F3 cell line was cultured in RPMI-1640 with 10% fetal bovine serum, 1% L-Glutamine, 1% Penicillin-Streptomycin, and 10 ng/mL of recombinant mouse IL3. The human AML cell lines HL-60, K562, Molm13, and MV4; 11 were cultured IMDM or RPMI-1640 medium and supplemented 10% FBS. THP-1 cells were cultured in RPMI 1640 supplemented with 10% FBS and 0.05 mM βME; and Kasumi-1 cells were cultured in IMDM supplemented with 20% FBS. HEK293T17 and HEK293T cells used to generate viral titers for transduction were cultured in DMEM supplemented with 10% FBS and 1% Penicillin-Streptomycin.

Generation of Ba/F3 Cell Lines Stably Overexpressing CD33 Isoforms

Low passage HEK293T17 cells were thawed and were grown to approximately 70% confluency. Afterward, cells were transfected with the following plasmids: pMX-CD33$^{FL}$, pMX-CD33$^{D2}$, pMX-CD33$^{FL}$GFP, or pMX-CD33$^{D2}$ GFP, as well as the pEcoPak murine ecotropic retroviral helper. Cells were returned to the incubator for 48 hours, after which supernatants containing viral particles were collected and passed through 0.45 μm sterile filters. The filtered supernatant was then used for transduction at a ratio of 1 mL to 2×10$^6$ Ba/F3 cells to create the following CD33$^{FL}$ or CD33$^{D2}$ overexpressing Ba/F3 cell lines: Ba/F3-CD33$^{FL}$ (pMX-CD33$^{FL}$), Ba/F3-CD33$^{D2}$ (pMX-CD33$^{D2}$), Ba/F3-CD33$^{FL}$GFP (pMX-CD33$^{FL}$GFP), Ba/F3-CD33$^{D2}$ (pMX-CD33$^{D2}$ GFP).

Antibodies

The following antibodies were used in this work: mouse unconjugated and PE-conjugated IgG1 anti-CD33 mAb (clone P67.6), mouse purified IgG$_1$ anti-CD33 mAb (clone E6), mouse Pacific Blue-conjugated IgG$_2$a anti-CD14 mAb (clone M5E2), mouse APC-conjugated IgG$_2$a anti-CD34 mAb (clone 561), mouse Super Bright 600-conjugated IgG$_1$ anti-CD45 mAb (clone 2D1), mouse FITC-conjugated anti-CD14 mAb (clone MφP9), mouse APC-conjugated anti-CD34 mAb (8G12), mouse PerCP conjugated anti-CD45 mAb (clone 2D1), rabbit anti-H3 Histone, and Alexa Fluor® 647-conjugated goat anti-mouse IgG H&L.

The HL2541 (IgG$_1$) antibody was generated using a keyhole limpet hemocyanin-conjugated peptide (PRPQDHGTNLTCQVKFAGAG; amino acid residues 201-220; SEQ ID NO: 3) mapped to the shared IgC domain of CD33 as an immunogen and the standard conventional immunization method for antibody development. Briefly, female BALB/c mice 6-9 weeks old were immunized every 3 weeks for nine weeks total. After immunization, hybridoma clones were generated after fusing the spleen cells with Sp2/0 murine myeloma cells. Hybridoma clone supernatants were subsequently screened by flow cytometry and ELISA assays to confirm binding of CD33 by the antibodies within. The clone that produced supernatant with strongest CD33 binding antibodies (by median fluorescence intensity (MFI)) was expanded and utilized to produce HL2541 mAb which was purified by affinity chromatography.

Immunoblotting

Cell pellets containing either at least 5×10$^6$ cells (cell lines) or at least 7×10$^5$ cells (primary samples) were washed thrice in PBS and lysed in RIPA lysis buffer (25 mM Tris-HCl pH 7.6, 150 mM NaCl, 1% NP-40, 1% sodium deoxycholate, 0.1% SDS) supplemented with protease inhibitor cocktail on ice. Lysates were cleared by centrifuging at ~18,000×g for 15 mins. A Bradford assay was used to estimate protein concentrations using diluted lysates. Where indicated, PNGase F treatment was performed. Untreated and/or treated samples dissolved in NuPAGE LDS buffer were heated at 70° C. for 10 minutes prior to separation by NuPAGE 10% Bis-Tris gels. Proteins were transferred to PVDF membranes using an iBlot dry blotting system. Membranes were blocked in 4% BSA in 0.2% PBS-Tween (PBS-T) and probed with specified antibodies overnight at 4° C. Stained membranes were washed thrice in 0.2% PBS-T and probed with IRDye 800CW goat anti-mouse and IRDye 680RD or IRDye 800 goat anti-rabbit fluorescent secondary antibodies. Imaging was performed using the LI-COR Odyssey CLx system.

Flow Cytometry

For cell staining, approximately $0.5-1\times10^6$ cells were harvested from culture and washed twice with staining buffer (2% PBS/FBS containing 0.05% $NaN_3$). Cells were then stained with LIVE/DEAD NIR viability dye for 30 min at room temperature (RT). After washing with staining buffer, cells were blocked for 5 minutes at RT using Human TruStain FcX and True-Stain Monocyte Blocker and stained with the respective antibodies for 30 minutes at RT. Cells were then washed with the staining buffer and fixed using the Foxp3 Transcription Factor Staining Buffer set before flow cytometry data acquisition and analysis. Cryopreserved primary AML patient samples were first rapidly thawed at 37° C. and then stained. Data acquisition was performed on Cytek Aurora™ platform and data analysis was done using FCS Express 7.

Immunofluorescence Microscopy

Approximately $1\times10^6$ cells were harvested from culture and washed with 1% BSA/PBS, fixed using a 3.7% formaldehyde solution, and blocked with 1% BSA/PBS for 30 minutes at room temperature followed by staining with the specified antibody overnight at 40° C. Afterward, the cells were washed with 1% BSA/PBS and stained with Alexa Fluor® 647-conjugated goat anti-mouse IgG H&L for one hour at RT. Following secondary antibody incubation, cells were washed and incubated with 1 µg/mL DAPI for 5 minutes at room temperature in the dark followed by a final wash using 1×PBS. Samples were then placed on poly-L-lysine coated slides, mounted with coverslips using VECTASHIELD Antifade Mounting Medium, and examined using the Olympus IX81-DSU motorized spinning disk confocal microscope. All images acquired represent several Z-stack optical sections at 0.02-0.03 mm intervals obtained through a 20× objective. The ImageJ platform was used for analysis and the RGB Profiler plug-in therein was used to observe the co-localization of color intensities. The antibody dilutions and amounts used in these experiments can be found in Tables 3-6.

Primary Patient Specimens

Primary leukemic cells from patients of different rs12459419 genotypes enrolled in the AAML0531 clinical trial were obtained and used for this study. Bone marrow aspirates were extracted at diagnosis and PBMCs were isolated from the samples via Ficoll-paque density gradient separation. Samples were subsequently cryopreserved in liquid nitrogen until their use. Regenerating bone marrow specimens from individuals with a history of leukemia were also obtained and used to profile regenerating monocytes for this study. The specimens were extracted, isolated, and preserved as described above.

Figure 1B:
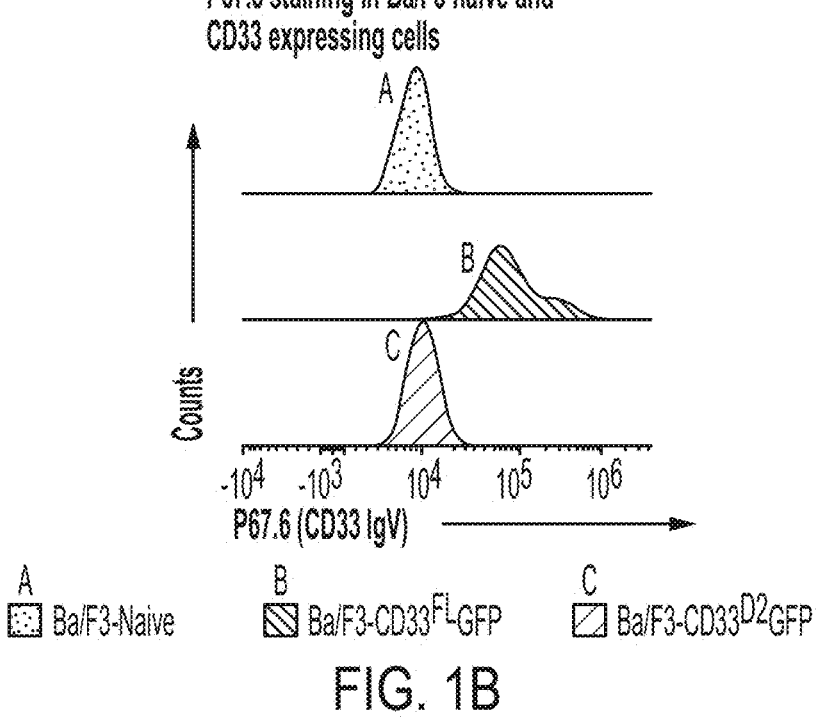
Figures 5A, 5B:
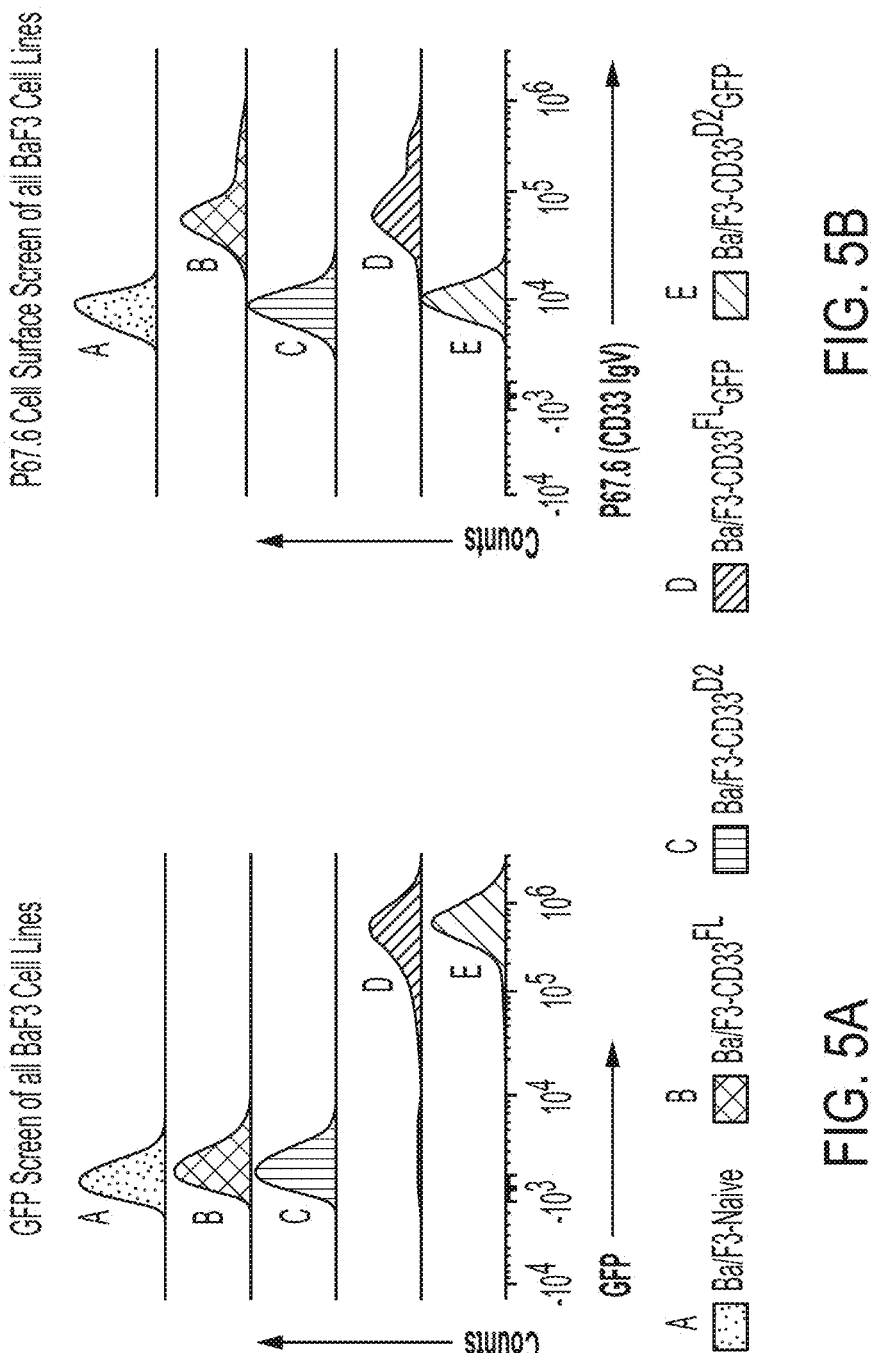
FIGS. 5A-5B show characterization of the BaF3 cell line system.

Novel IgC Specific CD33 Antibodies Recognize CD33$^{D2}$ and not CD33$^{FL}$ on Cell Surface Ba/F3 cells stably expressing CD33$^{FL}$, CD33$^{D2}$, and their respective GFP fusion proteins were utilized as a system to test the new antibodies described herein. To confirm the expression of CD33 in the correct confirmation, a screen using flow cytometry for CD33 and GFP (where applicable) was performed. As expected, Ba/F3-Naïve cells showed no GFP fluorescence signal whereas Ba/F3-CD33$^{FL}$GFP and Ba/F3-CD33$^{D2}$ GFP transduced cells were positive for GFP confirming CD33 expression (FIG. 1A). When stained with the IgV domain-directed P67.6 antibody, only Ba/F3-CD33$^{FL}$ GFP showed a positive signal whereas Ba/F3-Naïve and Ba/F3-CD33$^{D2}$GFP were negative (FIG. 1B). Screening of Ba/F3 cell lines engineered to express CD33$^{FL}$ and CD33$^{D2}$ without GFP produced similar results indicating no alteration in protein recognition resulting from overexpression of CD33 as a GFP fusion protein (FIGS. 5A-5B).

Figure 7:
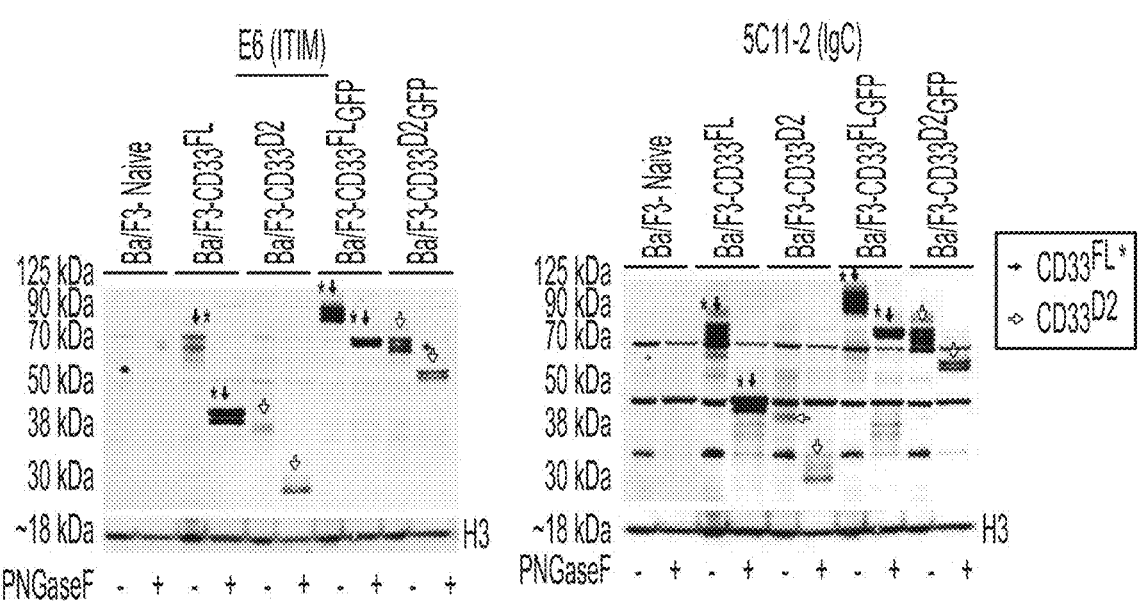
FIG. 7 shows data indicating that 5C11-2 recognizes CD33. Recognition of CD33 is confirmed by Western blotting analysis of engineered BaF3 cells using anti-CD33 mAbs E1 (1:100) and HL2541 (1:250).

Subsequently, the top two promising hybridoma clonal populations, selected based on an initial screening of supernatants from the hybridoma using the same CD33 overexpression system were used to mass-produce the new CD33 IgC domain-directed antibodies HL2541 and 5C11-2. The epitopes targeted by both antibodies are displayed within FIG. 6. Western blotting using Ba/F3 cell lines expressing CD33$^{FL}$ or CD33$^{D2}$ isoforms confirmed recognition of both isoforms by HL2541 and 5C11-2. These results were concordant with the corresponding results using commercially available E6, an ITIM directed anti-CD33 mAb that recognizes both isoforms. FIG. 1C shows protein bands corresponding to at ~67 kDa and ~40-42 kDa for the glycosylated and unglycosylated forms for CD33$^{FL}$, respectively, and ~38 kDa and ~33 kDa for glycosylated and unglycosylated forms of CD33$^{D2}$, respectively, using the E6 and HL2541 mAbs. CD33$^{FL}$-GFP and CD33$^{D2}$-GFP fusion proteins were similarly recognized with a corresponding increase of ~27 kDa respectively. 5C11-2 showed similar results, though some secondary bands were observed (FIG. 7).

Figure 1D:
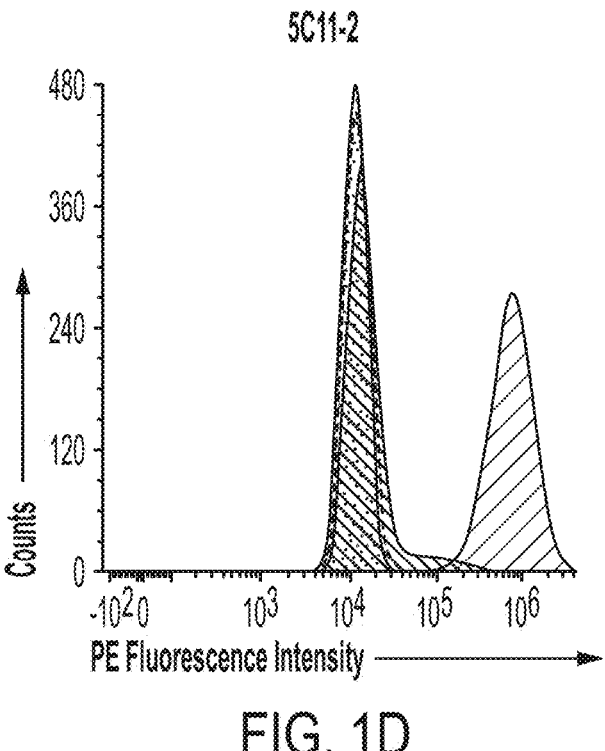
Figure 1E:
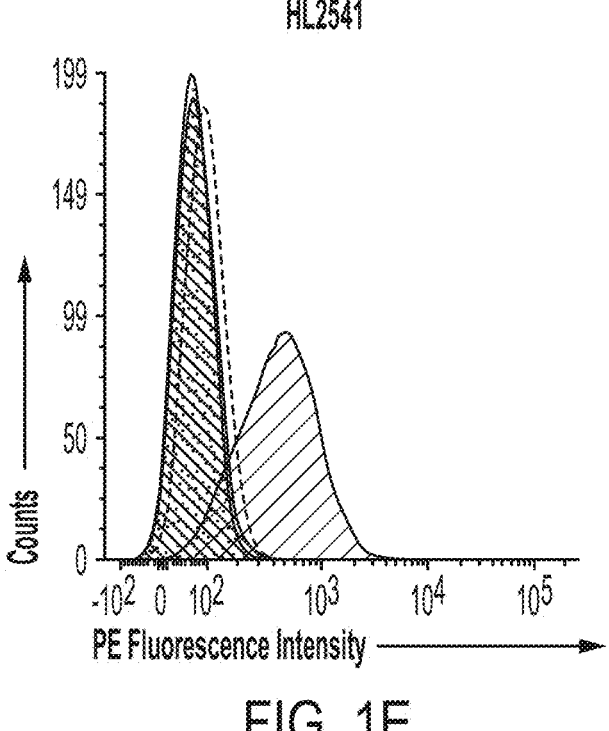
Figure 1F:
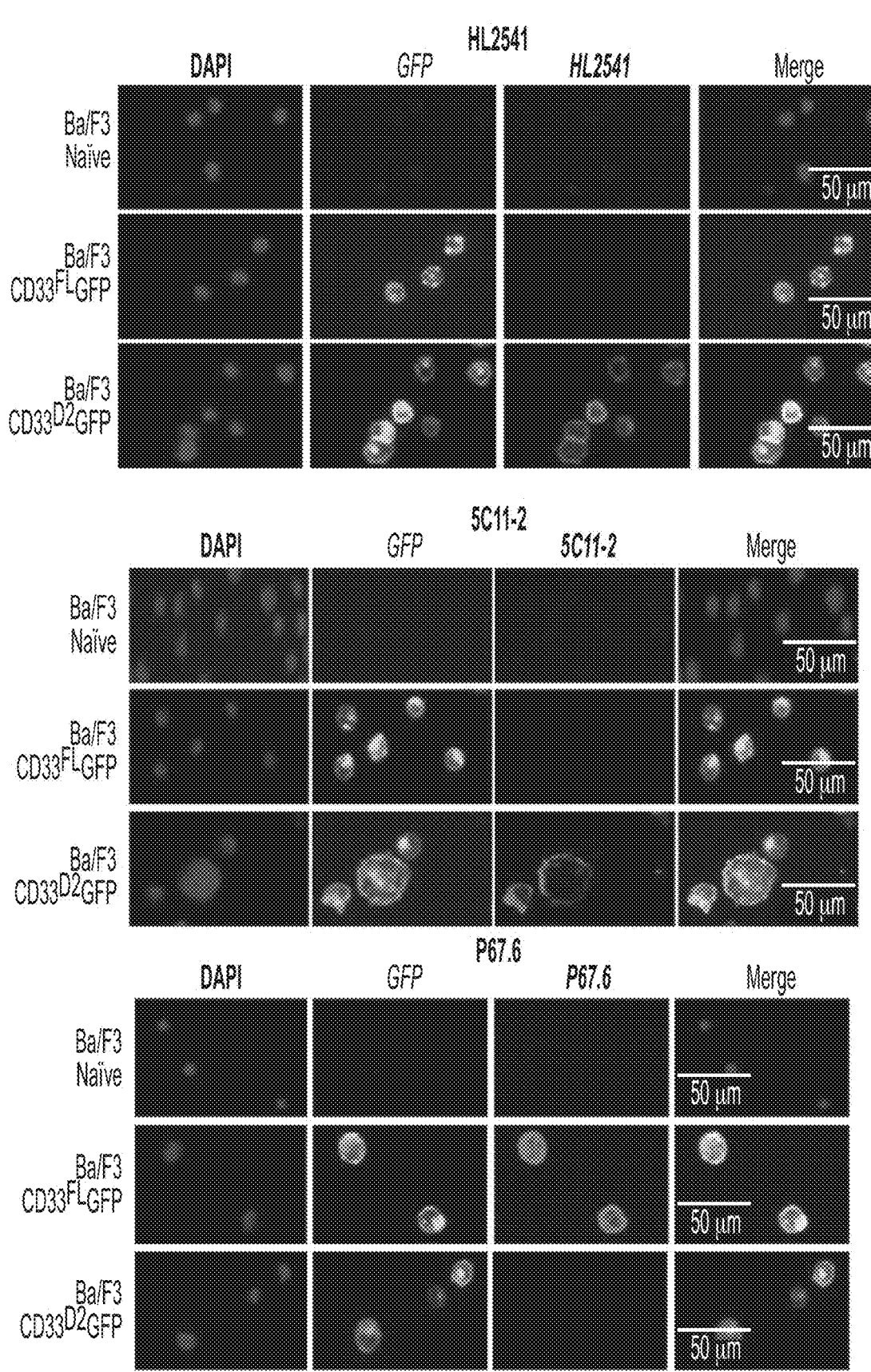
Figure 8:
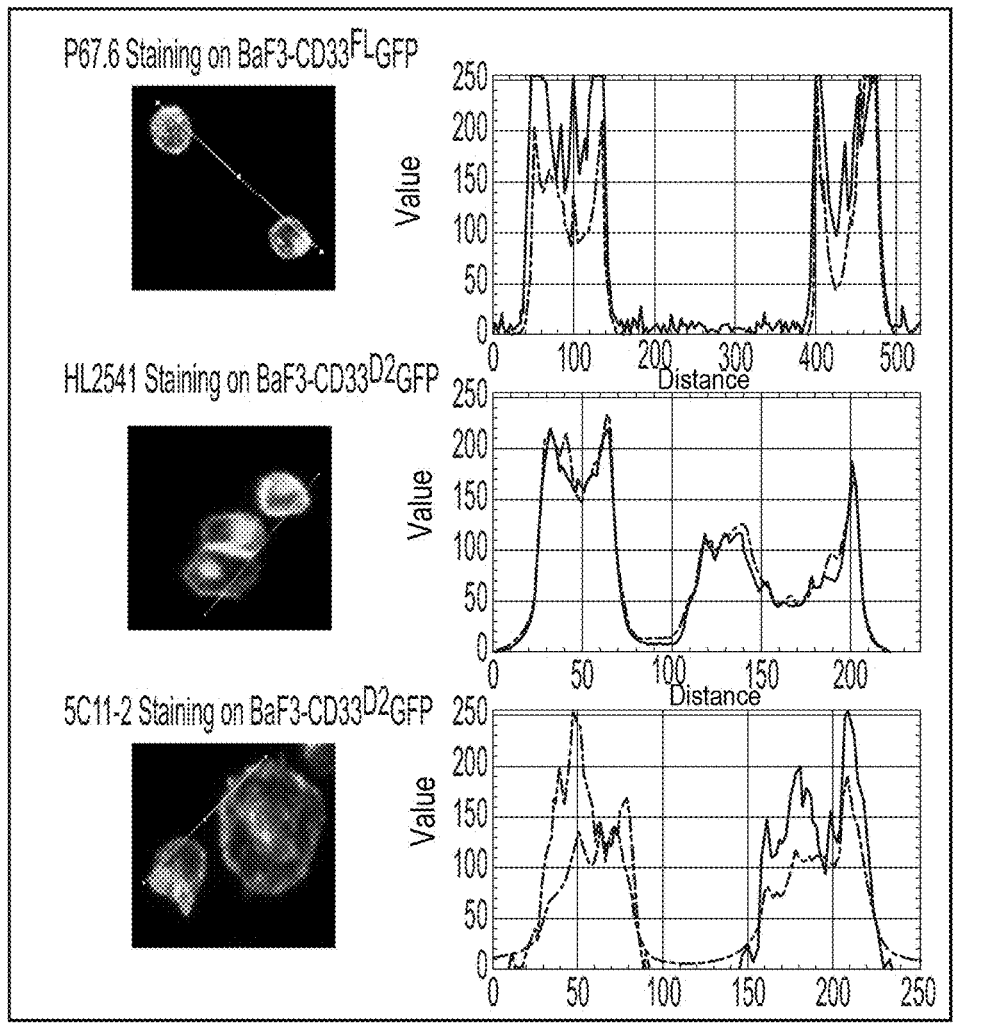
FIG. 8 shows RGB profiler data confirming recognition of CD33$^{D2}$ by P67.6, HL2541, and 5C11-2.

Interestingly, in flow cytometry assays, both HL2541 and 5C11-2 recognized CD33$^{D2}$ on the surface Ba/F3-CD33$^{D2}$ GFP cells, but displayed no recognition of CD33$^{FL}$ on the surface Ba/F3-CD33$^{FL}$ GFP cells (FIGS. 1D and 1E). These results were confirmed by confocal microscopy, where HL2541 and 5C11-2 only recognized CD33$^{D2}$ on the surface Ba/F3-CD33$^{D2}$ GFP cells while P67.6 only recognized CD33$^{FL}$ on the surface Ba/F3-CD33$^{FL}$GFP cells (FIG. 1F). Co-localization of GFP and antibody signals were also confirmed using the RGB profiler module in Image J (FIG. 8). Altogether, these results confirm suitability and specificity of 5C11-2 and HL2541 as IgC-directed novel CD33 mAbs for detection of CD33$^{D2}$ and CD33$^{FL}$ in western blotting and CD33$^{D2}$ in immunofluorescence assays.

Evaluation of Antibodies for the Screening of CD33$^{FL}$ and CD33$^{D2}$ Isoforms in AML Cell Lines Endogenous CD33 cell surface expression was assessed in AML cell lines representative of different rs12459419 genotypes including Molm-13 (CC), HL-60 (CC), MV4; 11 (CT), and K562 (TT), using P67.6 and the newly-developed IgC domain-directed antibodies HL2541 and 5C11-2 (FIG. 2A) (described herein). As anticipated, P67.6 revealed higher cell surface expression of CD33$^{FL}$ in homozygous dominant (CC: Molm-13 and HL-60) and heterozygous (CT: MV4; 11) cell lines in comparison to the homozygous recessive cell line (TT: K562). Staining with 5C11-2, CD33$^{D2}$ was not recognized on the cell surface of any AML cell line irrespective of rs12459419 genotype. Staining with HL2541, which is targeted to a different epitope within the IgC domain, a positive shift was observed for the MV4; 11 and K562 cell lines.

Figures 2A, 2B:
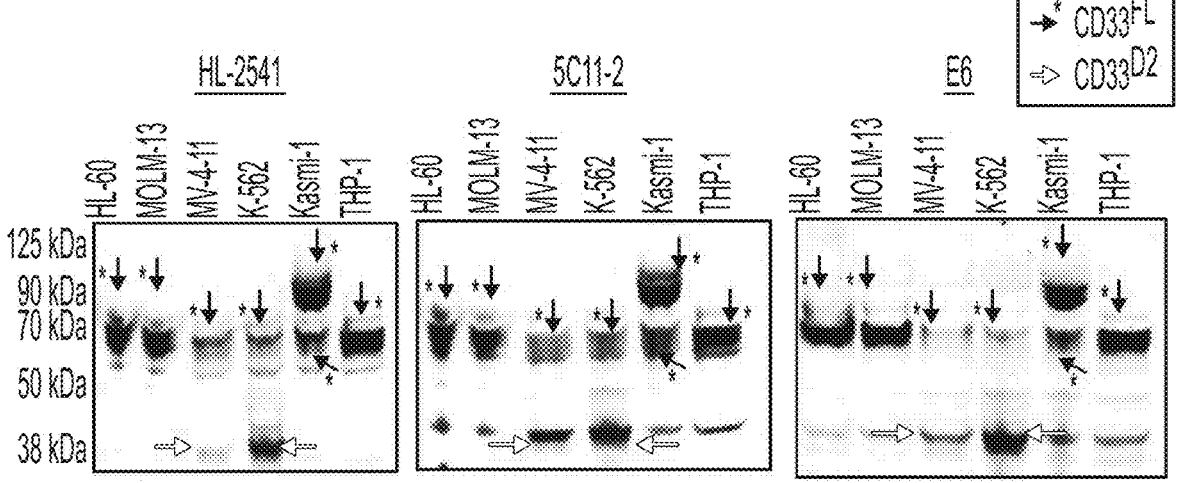
FIGS. 2A-2C show CD33 Screening in AML Cell Lines.
Figure 2C:
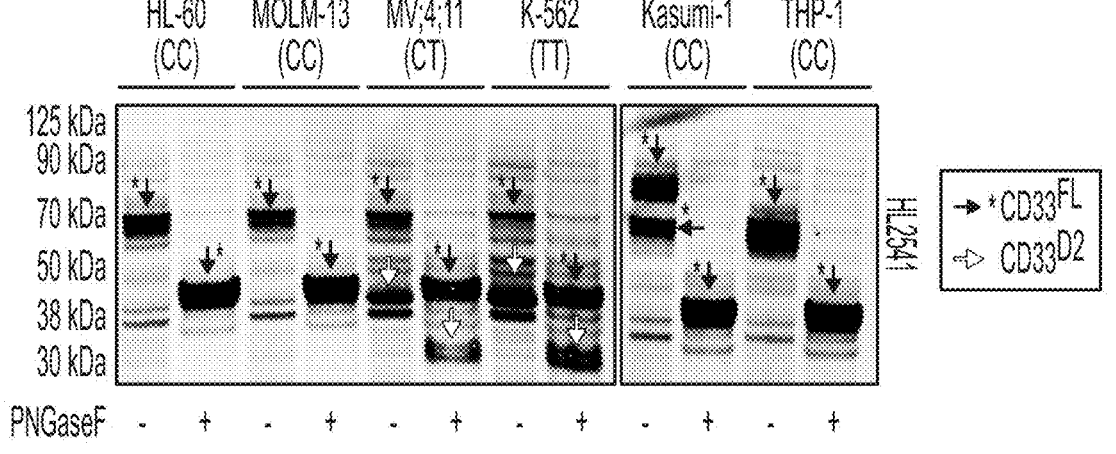

Western blotting of AML cell lines using the E6, HL2541, and 5C11-2 antibodies demonstrated robust recognition of CD33$^{FL}$ at ~67 kDa in all cell lines regardless of rs12459419 genotype. However, CD33$^{D2}$ recognition at ~40 kDa was correlated with rs12459419 genotype where the Molm-13 and HL-60 cell lines displayed minimal expression of CD33$^{D2}$. Higher levels were detected in MV4; 11 and K562 cell lines using all three antibodies (FIG. 2B). Western blots of PNGase-treated and -untreated AML cell lines using HL2541 also showed genotype-dependent expression of CD33 isoforms with recognition of unglycosylated CD33$^{FL}$ and CD33$^{D2}$ at ~40 kDa and ~33 kDa, as previously seen (FIG. 2C). Of note, no additional protein bands were observed when probing with HL2541 in either the MV4; 11 or K562 cell lines, consistent with the results observed in flow cytometry assays using HL2541.

Evaluation of Antibodies in Primary AML Bone Marrow Specimens of Different rs12459419 Genotypes Primary bone marrow specimens from AML patients with different rs12459419 genotypes were profiled for CD33$^{D2}$ expression using P67.6 and the new antibodies of the disclosure. Overall, no significant differences in patient demographics, including age, race, and AML phenotypic characteristics, were observed across rs12459419 genotypes (Table 3).

In addition to primary AML bone marrow specimens, regenerating monocytes from bone marrow specimens obtained at remission from patients initially diagnosed with leukemia were also evaluated using P67.6, HL2541, and 5C11-2. The cells were stained for CD34, CD14, and CD45, as previously described, and individual cell populations including CD14⁻CD45$^{dim}$CD34⁺ progenitor cells and CD14⁺ mature monocytes were gated out. In addition, lymphoblastic progenitors were separated from myeloblastic progenitor cells using CD34 and size, based on right-angle scatter properties (FIG. 4A). Staining with P67.6, both myeloblastic CD14⁻CD45$^{dim}$CD34⁺ progenitor cells and CD14⁺ monocytes were positive for CD33$^{FL}$ cell surface

TABLE 3

Patient demographics for rs12459419 genotype.

| | rs12459419 genotype | | | | | | | |
|---|---|---|---|---|---|---|---|---|
| | CC (n = 5)* | | CT (n = 5) | | TT (n = 4)* | | Total (n = 14) | |
| Patient Characteristics | No. | % | No. | % | No. | % | No. | % |
| Sex (Female) | 2 | 50.0% | 2 | 40.0% | 3 | 60.0% | 7 | 50.0% |
| Age (years, median) | 11.4 | | 13.6 | | 2.0 | | 11.8 | |
| Age (Range) | (8.7-16.0) | | (11.5-17.3) | | (1.7-16.2) | | (1.6-17.3) | |
| Race (White) | 4 | 100.0% | 4 | 80.0% | 4 | 66.7% | 12 | 92.3% |
| Race (Unknown) | 0 | 0.0% | 1 | 20.0% | 1 | 16.7% | 2 | 15.4% |
| Risk Group (High) | 0 | 0.0% | 0 | 0.0% | 0 | 0.0% | 0 | 0.0% |
| Risk Group (Standard) | 0 | 0.0% | 2 | 40.0% | 3 | 60.0% | 5 | 35.7% |
| Risk Group (Low) | 4 | 100.0% | 3 | 60.0% | 2 | 40.0% | 9 | 64.3% |
| Clinical features (BM Blast %, median) | 61 | | 65* | | 81 | | 80 | |
| Clinical features (range) | (36-90) | | (49-80) | | (25-90) | | (25-90) | |

*One patient sample with unavailable demographics data

Figure 3A:
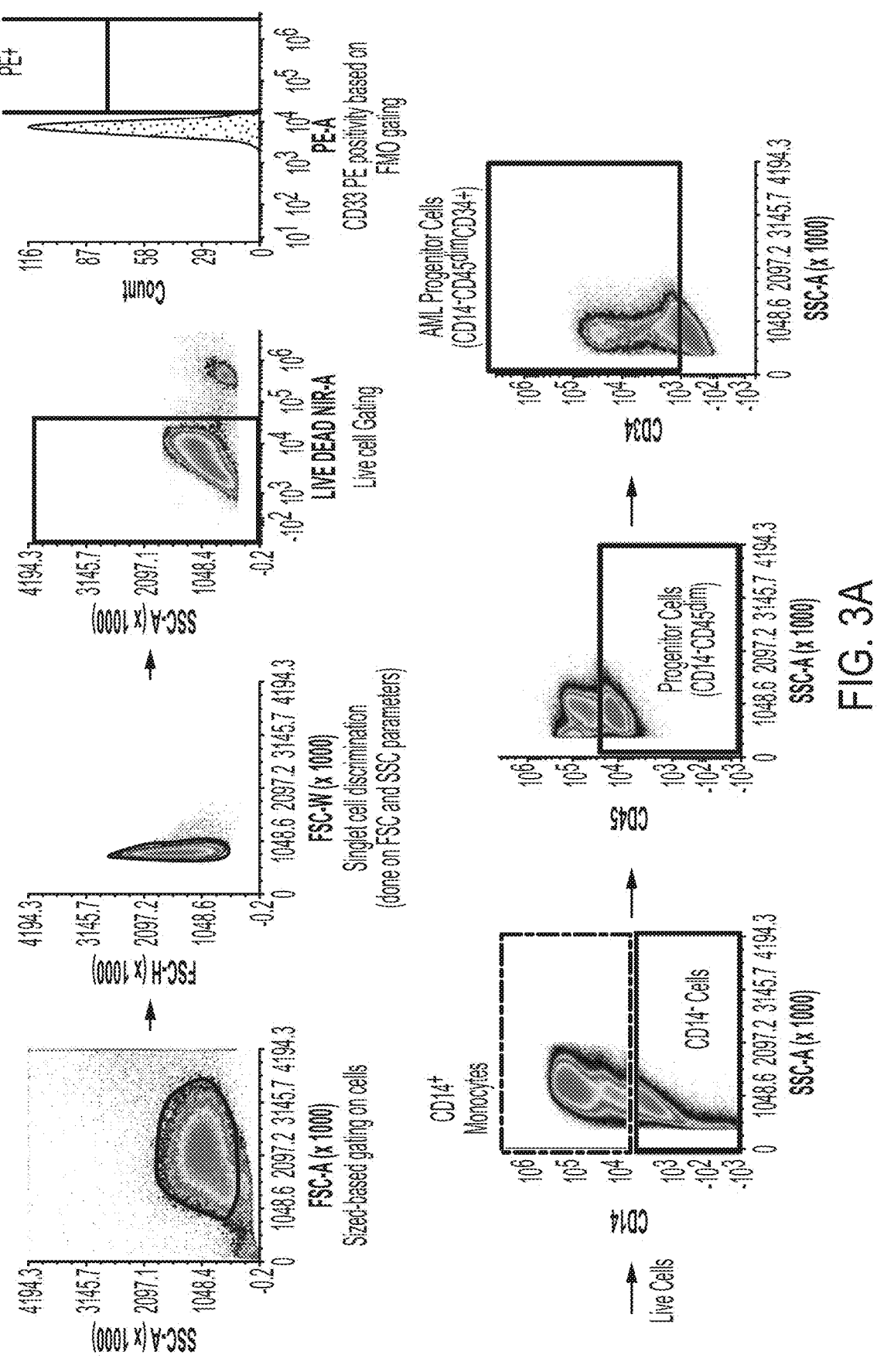
FIGS. 3A-3C show profiling of CD33$^{D2}$ Cell Surface Expression on primary AML cells obtained at diagnosis.
Figure 3B:
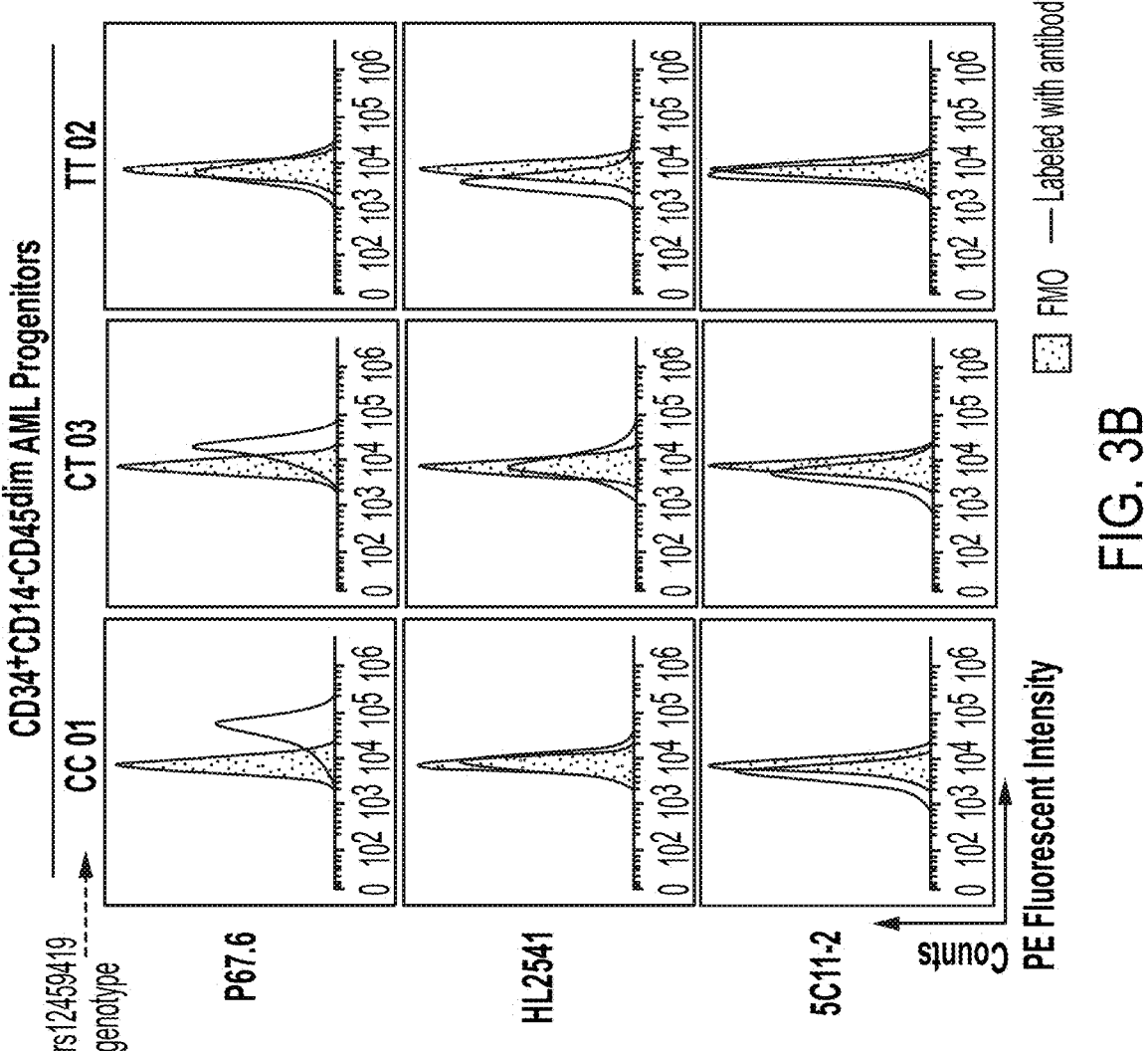
Figure 3C:
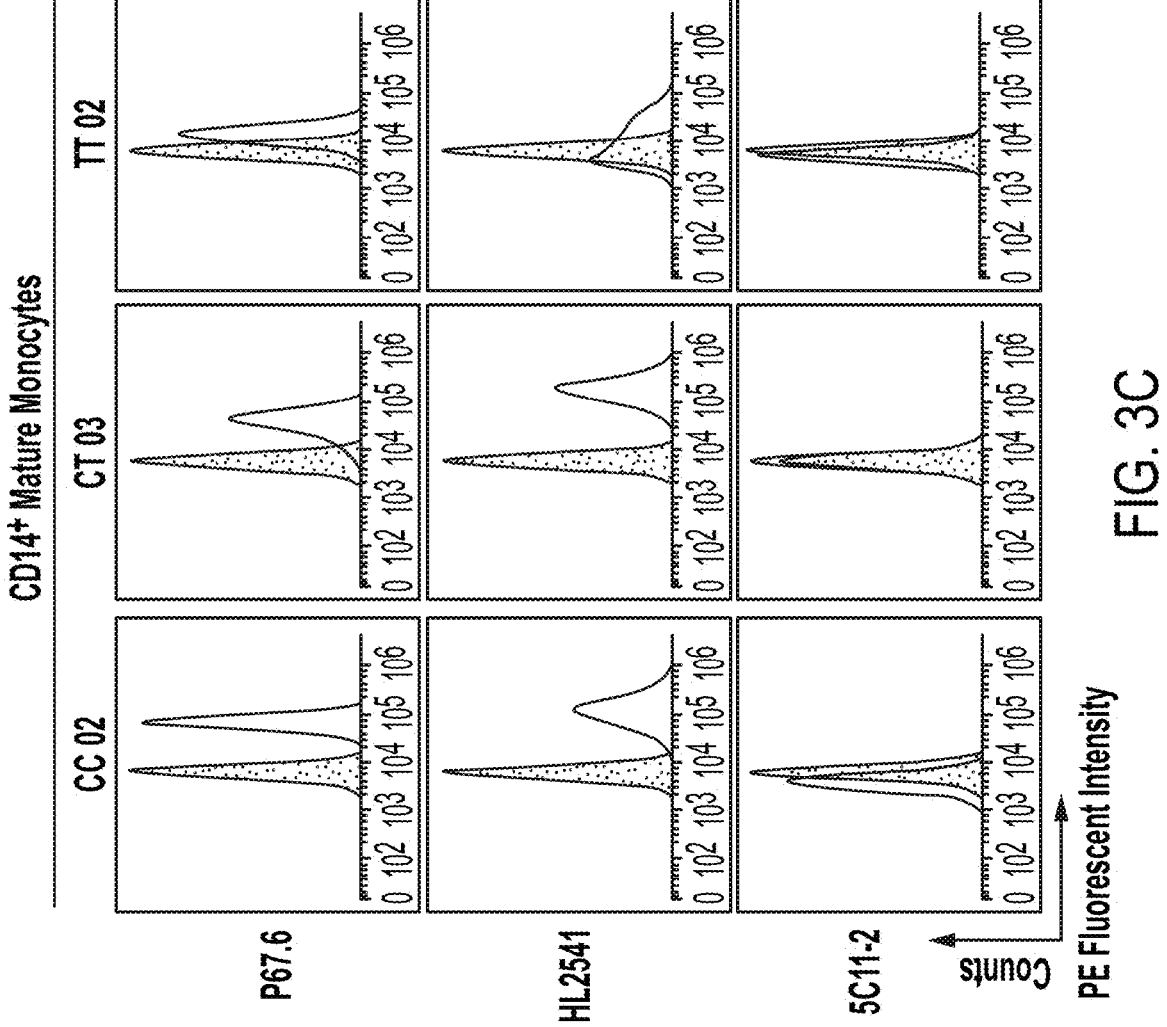
Figure 9A:
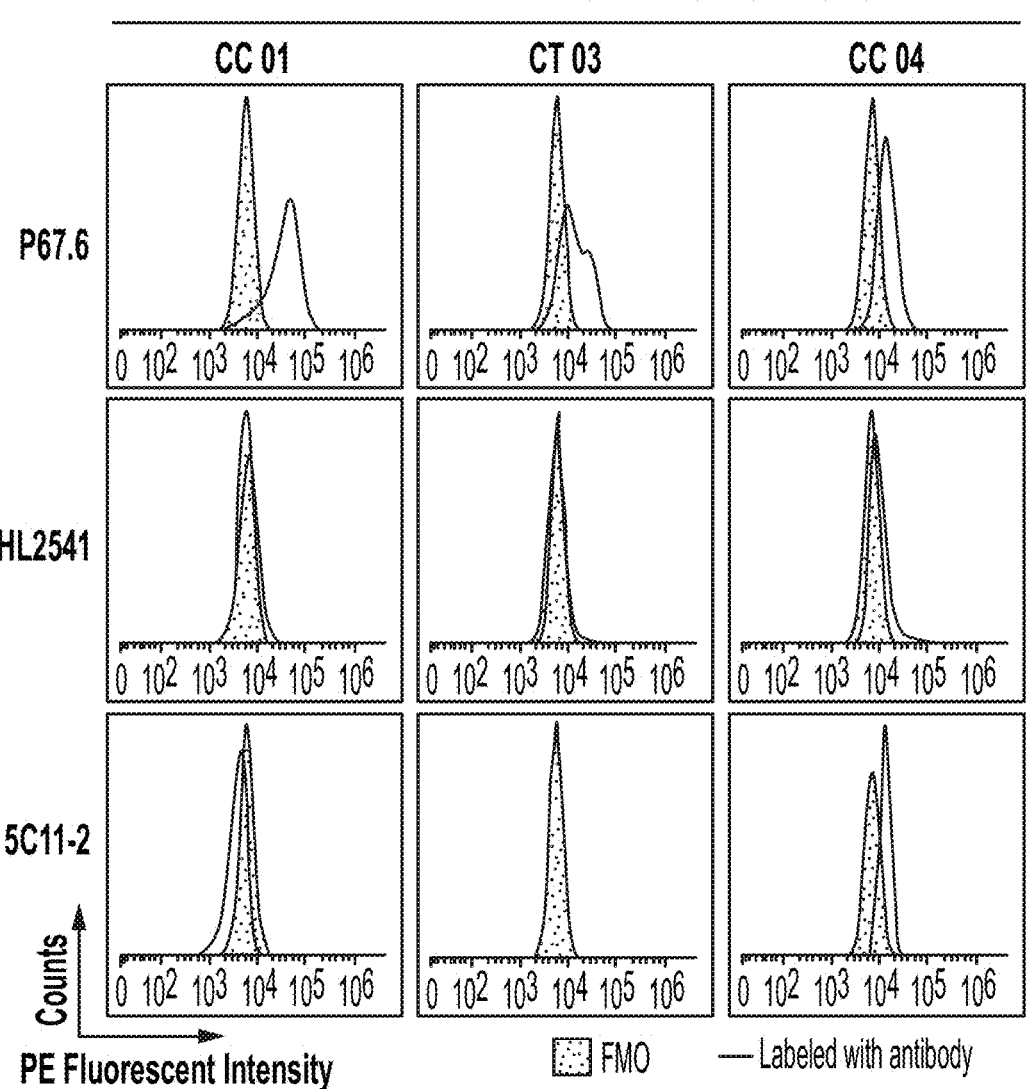
FIGS. 9A-9C show flow cytometry data.
Figure 9B:
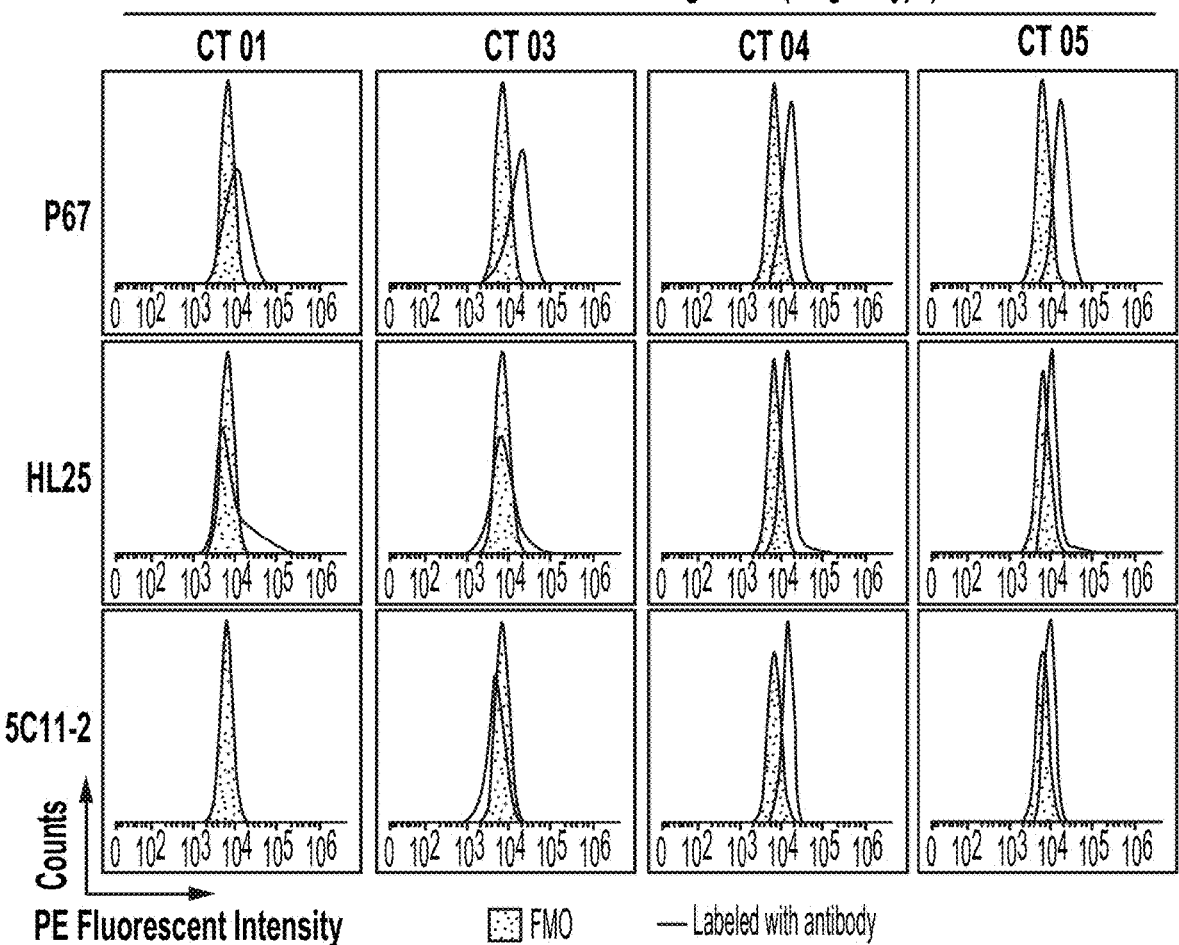
Figure 9C:
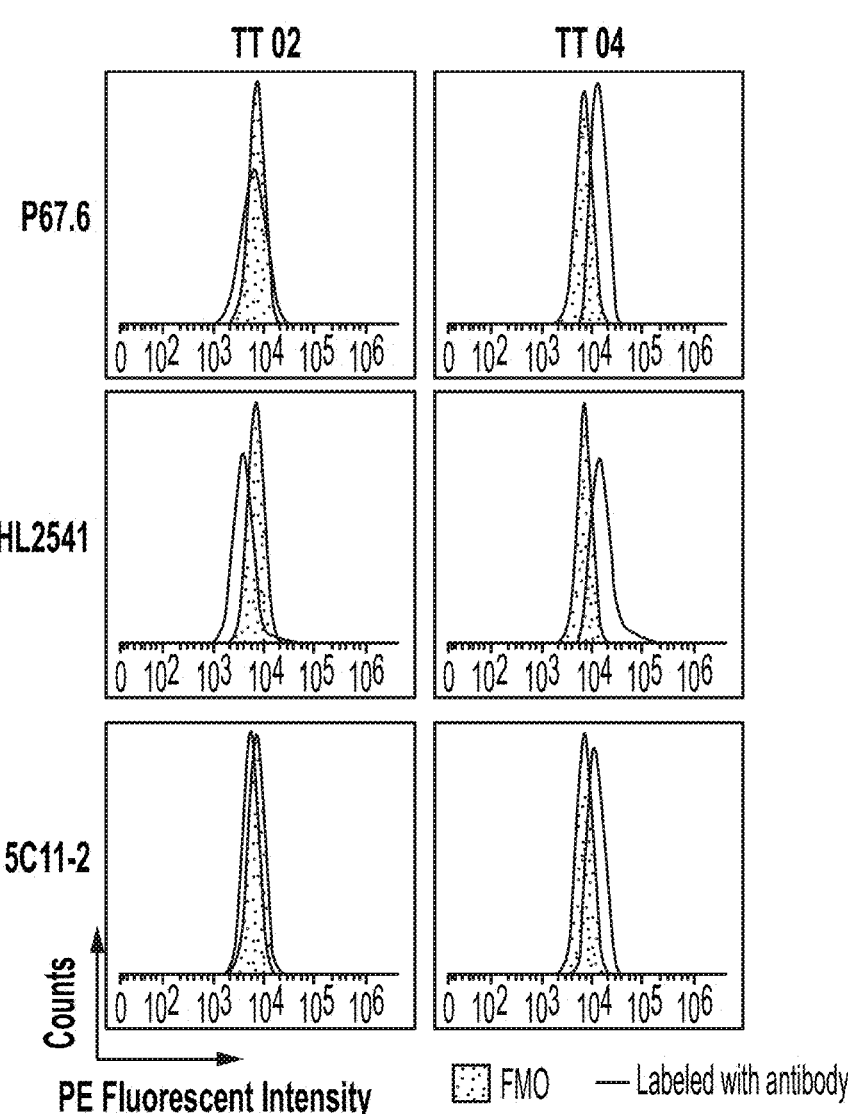
Figure 10A:
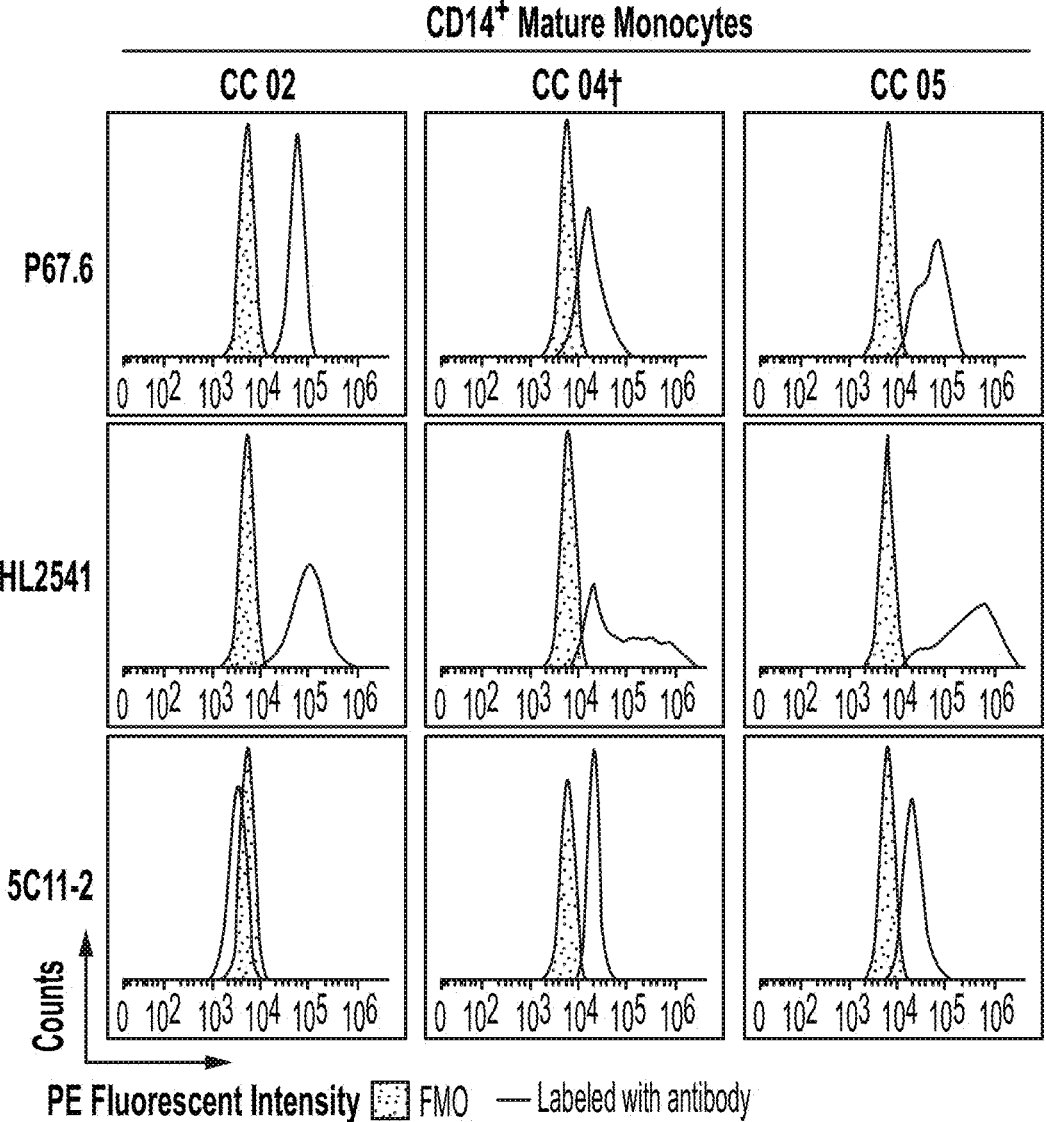
FIGS. 10A-10C show flow cytometry data.
Figure 10B:
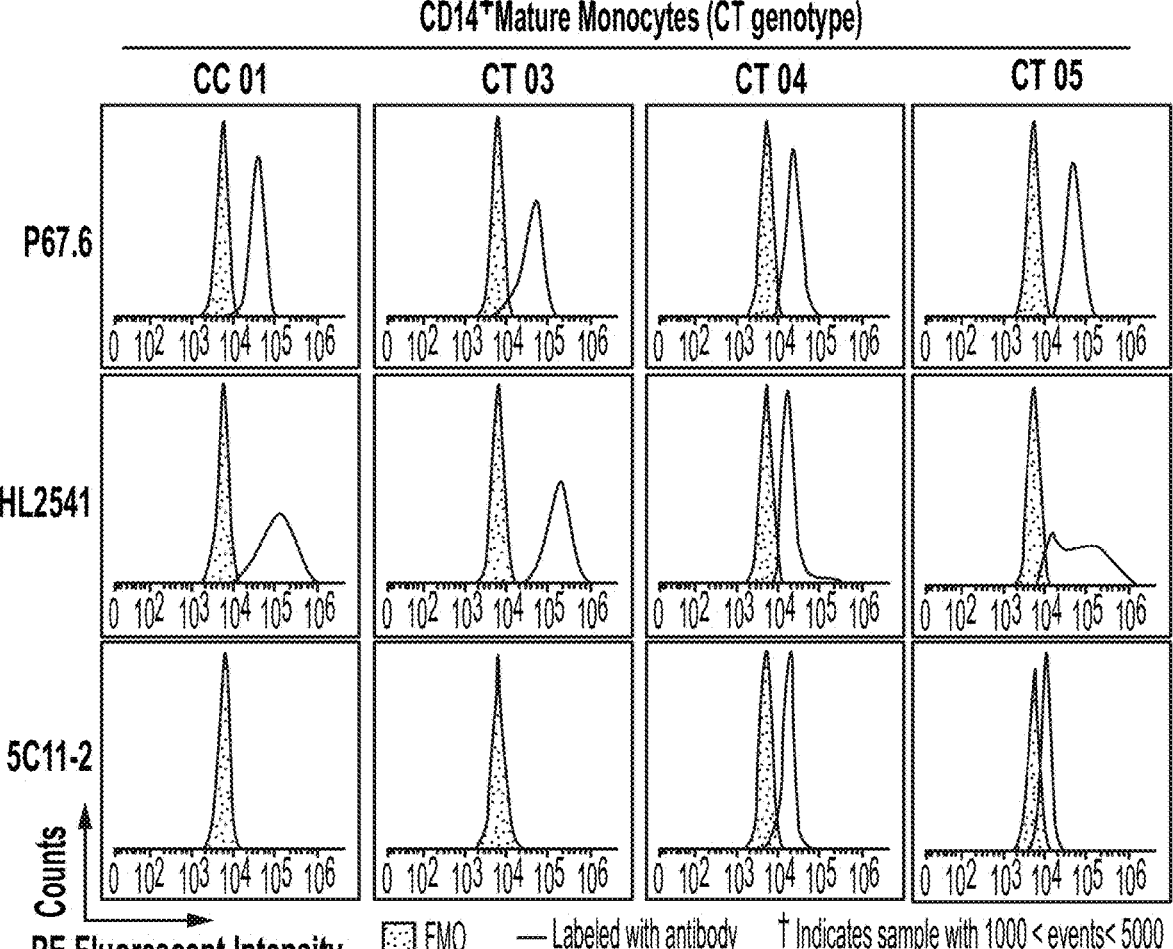
Figure 10C:
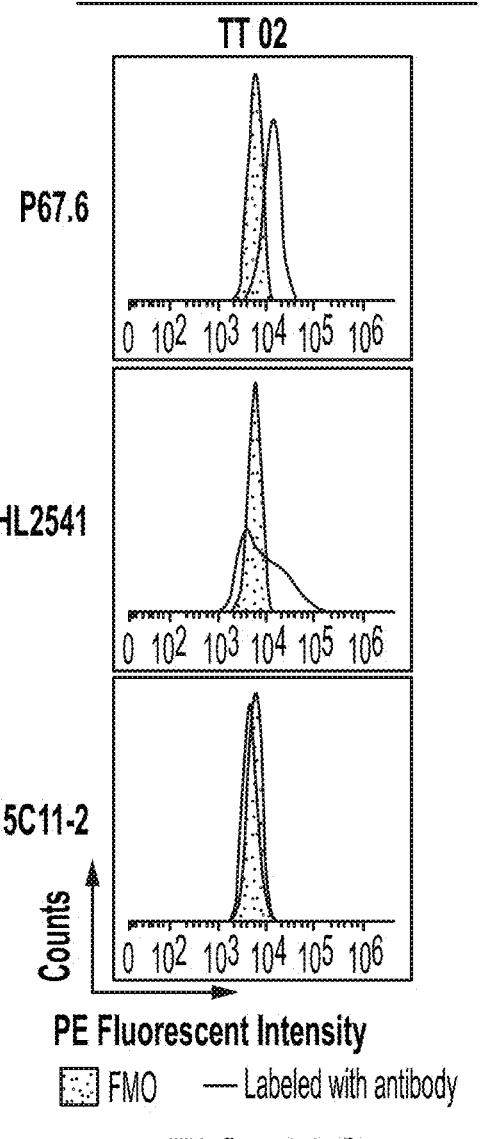
Figure 11:
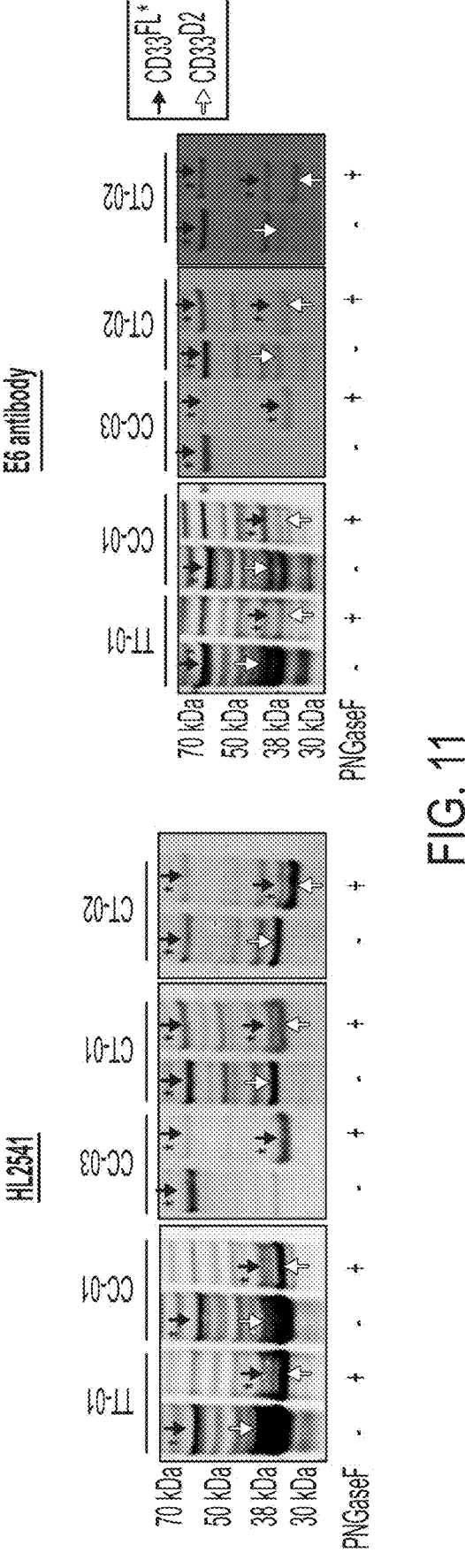
FIG. 11 shows Western blot data indicating recognition of CD33 isoforms on PNGaseF-treated and untreated primary cells representing different (CC, CT, TT) genotypes using anti-CD33 mAbs HL2541 and E6.
Figure 12A:
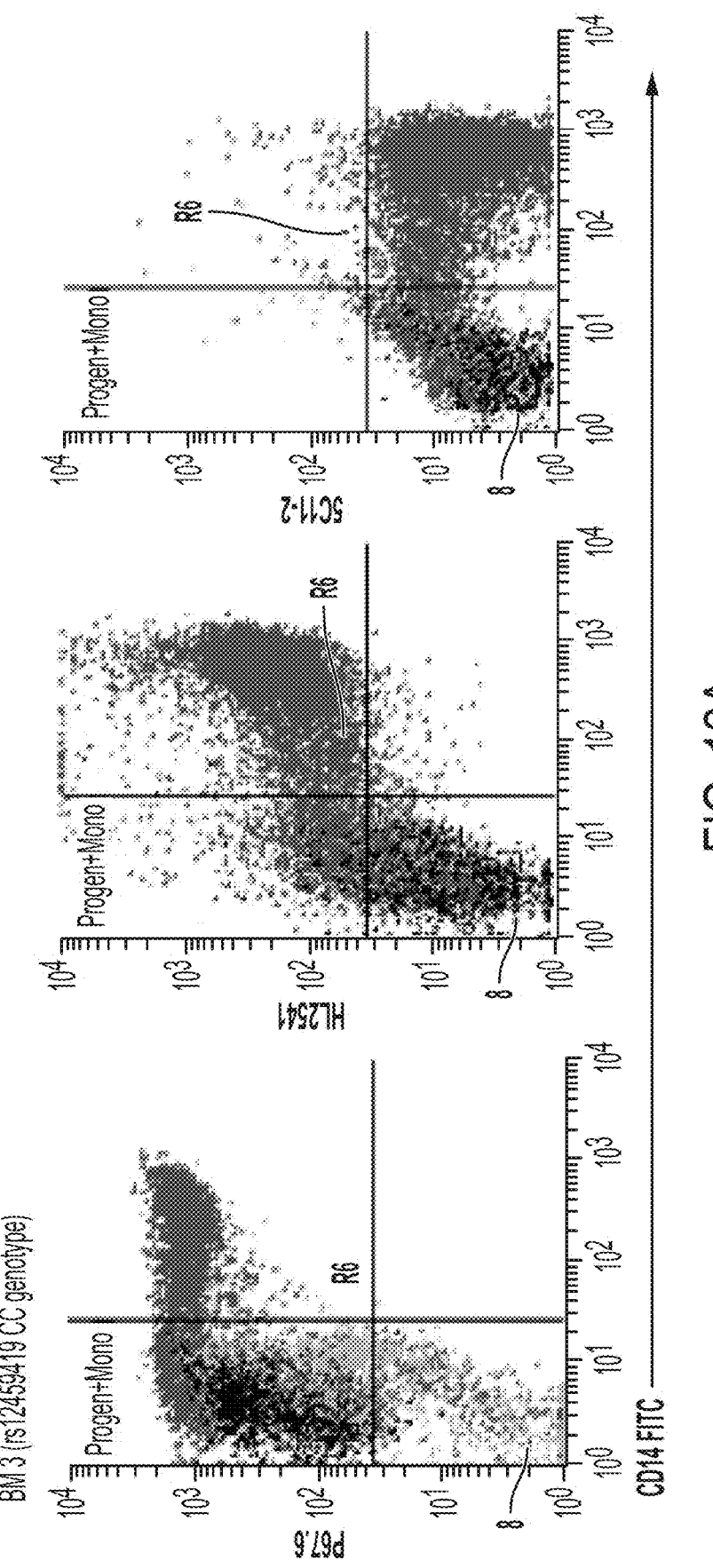
FIGS. 12A-12B show cell surface expression of CD33 on bone marrow specimens obtained after remission stained with P67/6, HL2541, and 511C-2.
Figure 12B:
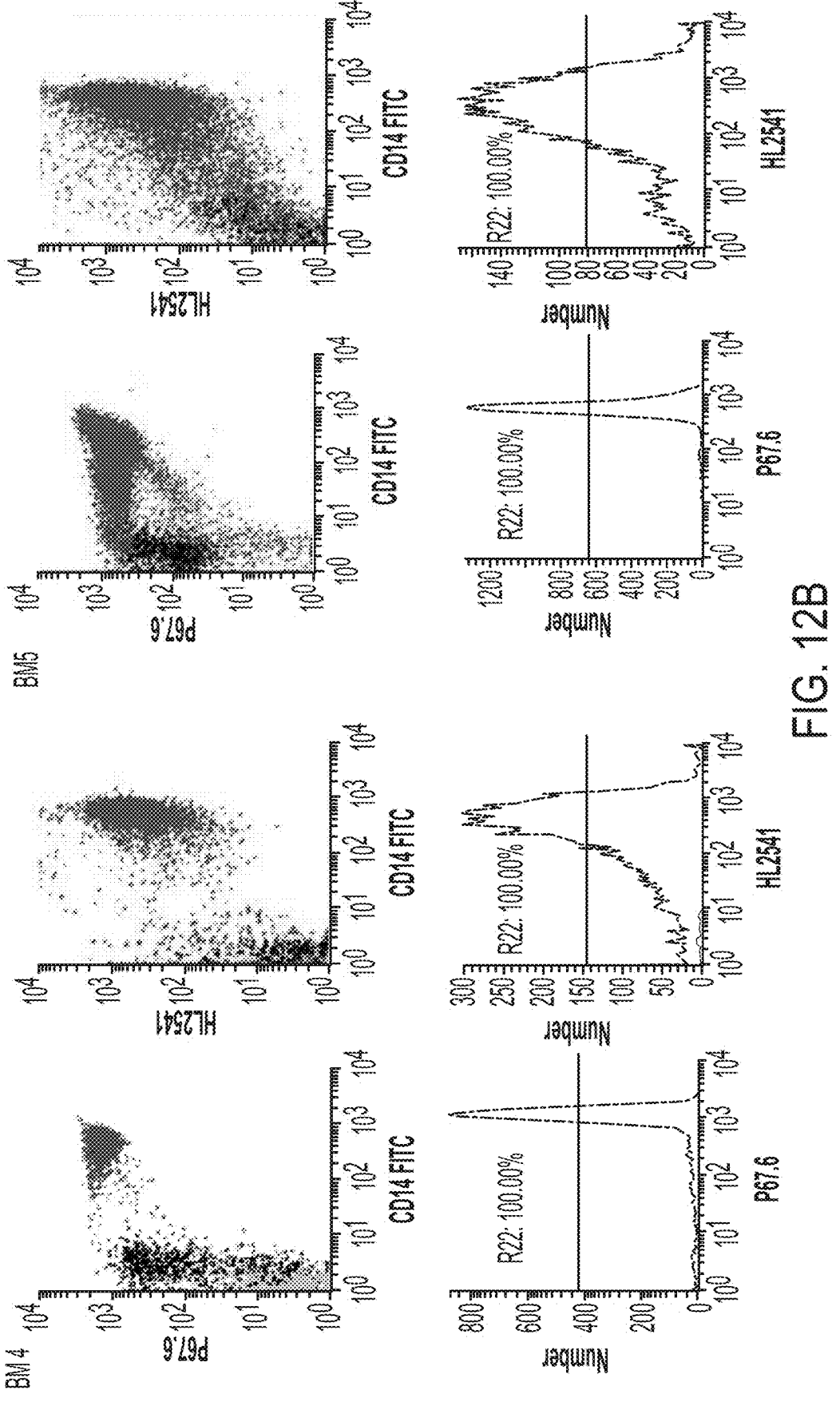

Primary cells were stained using CD34, CD14, and CD45 antibodies allowing for gating on an immature CD14⁻CD45$^{dim}$CD34⁺ population of AML cells and a more mature CD14⁺ monocytic population. Cells were also stained with P67.6, HL2541, or 5C11-2 antibodies and samples were determined as positive based on the shift from fluorescence minus one (FMO) control. All gating was done on live cells and positivity was determined using negative gates (FIG. 3A). In AML progenitor cells (CD14⁻CD45$^{dim}$CD34⁺ cells), a genotype-dependent recognition of CD33$^{FL}$ was observed with P67.6 in specimens from homozygous dominant (CC genotype) patients, who displayed stronger positive signal in comparison to samples from heterozygous and homozygous recessive patients (CT or TT). 5C11-2 and HL2541 staining showed minimal to no shift in the histograms of stained samples compared to the FMO, regardless of rs12459419 genotype, illustrating minimal/no CD33$^{D2}$ cell surface recognition in CD14⁻CD45$^{dim}$CD34⁺ progenitor cells. Representative samples corresponding to each genotype are shown in FIG. 3B (additional samples are shown in FIGS. 9A-9C). When gating on CD14⁺ monocyte of the same patient samples, CT and TT patients displayed a shift using the HL2541 antibody in comparison to the FMO control in selected patients (FIG. 3C and FIGS. 10A-10C). Western blotting of primary AML cells from patients with different genotypes performed with and without PNGaseF treatment using HL2541 and E6 antibodies confirmed recognition and intracellular presence of CD33 isoforms (FIG. 11).

expression, while lymphoblastic progenitor cells were negative for CD33$^{FL}$ cell surface expression. CD14⁻CD45$^{dim}$CD34⁺ progenitor cells were negative for CD33$^{D2}$ cell surface expression for HL2541 and 5C11-2, while CD14⁺ monocytes cells showed some positive signal with HL2541, consistent with the results from diagnostic AML samples (FIG. 4B). FIGS. 12A-12B show results of the 3 additional bone marrow specimens stained with P67.6, HL2541, and/or 5C11-2.

TABLE 4

Antibody dilutions used for Western blotting experiments.

| Target | Isotype | Clone | Species | Reactivity | Western Blotting Dilution |
|---|---|---|---|---|---|
| CD33 | IgG1 | E6 | Mouse | Human | 1:250 |
| CD33 (IgC) | IgG1 | HL2541 | Mouse | Human | 1:50 |
| CD33 (IgC) | IgG2a | 5C11-2 | Mouse | Human | 1:250 |
| H3 Histone | IgG | 3H1 | Rat | Mouse | 1:1000 |

TABLE 5

| | | | | | Flow Cytometry | | |
| Target | Isotype | Clone | Species | Reactivity | Fluorophore | Amount (ng) | Dilution |
|---|---|---|---|---|---|---|---|
| CD33 | IgG1 | P67.6 | Mouse | Human | PE | 500 | 1:40 |
| CD33 | IgG1 | P67.6 | Mouse | Human | PE | 500 | 1:8 |
| CD33 (IgC) | IgG1 | HL2541 | Mouse | Human | PE | 500 | 1:200 |
| CD33 (IgC) | IgG2a | 5C11-2 | Mouse | Human | PE | 500 | 1:20 |
| CD14 | IgG2a | M5E2 | Mouse | Human | Pacific Blue | 800 | 1:50 |
| CD14 | IgG2a | MφP9 | Mouse | Human | FITC | | |
| CD34 | IgG2a | 561 | Mouse | Human | APC | 100 | 1:50 |
| CD34 | IgG2a | 8G12 | Mouse | Human | APC | | |
| CD45 | IgG1 | 2D1 | Mouse | Human | SB 600 | 150 | 1:33 |
| CD45 | IgG1 | 2D1 | Mouse | Human | PerCP | | |

Flow cytometry antibodies.

TABLE 6

| | | | | | Immunofluorescence Microscopy | | |
| Target | Isotype | Clone | Species | Reactivity | Fluorophore | Amount (ug) | Dilution |
|---|---|---|---|---|---|---|---|
| CD33 | IgG1 | P67.6 | Mouse | Human | NA | 2 | 1:10 |
| CD33 (IgC) | IgG1 | HL2541 | Mouse | Human | NA | 2 | 1:50 |
| CD33 (IgC) | IgG2a | 5C11-2 | Mouse | Human | NA | 2 | 1:5 |
| IgG H&L Chain | IgG | N/A | Goat | Mouse | Alexa Fluor ® 647 | 1 | 1:2000 |

Antibodies used for immunofluorescence microscopy.

Example 2

Targeting CD33 IgC Domain Elicits Potent T Cell-Mediated Toxicity Against Acute Myeloid Leukemia Cells.

Figure 13:
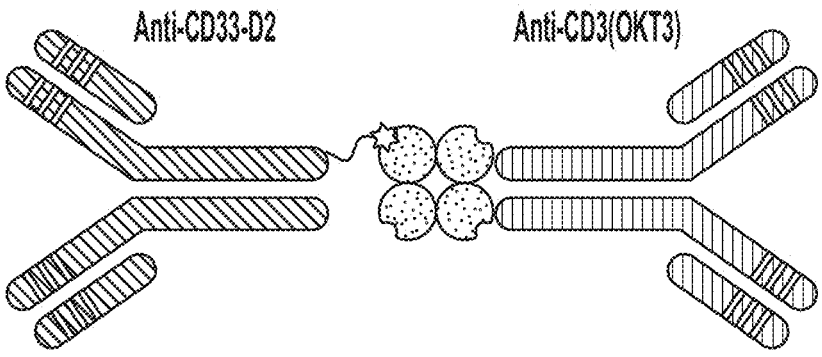
FIG. 13 shows one embodiment of CD33$^{D2}$/CD3 Adaptable Cell Engager (ACE).

A CD33$^{D2}$/CD3 Adaptable Cell Engager (ACE) was designed using conjugated anti-CD33$^{D2}$ (HL-2541) with biotinylated anti-CD3 (OKT3) using a streptavidin/biotin linkage (FIG. 13). T cells were isolated from PBMCs using CD3/CD28 Dynabeads and expanded.

Figure 14:
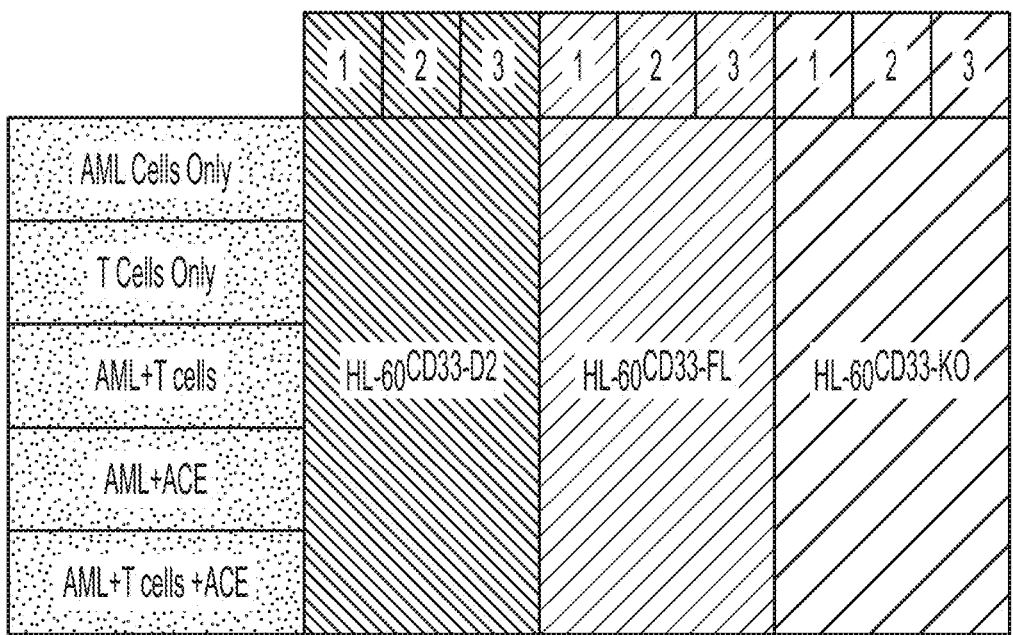
FIG. 14 shows one embodiment of CD33$^{D2}$/CD3 ACE experimental design for assaying T cell mediated cytotoxicity.

AML cells were labeled with CFSE and 200,000 cells were seeded in 100 μL complete T cell media in the following conditions: 1) AML cells alone, 2) T cells alone, 3) AML and T cells (100,000 cells each in total 100 μL), 4) AML cells with ACE, 5) AML cells and T cells with ACE (FIG. 14). ACE was added in 100 μL complete T cell media in the appropriate wells and 100 μL complete T cell media without ACE was added to the controls. The cells were cultured for 24 or 72 hours, and viability was assayed using flow cytometry.

Figures 15, 16:
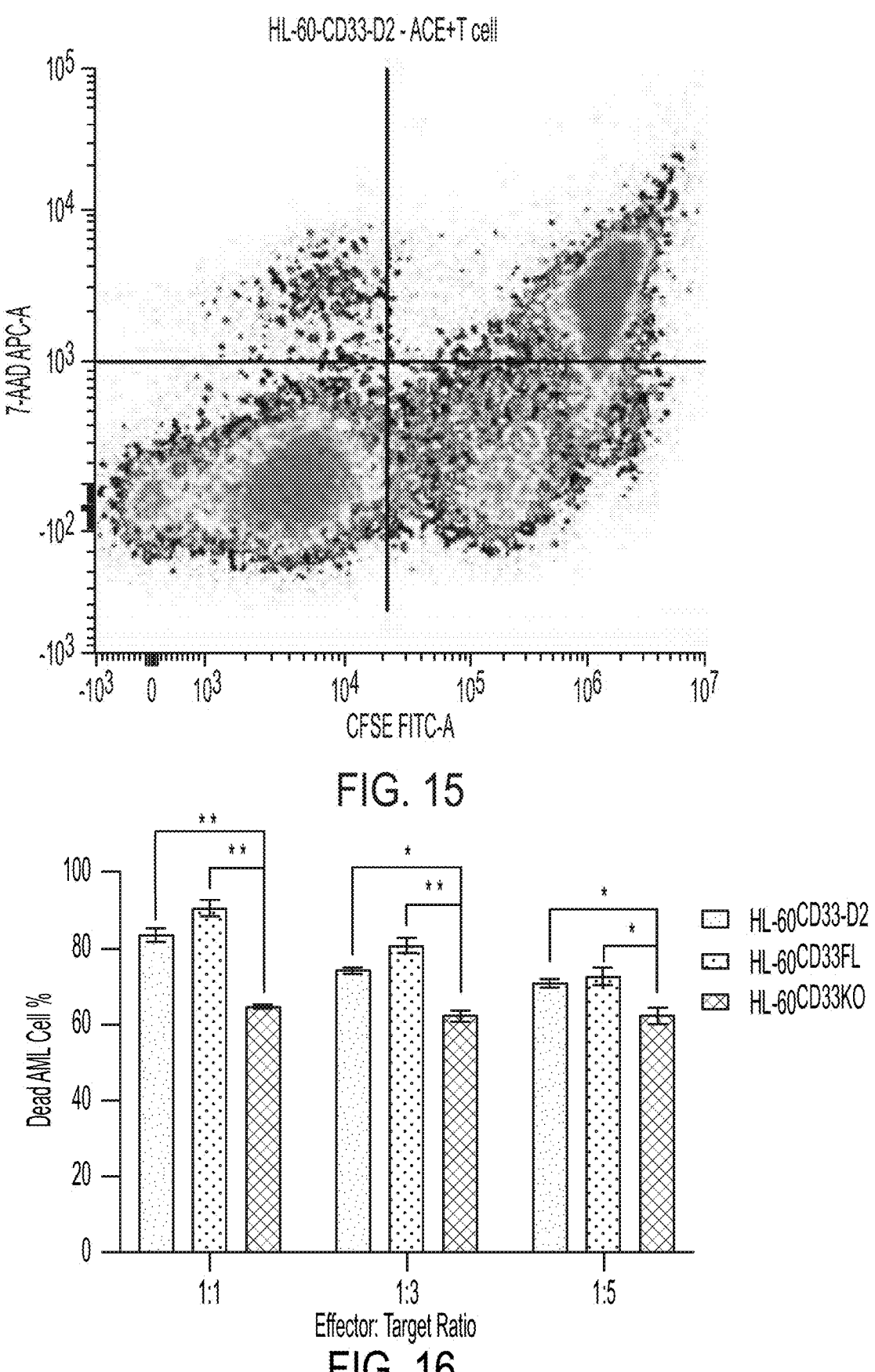
FIG. 15 shows the gating strategy for cell viability.
FIG. 16 shows T cell mediated elimination of CD33$^{D2}$ and CD33$^{FL}$ expressing HL-60 cells by CD33$^{D2}$×CD3 ACE at 72 hours.

CFSE-labeled HL-60 cells (either expressing CD33$^{FL}$, CD33$^{D2}$, or no CD33) were co-cultured with T cells expanded from PBMCs and CD33$^{D2}$×CD3 ACE for 24 or 72 hours (FIG. 15). The CFSE position/7-AAD positive cells were measured as dead AML cells (FIG. 15). The following groups served as controls: 1) T cells only, 2) AML cells only, 3) AML cells+ACE, and 4) AML cells+T cells.

Figure 17A:
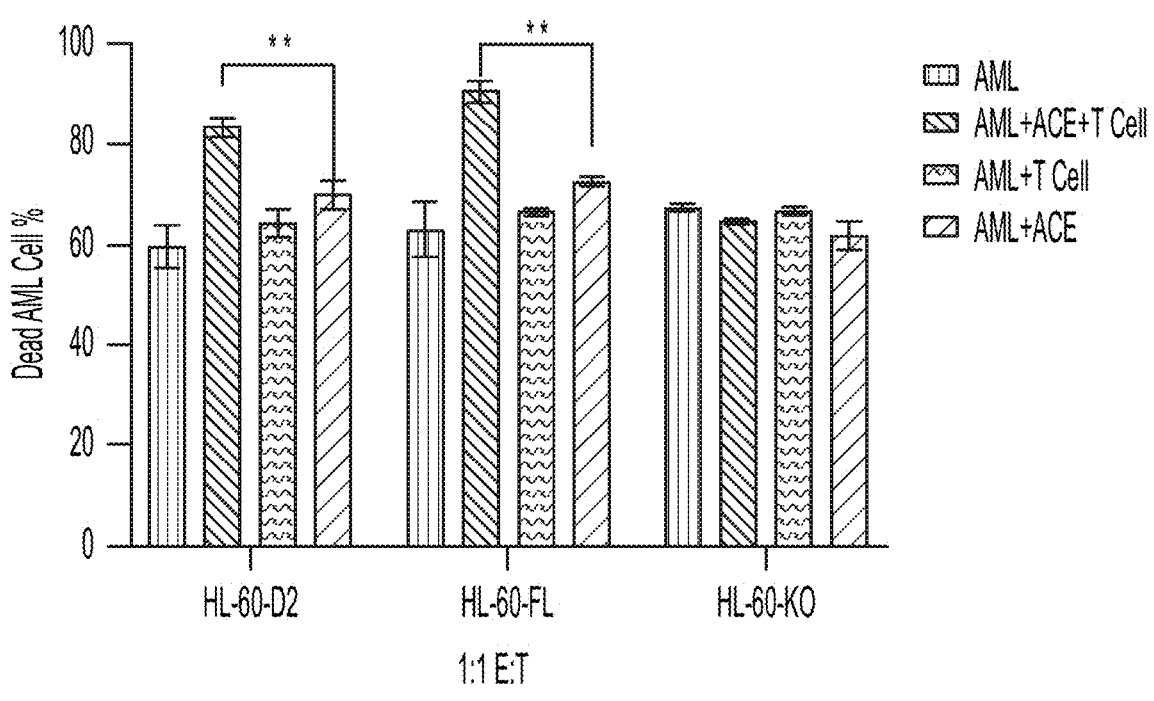
FIGS. 17A-17C show increased toxicity in controls at 73 hours-potential effect of culturing AML cells in T cell media.
Figure 17B:
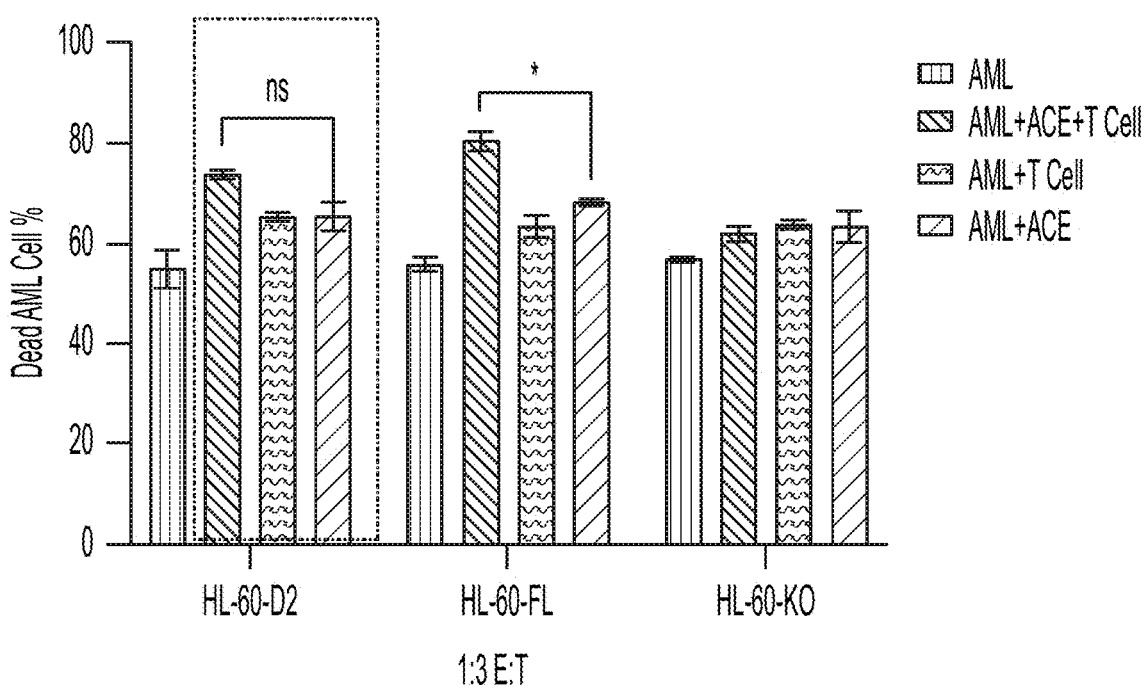
Figure 17C:
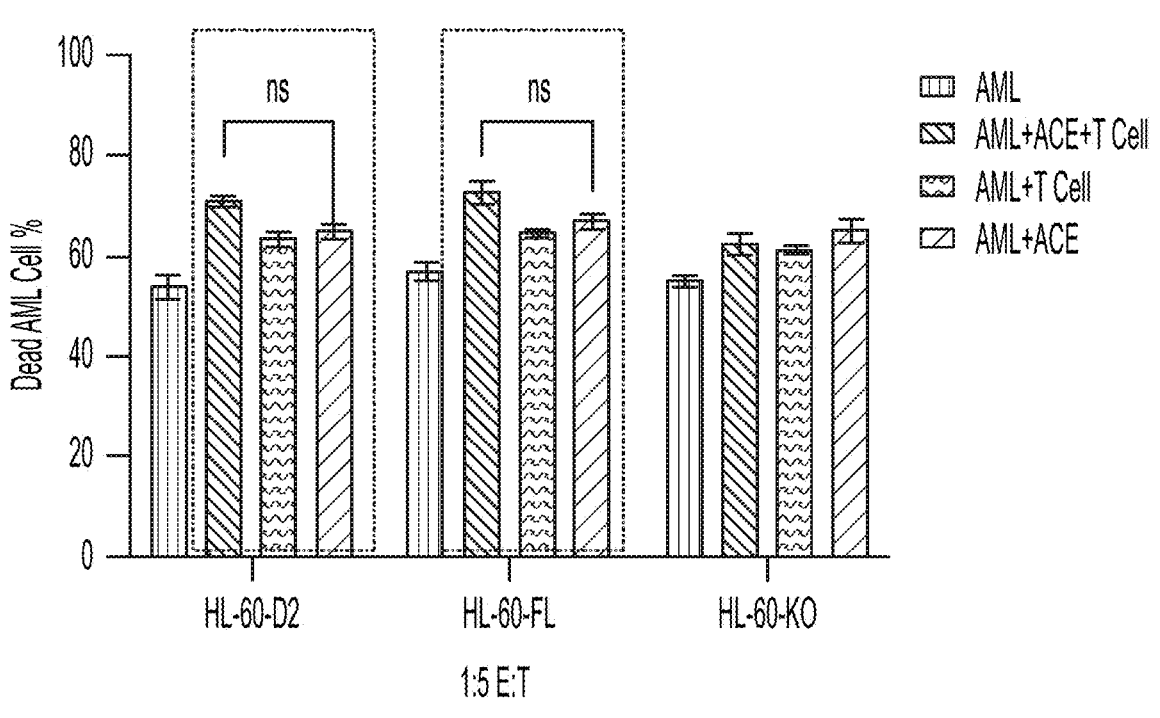

T cell-mediated elimination of CD33$^{D2}$- and CD33$^{FL}$-expressing HL-60 cells by CD33$^{D2}$×CD3 was observed at 72 hours (FIG. 16). However, increased toxicity was noted in the control groups at the same time point, demonstrating a potential effect of culturing cells in T cell media (FIGS. 17A-17C).

Figure 18:
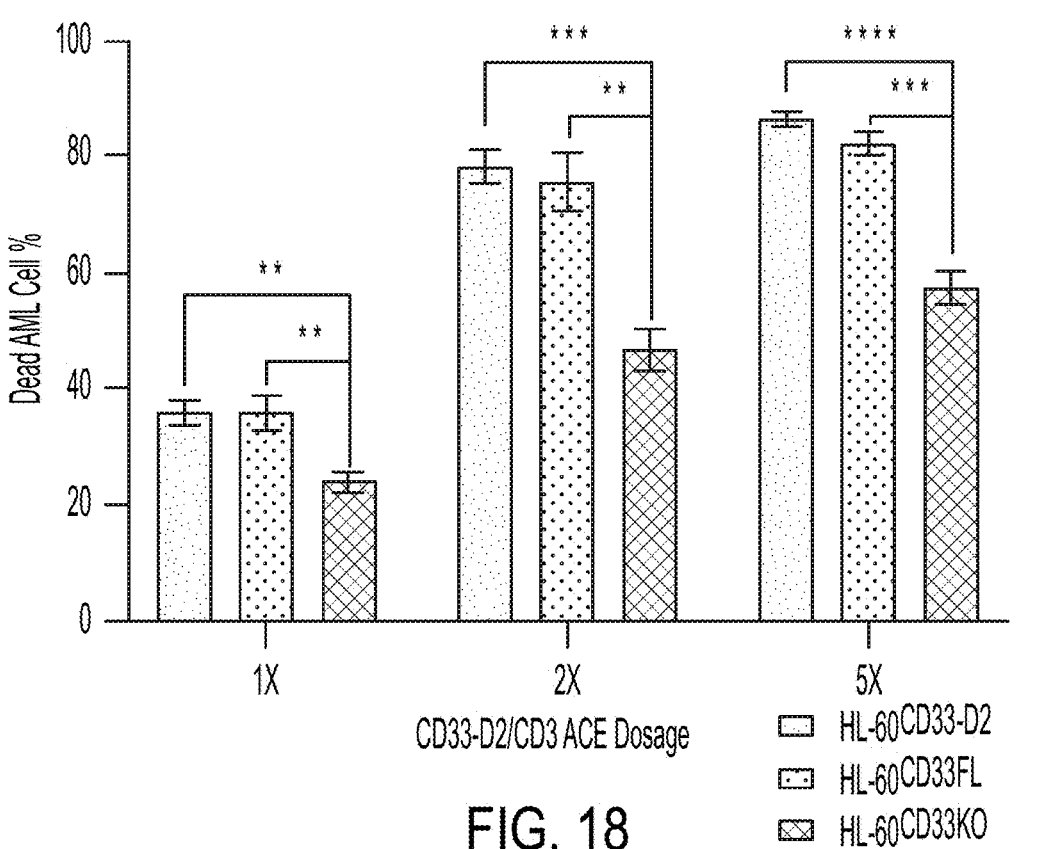
FIG. 18 shows CD33$^{D2}$× CD3 ACE mediates dose-dependent T cell killing CD33$^{D2}$ and CD33$^{FL}$ expressing HL-60 cells at 24 hours.
Figure 19A:
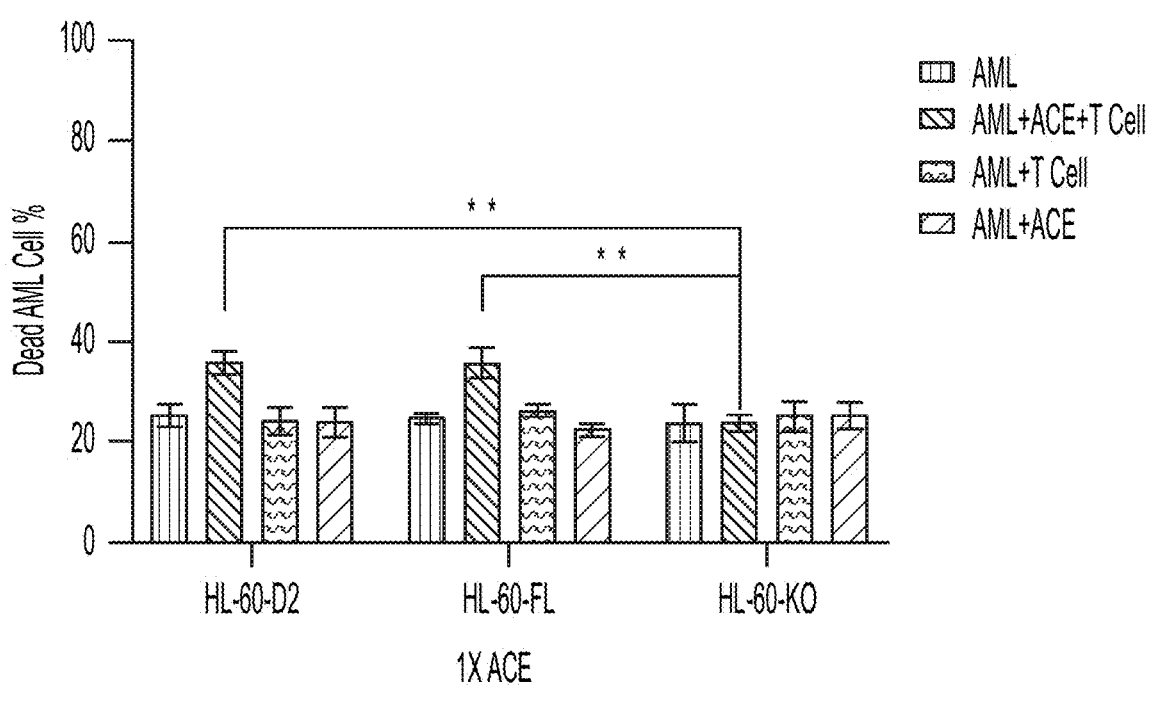
FIGS. 19A-19C show increased toxicity in controls at higher ACE dosage after 24 hours-potential non-specific cytotoxicity.
Figure 19B:
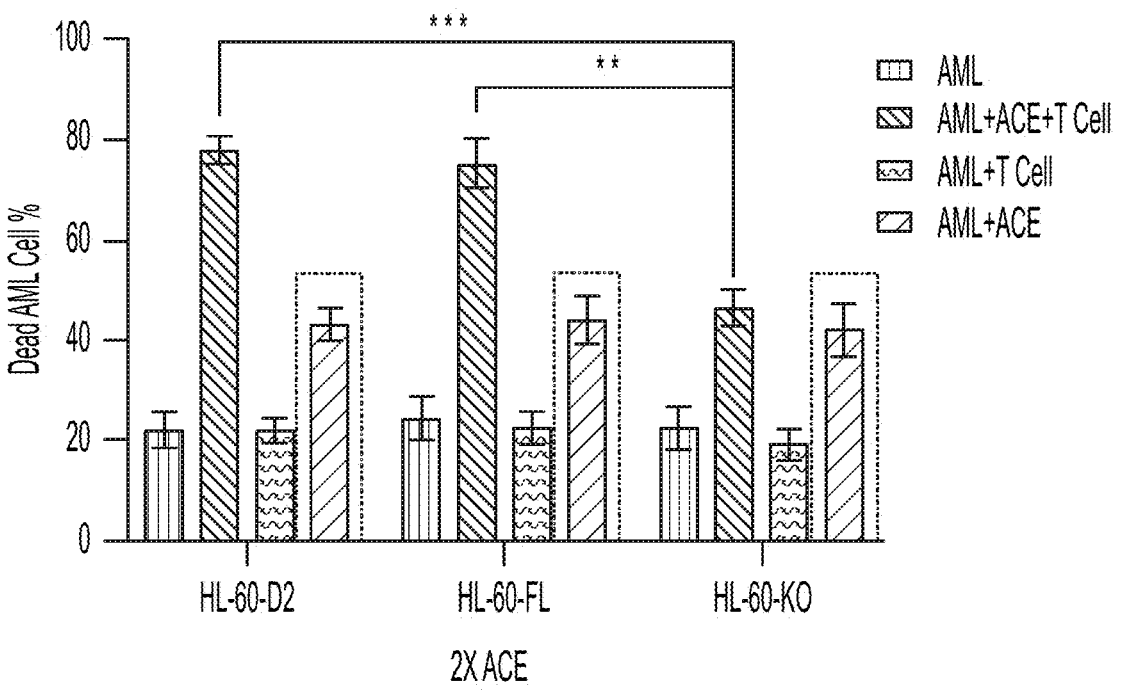
Figure 19C:
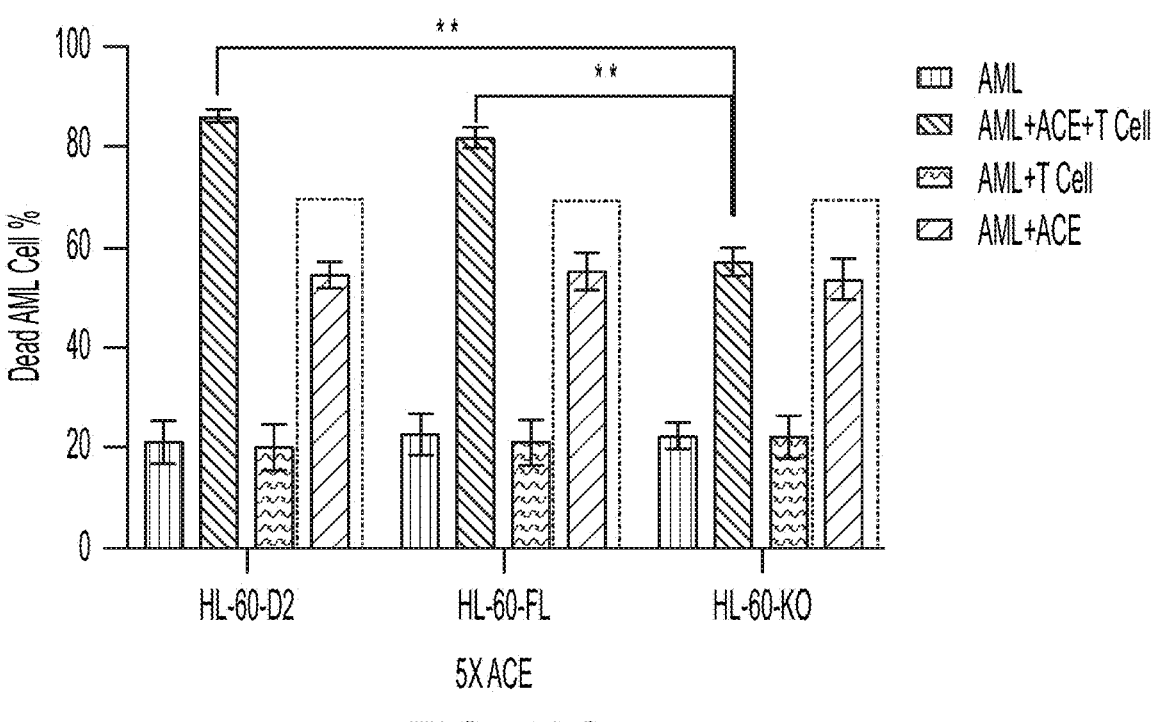
Figure 20:
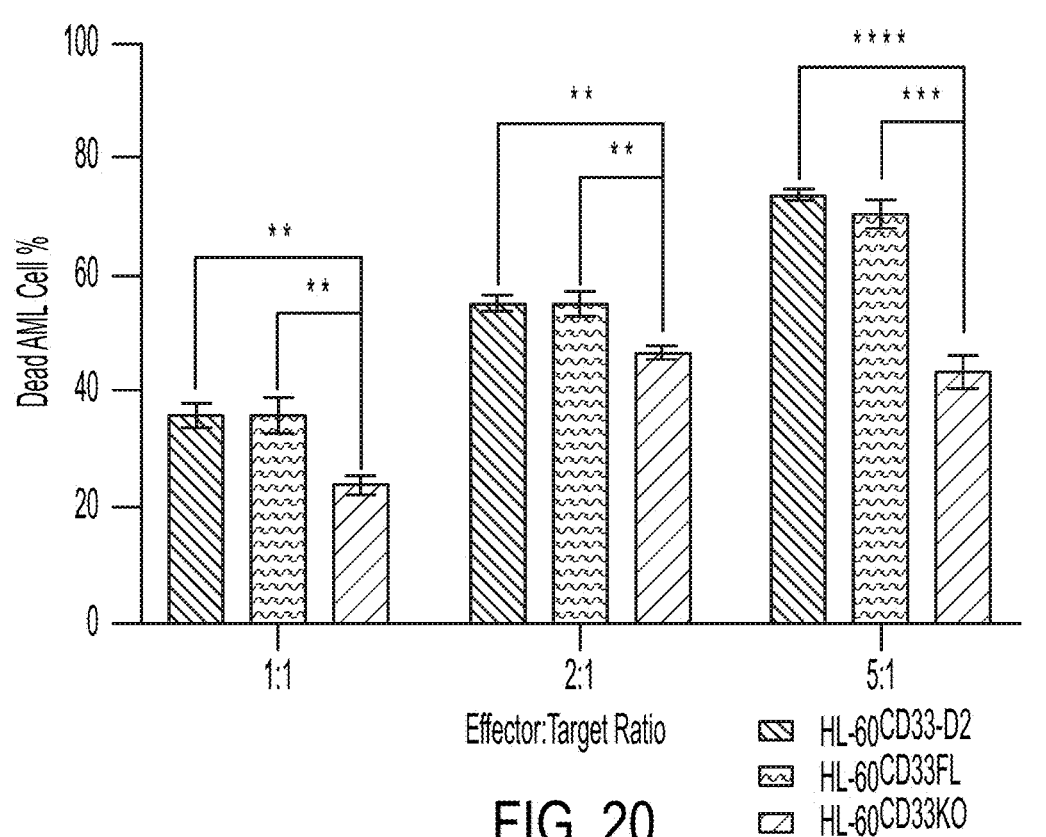
FIG. 20 shows 1×CD33$^{D2}$× CD3 ACE mediates increased T cells killing of CD33$^{D2}$ and CD33$^{FL}$ expressing HL-60 cells in E:T ratio dependent manner after 24 hours.
Figure 21A:
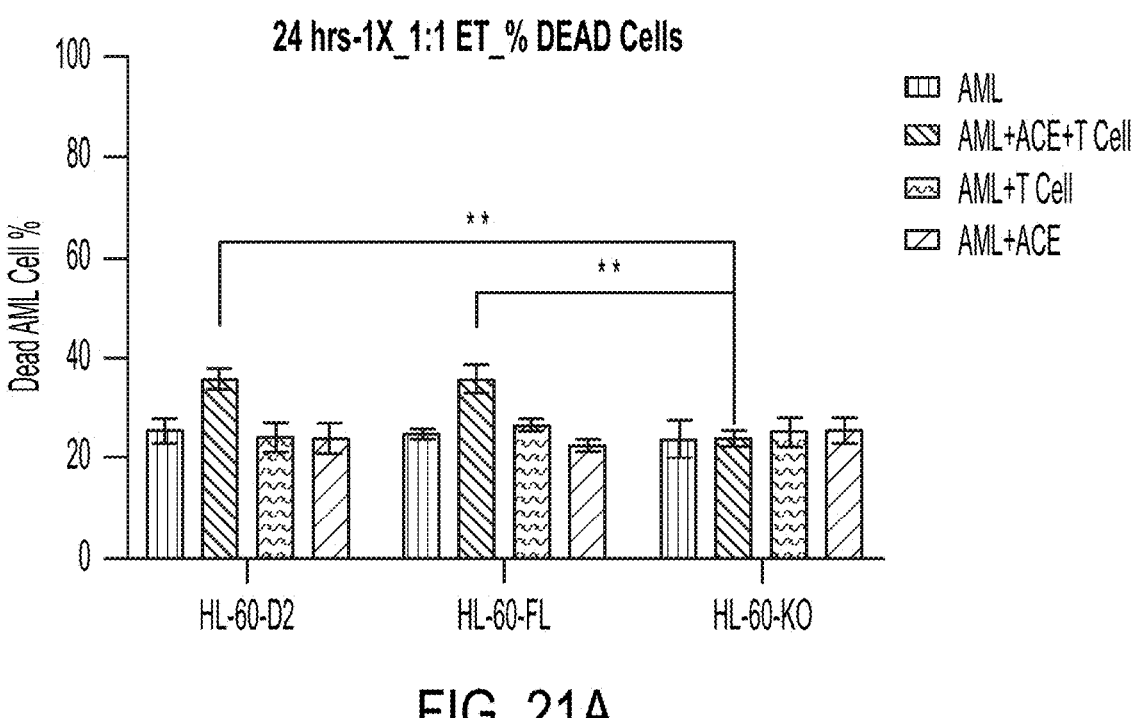
FIGS. 21A-21C show 1×CD33$^{D2}$× CD3 ACE mediates T cell killing of CD33$^{D2}$ and CD33$^{FL}$ expressing HL-60 cells at 5:1 E:T after 24 hours-controls.
Figure 21B:
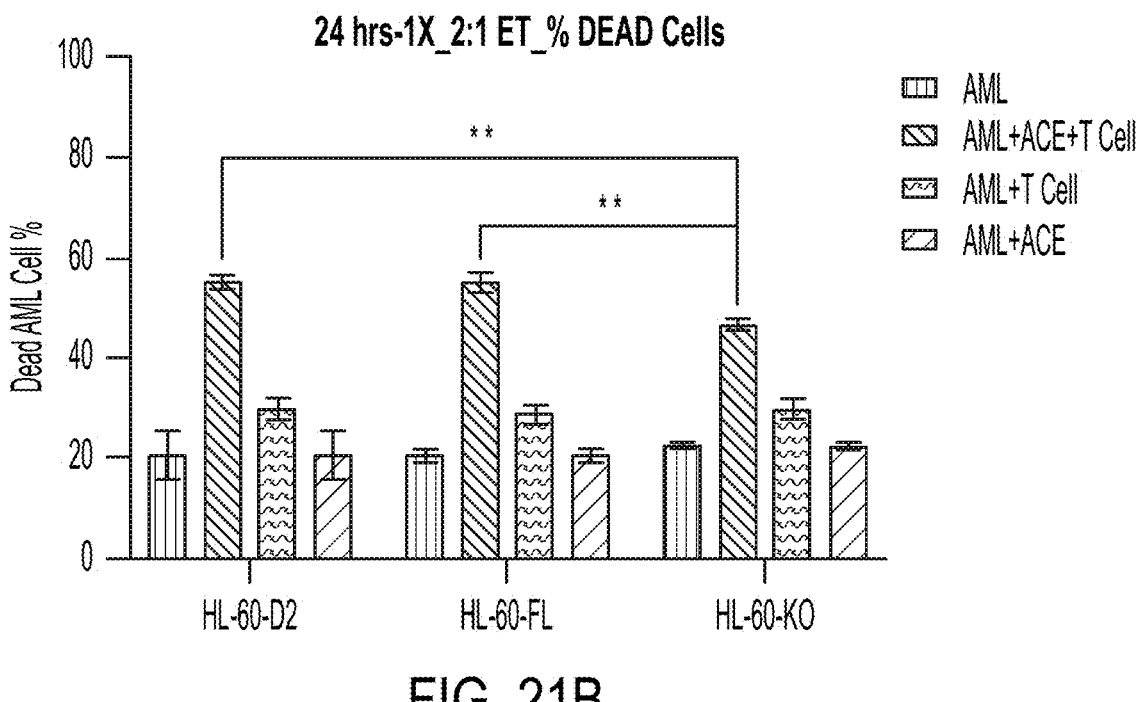
Figure 21C:
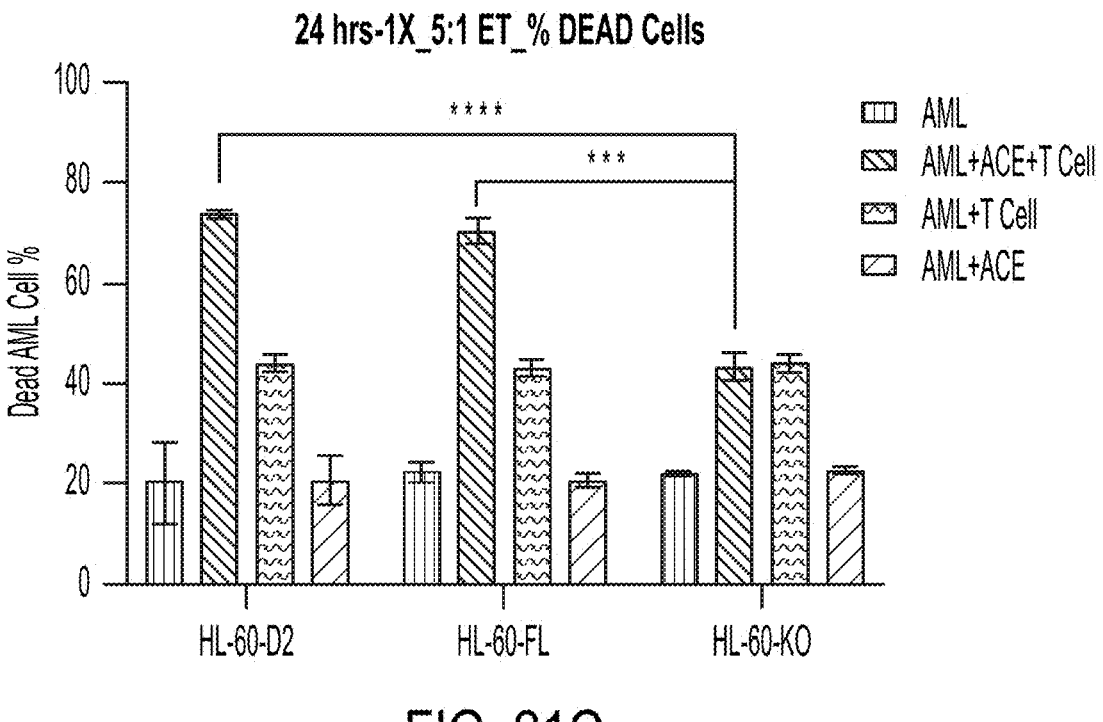

These studies indicate CD33$^{D2}$×CD3 ACE mediated dose-dependent T cell killing of HL-60 cells at 24 hours (FIG. 18). Increased toxicity was observed in controls with a higher ACE dosage after 24 hours, suggesting potential non-specific cytotoxicity (FIGS. 19A-19C). After 24 hours, 1×CD33$^{D2}$×CD3 ACE mediated increased T cell killing of HL-60 cells in an E:T ratio-dependent manner (FIG. 20). For the control groups it was observed that 1×CD33$^{D2}$×CD3 ACE mediated increased T cell killing of HL-60 cells at a 5:1 E:T ratio after 24 hours (FIGS. 21A-21C).

Figure 22:
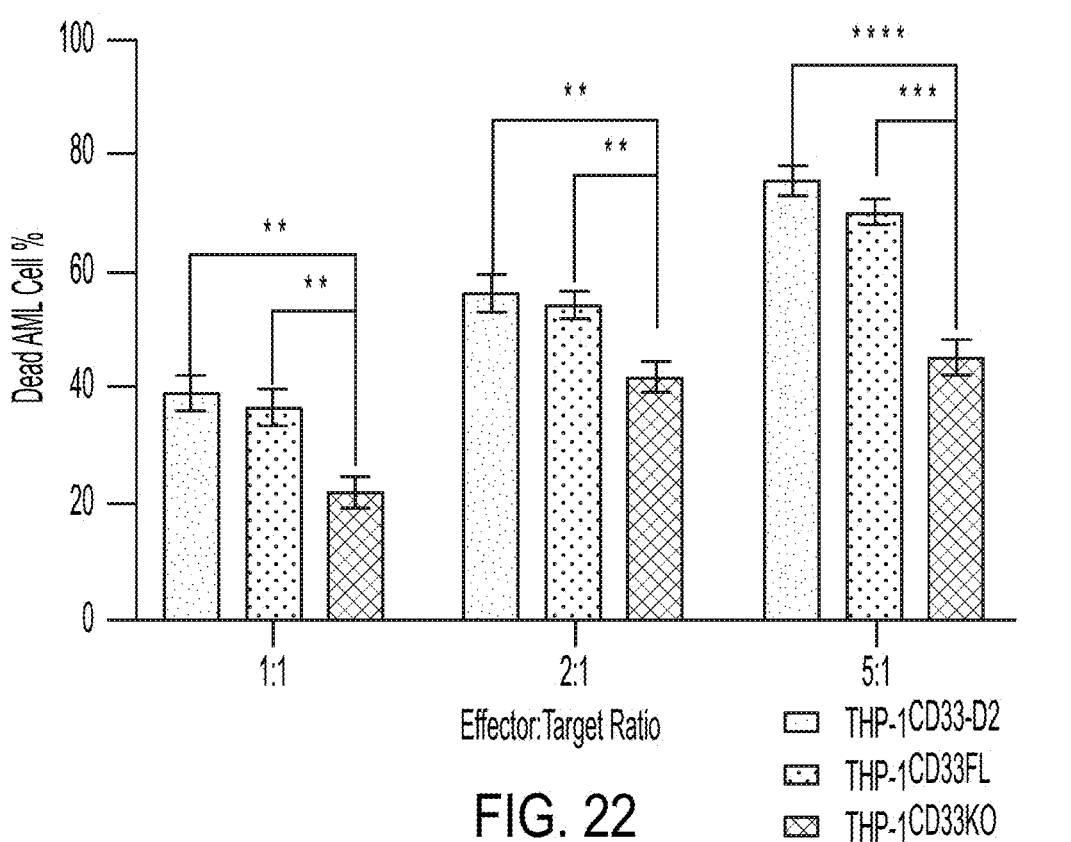
FIG. 22 shows 1×CD33$^{D2}$× CD3 ACE mediates increased T cell killing of CD33$^{D2}$ and CD33$^{FL}$ expressing THP-1 cells in E:T ratio-dependent manner after 24 hours.
Figure 23:
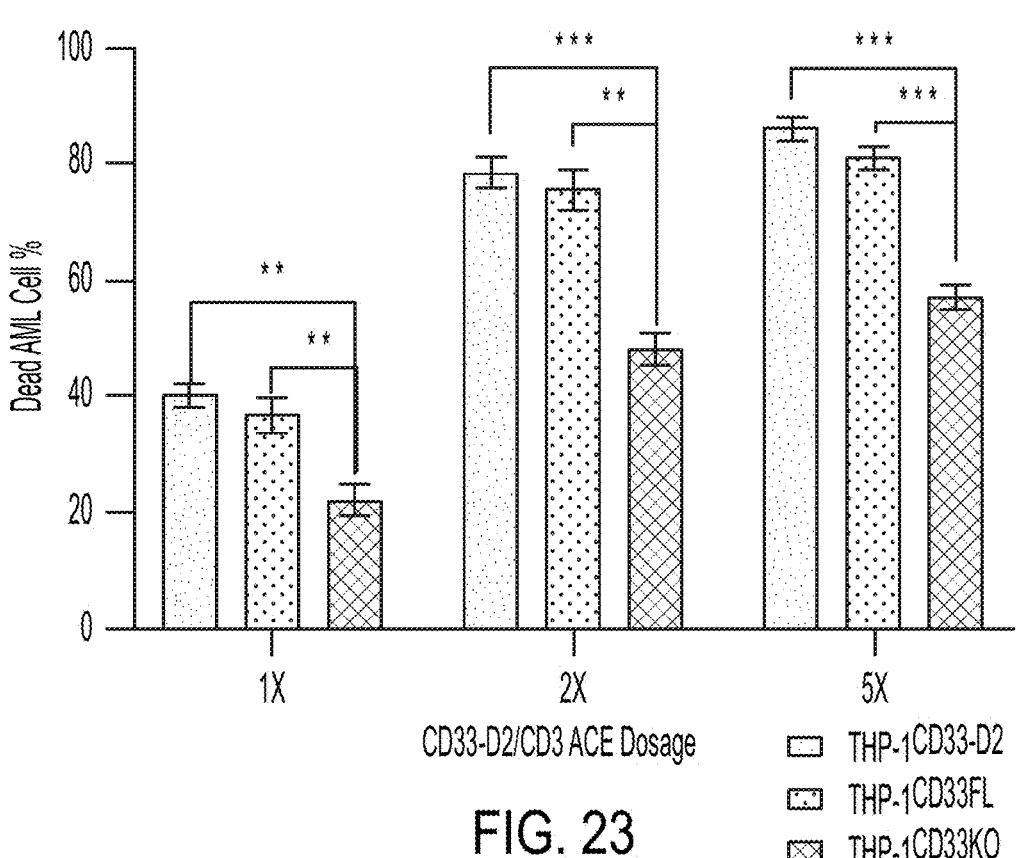
FIG. 23 shows CD33$^{D2}$× CD3 ACE mediates dose-dependent T cell killing of CD33$^{D2}$ and CD33$^{FL}$ expressing THP-1 cells at 24 hours.
Figure 24A:
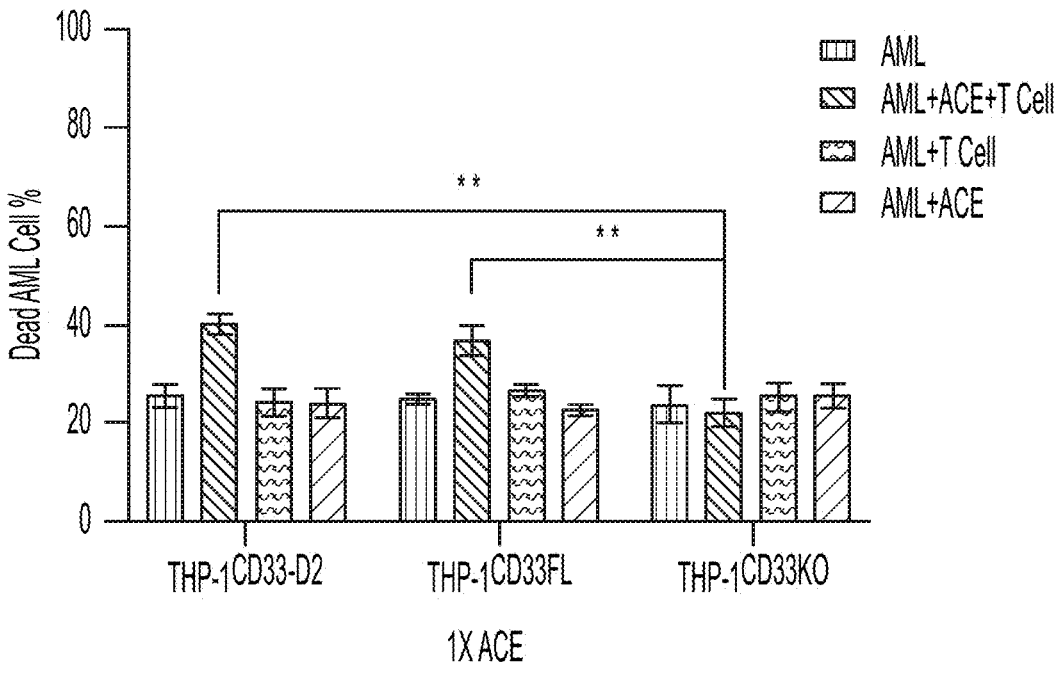
FIGS. 24A-24C show increased toxicity in controls at higher ACE dosage after 24 hours-potential non-specific cytotoxicity.
Figure 24B:
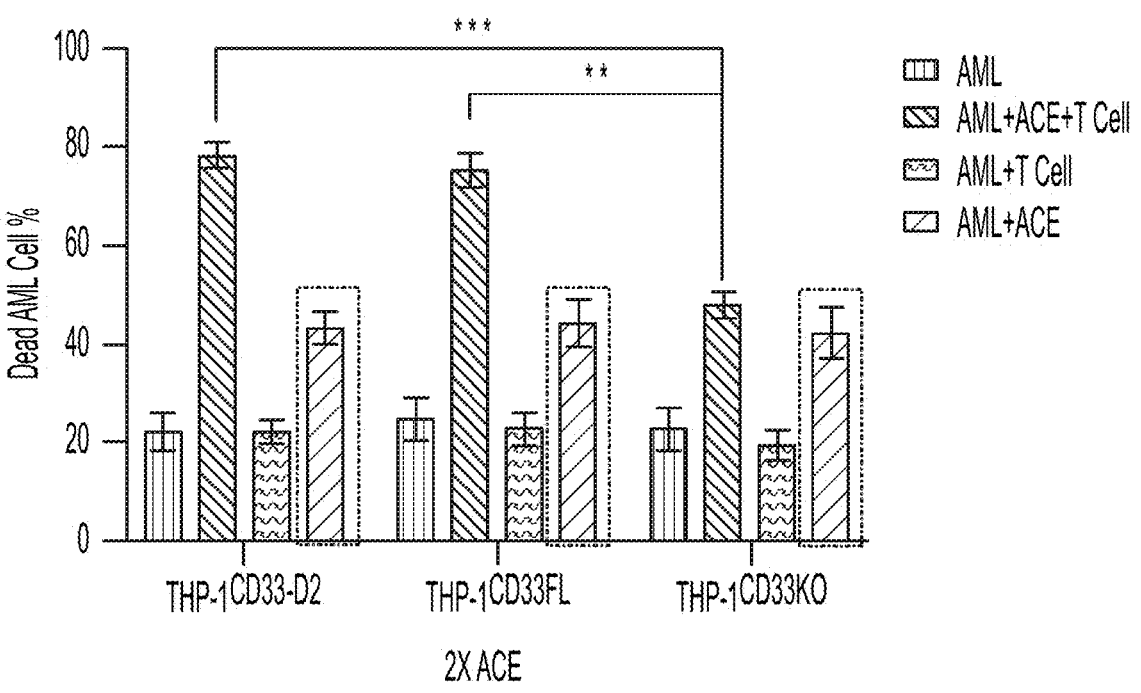
Figure 24C:
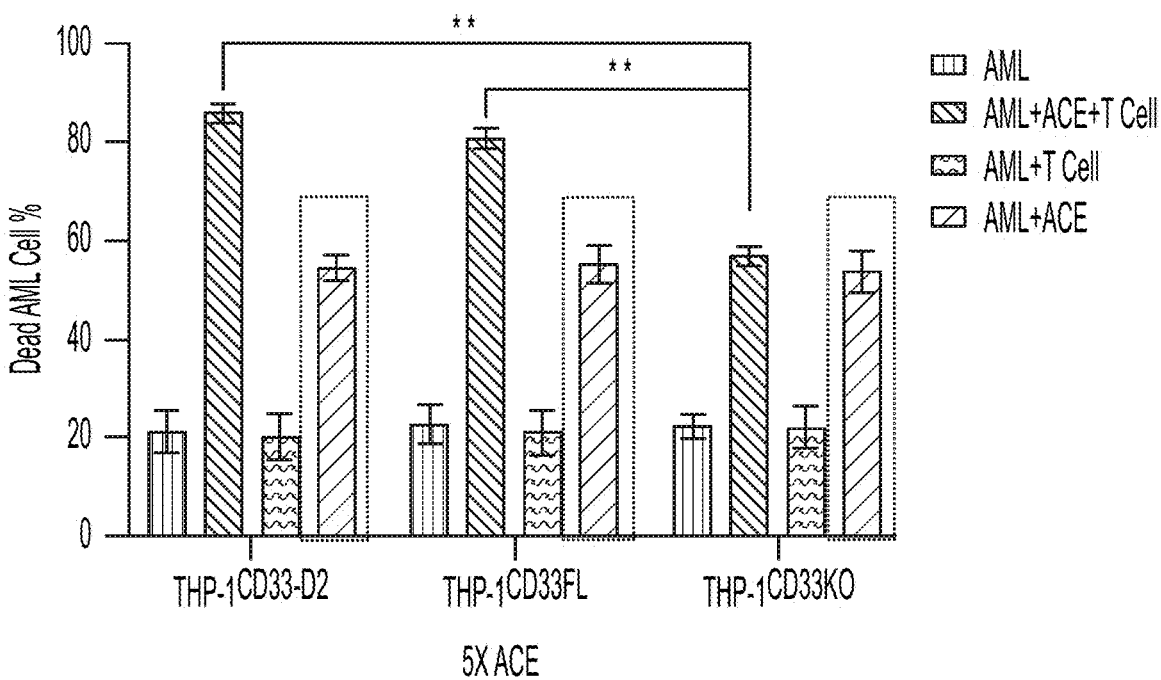

Increased T cell killing of THP-1 cells was mediated by 1×CD33$^{D2}$×CD3 ACE in an E:T ratio-dependent following 24 hours (FIG. 22). CD33$^{D2}$×CD3 ACE mediated dose-dependent T cell killing of THP-1 cells at 24 hours (FIG. 23). Increased toxicity was observed in the THP-1 controls at higher ACE dosages after 24 hours, suggesting a potential non-specific cytotoxicity effect (FIGS. 24A-24C).

Figure 25:
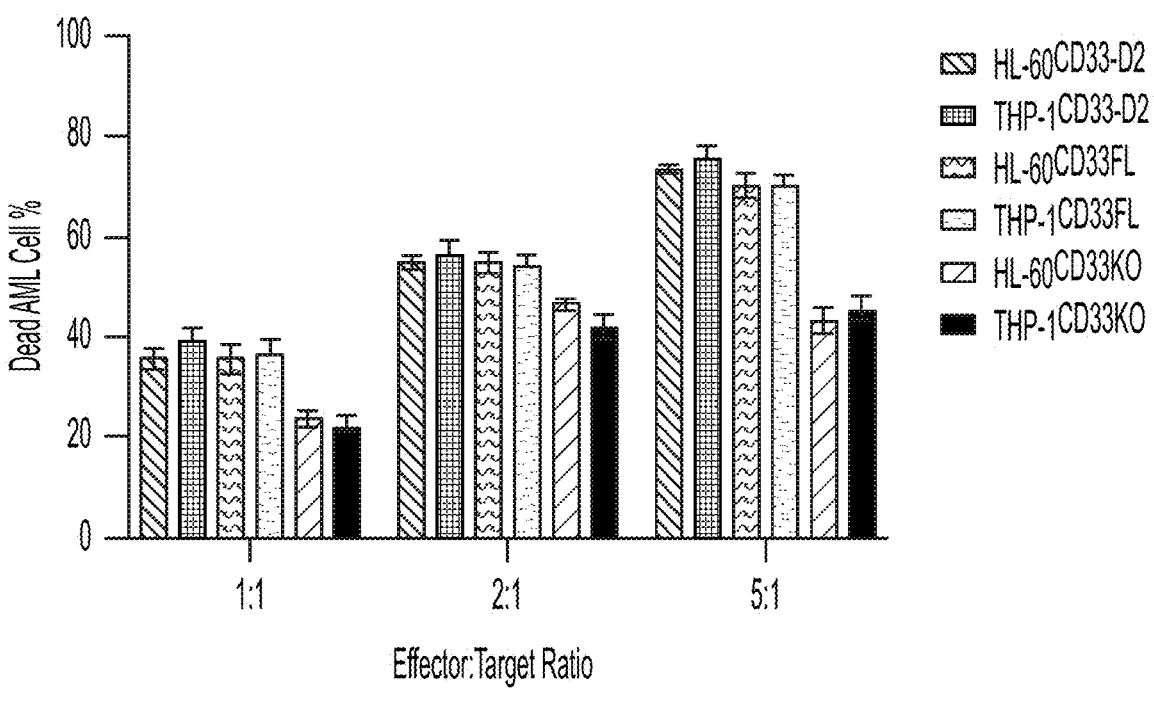
FIG. 25 shows 1×CD33$^{D2}$×CD3 ACE mediates increased T cell killing of CD33$^{D2}$ and CD33$^{FL}$ expressing HL-60 and THP-1 cells in E:T ratio dependent manner after 24 hours.

When assessing the HL-60 and THP-1 groups, it was observed that 1×CD33$^{D2}$×CD3 ACE mediated increased T cell killing of both HL-60 and THP-1 cells in an E:T ratio-dependent manner after 24 hours (FIG. 25).

Figure 26:
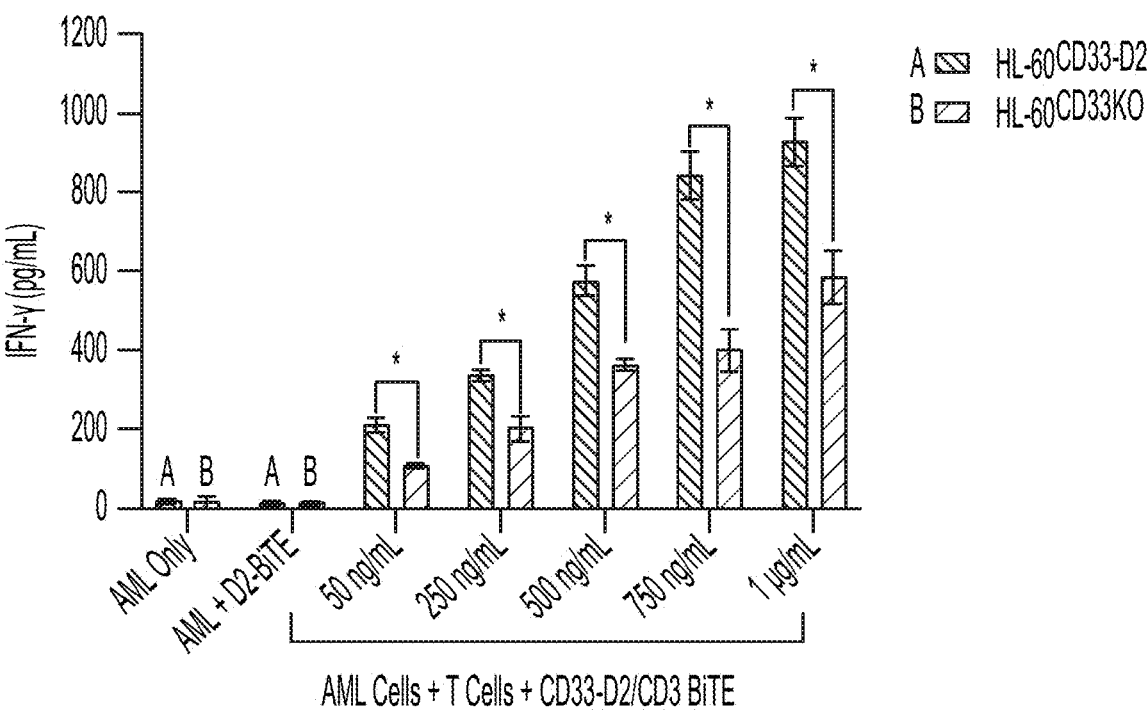
FIG. 26 shows CD33$^{D2}$×CD3 BiTE elicits significantly higher IFN-gamma secretion in co-cultures containing CD33$^{D2}$ expressing HL-60 cells and T cells compared to co-cultures containing CD33$^{KO}$ HL-60 cells and T cells, as measured by an ELISA assay.

A CD33$^{D2}$×CD3 bispecific T cell engager (BiTE) was also produced using the services of Promab Biotechnologies, Inc. It was observed that the BiTE elicits significantly higher IFN-gamma secretion in the cytotoxicity assay (FIG. 26). The assay design was comprised of co-culturing HL-60 cells either expressing CD33$^{D2}$ or no CD33 with T cells expanded from T cells isolated from PBMCs and CD33$^{D2}$×CD3 BiTE for 20 hours at a 10:1 E:T ratio.

SEQUENCES

>CD33 full length (CD33$^{FL}$) amino acid sequence; NCBI Accession
No. NM_001722.4 (SEQ ID NO: 1)
MPLLLLLPLLWAGALAMDPNFWLQVQESVTVQEGLCVLVPCTFFHPIPYYDKNSPVHGYWFREG
AIISRDSPVATNKLDQEVQEETQGRFRLLGDPSRNNCSLSIVDARRRDNGSYFFRMERGSTKYS
YKSPQLSVHVTDLTHRPKILIPGTLEPGHSKNLTCSVSWACEQGTPPIFSWLSAAPTSLGPRTT
HSSVLIITPRPQDHGTNLTCQVKFAGAGVTTERTIQLNVTYVPQNPTTGIFPGDGSGKQETRAG
VVHGAIGGAGVTALLALCLCLIFFIVKTHRRKAARTAVGRNDTHPTTGSASPKHQKKSKLHGPT
ETSSCSGAAPTVEMDEELHYASLNFHGMNPSKDTSTEYSEVRTQ >CD33$^{D2}$ isoform amino acid sequence; NCBI Accession No.
NM_001082618.2 (SEQ ID NO: 2)
MPLLLLLPLLWADLTHRPKILIPGTLEPGHSKNLTCSVSWACEQGTPPIFSWLSAAPTSLGPRT
THSSVLIITPRPQDHGTNLTCQVKFAGAGVTTERTIQLNVTYVPQNPTTGIFPGDGSGKQETRA
GVVHGAIGGAGVTALLALCLCLIFFIVKTHRRKAARTAVGRNDTHPTTGSASPKHQKKSKLHGP
TETSSCSGAAPTVEMDEELHYASLNFHGMNPSKDTSTEYSEVRTQ >CD33$^{D2}$ (HL2541) antigen (SEQ ID NO: 3)
PRPQDHGTNLTCQVKFAGAG >HL2541 Heavy Chain CDR1 Amino Acid (SEQ ID NO: 4)
GYTFTYYG >HL2541 Heavy Chain CDR1 Nucleotide (SEQ ID NO: 5)
GGGTATACCTTCACATACTATGGA >HL2541 Heavy Chain CDR2 Amino Acid (SEQ ID NO: 6)
INTYTGEP >HL2541 Heavy Chain CDR2 Nucleotide (SEQ ID NO: 7)
ATAAACACCTACACTGGAGAGCCA >HL2541 Heavy Chain CDR3 Amino Acid (SEQ ID NO: 8)
ASAYYGSRRAS >HL2541 Heavy Chain CDR3 Nucleotide (SEQ ID NO: 9)
GCCTCCGCTTACTACGGAAGTAGAAGGGCTTCC >HL2541 Light Chain CDR1 Amino Acid (SEQ ID NO: 10)
QSLLDSDGKTY >HL2541 Light Chain CDR1 Nucleotide (SEQ ID NO: 11)
CAGAGCCTCTTAGATAGTGATGGAAAGACATAT >HL2541 Light Chain CDR2 Amino Acid (SEQ ID NO: 12)
LVS >HL2541 Light Chain CDR2 Nucleotide (SEQ ID NO: 13)
CTGGTGTCT >HL2541 Light Chain CDR3 Amino Acid (SEQ ID NO: 14)
WQGTHFPWT >HL2541 Light Chain CDR3 (SEQ ID NO: 15)
TGGCAAGGTACACATTTTCCGTGGACG >HL2541 heavy chain variable domain amino acid sequence
(SEQ ID NO: 16)
MAWVWTLLFLMAAAQSAQVQIQLVQSGPELKKPGETVKISCKASGYTFTYYGMNWVKQAPGKGL
KWMGWINTYTGEPAYADDFKGRFAFSLETSASTAYLQINNLKNEDTATYFCASAYYGSRRASWG
QGTLVTVSAAKTTPPSVYPLAPGSAAQTNSMVTLGCLVKGYFPEPVTVTWNYGALSSSVQAWRN
X >HL2541 light chain variable domain amino acid sequence
(SEQ ID NO: 17)
VHFLKMMSPAQFLFLLVLWIRETNGDVVMTQTPLTLSVTIGQPASISCKSSQSLLDSDGKTYLN
WLLQRPGQSPKRLMYLVSKLDSGVPDRFTGSGSGTDFTLKISRVEAEDLGVYYCWQGTHFPWTF
GGGTKLEIKRADAAPTVSIFPPSSEQLTKLGVI >HL2541 heavy chain nucleotide sequence (SEQ ID NO: 18)
ATGGCTTGGGTGTGGACCTTGCTATTCCTGATGGCAGCTGCCCAAAGTGCCCAAGTACAGATCC
AGTTGGTGCAGTCTGGACCTGAGCTGAAAAAGCCTGGAGAGACAGTCAAGATCTCCTGCAAGGC
TTCTGGGTATACCTTCACATACTATGGAATGAACTGGGTGAAGCAGGCTCCAGGAAAGGGTTTA
AAGTGGATGGGCTGGATAAACACCTACACTGGAGAGCCAGCATATGCTGATGACTTCAAGGGAC
GGTTTGCCTTCTCTTTGGAAACCTCTGCCAGTACTGCCTATTTGCAGATCAACAACCTCAAAAA
TGAGGACACGGCAACATATTTCTGTGCCTCCGCTTACTACGGAAGTAGAAGGGCTTCCTGGGGC
CAAGGGACTCTGGTCACTGTCTCTGCAGCCAAAACGACACCCCCATCGTCTATCCACTGGCCC
CTGGATCTGCTGCCCAAACTAACTCCATGGTGACCCTGGGATGCCTGGTCAAGGGCTATTTCCC
TGAGCCAGTGACAGTGACCTGGAACTAT -continued

---

SEQUENCES

---

>HL2541 light chain nucleotide sequence (SEQ ID NO: 19)
ATGTTCATTTCCTCAAAATGATGAGTCCTGCCCAGTTCCTGTTTCTGTTAGTGCTCTGGATTCG
GGAAACCAACGGTGATGTTGTGATGACCCAGACTCCACTCACTTTGTCGGTTACCATTGGACAA
CCAGCCTCCATCTCTTGCAAGTCAAGTCAGAGCCTCTTAGATAGTGATGGAAAGACATATTTGA
ATTGGTTGTTACAGAGGCCAGGCCAGTCTCCAAAGCGCCTAATGTATCTGGTGTCTAAACTGGA
CTCTGGAGTACCTGACAGGTTCACTGGCAGTGGATCAGGGACAGATTTCACACTGAAAATCAGC
AGAGTGGAGGCTGAGGATTTGGGAGTTTATTATTGCTGGCAAGGTACACATTTTCCGTGGACGT
TCGGTGGAGGCACCAAGCTGGAGATCAAACGGGCTGATGCTGCACCAACTGTATCCATCTTCCC
ACCATCCAGTGAGCAGTTAACAAAGCTTGGCGTAATC >CD33$^{D2}$ Nucleic Acid Sequence NM_001082618.2 (SEQ ID NO: 20)
ATGCCGCTGCTGCTACTGCTGCCCCTGCTGTGGGCAGACTTGACCCACAGGCCCAAAATCCTCA
TCCCTGGCACTCTAGAACCCGGCCACTCCAAAAACCTGACCTGCTCTGTGTCCTGGGCCTGTGA
GCAGGGAACACCCCGATCTTCTCCTGGTTGTCAGCTGCCCCCACCTCCCTGGGCCCCAGGACT
ACTCACTCCTCGGTGCTCATAATCACCCCACGGCCCCAGGACCCACGGCACCAACCTGACCTGTC
AGGIGAAGTTCGCTGGAGCTGGTGTGACTACGGAGAGAACCATCCAGCTCAACGTCACCTATGT
TCCACAGAACCCAACAACTGGTATCTTTCCAGGAGATGGCTCAGGGAAACAAGAGACCAGAGCA
GGAGTGGTTCATGGGGCCATTGGAGGAGCTGGTGTTACAGCCCTGCTCGCTCTTTGTCTCTGCC
TCATCTTCTTCATAGTGAAGACCCACAGGAGGAAAGCAGCCAGGACAGCAGTGGGCAGGAATGA
CACCCACCCTACCACAGGGTCAGCCTCCCCGAAACACCAGAAGAAGTCCAAGTTACATGGCCCC
ACTGAAACCTCAAGCTGTTCAGGIGCCGCCCCTACTGTGGAGATGGATGAGGAGCTGCATTATG
CTTCCCTCAACTTTCATGGGATGAATCCTTCCAAGGACACCTCCACCGAATACTCAGAGGTCAG
GACCCAGTGA >anti-CD33 Amino Acid Sequence (D2 HL-2541)
(used in CD33$^{D2}$ × CD3 ACE and BiTE) (SEQ ID NO: 21)
DVVMTQTPLTLSVTIGQPASISCKSSQSLLDSDGKTYLNWLLQRPGQSPKRLMYLVSKLDSGVP
DRFTGSGSGTDFTLKISRVEAEDLGVYYCWQGTHFPWTFGGGTKLEIKGGGGSGGGGSGGGGSQ
IQLVQSGPELKKPGETVKISCKASGYTFTYYGMNWVKQAPGKGLKWMGWINTYTGEPAYADDFK
GRFAFSLETSASTAYLQINNLKNEDTATYFCASAYYGSRRASWGQGTLVTVS >anti-CD3 Amino Acid Sequence (used in CD33$^{D2}$ × CD3 ACE and BiTE)
(SEQ ID NO: 22)
GGGGSDIKLQQSGAELARPGASVKMSCKTSGYTFTRYTMHWVKQRPGQGLEWIGYINPSRGYTN
YNQKFKDKATLTTDKSSSTAYMQLSSLTSEDSAVYYCARYYDDHYCLDYWGQGTTLTVSSVEGG
SGGSGGSGGSGGVDDIQLTQSPAIMSASPGEKVTMTCRASSSVSYMNWYQQKSGTSPKRWIYDT
SKVASGVPYRFSGSGSGTSYSLTISSMEAEDAATYYCQQWSSNPLTFGAGTKLELK

---

SEQUENCE LISTING

---

<160> NUMBER OF SEQ ID NOS: 22

<210> SEQ ID NO 1
<211> LENGTH: 364
<212> TYPE: PRT
<213> ORGANISM: Homo sapiens

<400> SEQUENCE: 1

Met Pro Leu Leu Leu Leu Leu Pro Leu Leu Trp Ala Gly Ala Leu Ala
1                5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

-continued

```
Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
            195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
            275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
            355                 360
```

```
<210> SEQ ID NO 2
<211> LENGTH: 237
<212> TYPE: PRT
<213> ORGANISM: Homo sapiens

<400> SEQUENCE: 2
```

```
Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
            115                 120                 125

Gly Val Val His Gly Ala Ile Gly Gly Ala Gly Val Thr Ala Leu Leu
    130                 135                 140
```

```
Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235

<210> SEQ ID NO 3
<211> LENGTH: 20
<212> TYPE: PRT
<213> ORGANISM: Artificial Sequence
<220> FEATURE:
<223> OTHER INFORMATION: Synthetic

<400> SEQUENCE: 3

Pro Arg Pro Gln Asp His Gly Thr Asn Leu Thr Cys Gln Val Lys Phe
1               5                   10                  15

Ala Gly Ala Gly
            20

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Tyr Thr Phe Thr Tyr Tyr Gly
1               5

<210> SEQ ID NO 5
<211> LENGTH: 24
<212> TYPE: PRT
<213> ORGANISM: Artificial Sequence
<220> FEATURE:
<223> OTHER INFORMATION: Synthetic

<400> SEQUENCE: 5

Gly Gly Gly Thr Ala Thr Ala Cys Cys Thr Thr Cys Ala Cys Ala Thr
1               5                   10                  15

Ala Cys Thr Ala Thr Gly Gly Ala
            20

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Asn Thr Tyr Thr Gly Glu Pro
1               5

<210> SEQ ID NO 7
```

-continued

```
<211> LENGTH: 24
<212> TYPE: DNA
<213> ORGANISM: Artificial Sequence
<220> FEATURE:
<223> OTHER INFORMATION: Synthetic

<400> SEQUENCE: 7
ataaacacct acactggaga gcca                                              24

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Ala Ser Ala Tyr Tyr Gly Ser Arg Arg Ala Ser
1               5                   10

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
gcctccgctt actacggaag tagaagggct tcc                                    33

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Gln Ser Leu Leu Asp Ser Asp Gly Lys Thr Tyr
1               5                   10

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
cagagcctct tagatagtga tggaaagaca tat                                    33

<210> SEQ ID NO 12
<211> LENGTH: 3
<212> TYPE: PRT
<213> ORGANISM: Artificial Sequence
<220> FEATURE:
<223> OTHER INFORMATION: Synthetic

<400> SEQUENCE: 12

Leu Val Ser
1

<210> SEQ ID NO 13
<211> LENGTH: 9
<212> TYPE: DNA
<213> ORGANISM: Artificial Sequence
<220> FEATURE:
```

<223> OTHER INFORMATION: Synthetic

<400> SEQUENCE: 13 ctggtgtct                                                                                        9

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Trp Gln Gly Thr His Phe Pro Trp Thr
1               5

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
tggcaaggta cacattttcc gtggacg                                                                     27

<210> SEQ ID NO 16
<211> LENGTH: 193
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (193)..(193)
<223> OTHER INFORMATION: Xaa can be any naturally occurring amino acid

<400> SEQUENCE: 16

Met Ala Trp Val Trp Thr Leu Leu Phe Leu Met Ala Ala Ala Gln Ser
1               5                   10                  15

Ala Gln Val Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Tyr Tyr Gly Met Asn Trp Val Lys Gln Ala Pro Gly Lys Gly Leu
        50                  55                  60

Lys Trp Met Gly Trp Ile Asn Thr Tyr Thr Gly Glu Pro Ala Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Ser Ala Tyr Tyr Gly Ser Arg Arg Ala Ser Trp Gly
            115                 120                 125

Gln Gly Thr Leu Val Thr Val Ser Ala Ala Lys Thr Thr Pro Pro Ser
        130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Tyr Gly Ala Leu Ser Ser Ser Val Gln Ala Trp Arg Asn

-continued

```
            180             185             190

Xaa

<210> SEQ ID NO 17
<211> LENGTH: 161
<212> TYPE: PRT
<213> ORGANISM: Artificial Sequence
<220> FEATURE:
<223> OTHER INFORMATION: Synthetic

<400> SEQUENCE: 17

Val His Phe Leu Lys Met Met Ser Pro Ala Gln Phe Leu Phe Leu Leu
1               5                   10                  15

Val Leu Trp Ile Arg Glu Thr Asn Gly Asp Val Val Met Thr Gln Thr
            20                  25                  30

Pro Leu Thr Leu Ser Val Thr Ile Gly Gln Pro Ala Ser Ile Ser Cys
        35                  40                  45

Lys Ser Ser Gln Ser Leu Leu Asp Ser Asp Gly Lys Thr Tyr Leu Asn
    50                  55                  60

Trp Leu Leu Gln Arg Pro Gly Gln Ser Pro Lys Arg Leu Met Tyr Leu
65                  70                  75                  80

Val Ser Lys Leu Asp Ser Gly Val Pro Asp Arg Phe Thr Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Trp Gln Gly Thr His Phe Pro Trp Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Ser Glu Gln Leu Thr Lys Leu Gly Val
145                 150                 155                 160

Ile

<210> SEQ ID NO 18
<211> LENGTH: 540
<212> TYPE: DNA
<213> ORGANISM: Artificial Sequence
<220> FEATURE:
<223> OTHER INFORMATION: Synthetic

<400> SEQUENCE: 18
atggcttggg tgtggacctt gctattcctg atggcagctg cccaaagtgc ccaagtacag      60
atccagttgg tgcagtctgg acctgagctg aaaaagcctg gagagacagt caagatctcc     120
tgcaaggctt ctgggtatac cttcacatac tatggaatga actgggtgaa gcaggctcca     180
ggaaagggtt taaagtggat gggctggata aacacctaca ctggagagcc agcatatgct     240
gatgacttca aggacggtt tgccttctct ttggaacct ctgccagtac tgcctatttg     300
cagatcaaca acctcaaaaa tgaggacacg gcaacatatt tctgtgcctc cgcttactac     360
ggaagtagaa gggcttcctg gggccaaggg actctggtca ctgtctctgc agccaaaacg     420
acacccccat ctgtctatcc actgcccct ggatctgctg cccaaactaa ctccatggtg     480
accctgggat gcctggtcaa gggctatttc cctgagccag tgacagtgac ctggaactat     540

<210> SEQ ID NO 19
<211> LENGTH: 485
<212> TYPE: DNA
<213> ORGANISM: Artificial Sequence
```

-continued

```
<220> FEATURE:
<223> OTHER INFORMATION: Synthetic

<400> SEQUENCE: 19
atgttcattt cctcaaaatg atgagtcctg cccagttcct gtttctgtta gtgctctgga        60
ttcgggaaac caacggtgat gttgtgatga cccagactcc actcactttg tcggttacca       120
ttggacaacc agcctccatc tcttgcaagt caagtcagag cctcttagat agtgatggaa       180
agacatattt gaattggttg ttacagaggc caggccagtc tccaaagcgc ctaatgtatc       240
tggtgtctaa actggactct ggagtacctg acaggttcac tggcagtgga tcagggacag       300
atttcacact gaaaatcagc agagtggagg ctgaggattt gggagtttat tattgctggc       360
aaggtacaca ttttccgtgg acgttcggtg gaggcaccaa gctggagatc aaacgggctg       420
atgctgcacc aactgtatcc atcttcccac catccagtga gcagttaaca aagcttggcg       480
taatc                                                                    485

<210> SEQ ID NO 20
<211> LENGTH: 714
<212> TYPE: DNA
<213> ORGANISM: Artificial Sequence
<220> FEATURE:
<223> OTHER INFORMATION: Synthetic

<400> SEQUENCE: 20
atgccgctgc tgctactgct gcccctgctg tgggcagact tgacccacag gcccaaaatc        60
ctcatccctg gcactctaga acccggccac tccaaaaacc tgacctgctc tgtgtcctgg       120
gcctgtgagc agggaacacc cccgatcttc tcctggttgt cagctgcccc cacctccctg       180
ggccccagga ctactcactc ctcggtgctc ataatcaccc cacggcccca ggaccacggc       240
accaacctga cctgtcaggt gaagttcgct ggagctggtg tgactacgga gagaaccatc       300
cagctcaacg tcacctatgt tccacagaac ccaacaactg gtatctttcc aggagatggc       360
tcagggaaac aagagaccag agcaggagtg gttcatgggg ccattggagg agctggtgtt       420
acagccctgc tcgctctttg tctctgcctc atcttcttca gtgtgaagac ccacaggagg       480
aaagcagcca ggacagcagt gggcaggaat gacacccacc ctaccacagg gtcagcctcc       540
ccgaaacacc agaagaagtc caagttacat ggccccactg aaacctcaag ctgttcaggt       600 gccgcccta ctgtggagat ggatgaggag ctgcattatg cttccctcaa ctttcatggg       660
atgaatcctt ccaaggacac ctccaccgaa tactcagagg tcaggaccca gtga            714

<210> SEQ ID NO 21
<211> LENGTH: 244
<212> TYPE: PRT
<213> ORGANISM: Artificial Sequence
<220> FEATURE:
<223> OTHER INFORMATION: Synthetic

<400> SEQUENCE: 21

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Met Tyr Leu Val Ser Lys Leu Asp Ser Gly Val Pro
    50                  55                  60
```

```
Asp Arg Phe Thr Gly Ser Gly Ser Gly Thr Asp Phe Thr Leu Lys Ile
65              70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Gly Gly Gly Gly Ser Gly Gly Gly Ser Gly Gly Gly Ser Gln
            115                 120                 125

Ile Gln Leu Val Gln Ser Gly Pro Glu Leu Lys Lys Pro Gly Glu Thr
    130                 135                 140

Val Lys Ile Ser Cys Lys Ala Ser Gly Tyr Thr Phe Thr Tyr Tyr Gly
145                 150                 155                 160

Met Asn Trp Val Lys Gln Ala Pro Gly Lys Gly Leu Lys Trp Met Gly
                165                 170                 175

Trp Ile Asn Thr Tyr Thr Gly Glu Pro Ala Tyr Ala Asp Asp Phe Lys
                180                 185                 190

Gly Arg Phe Ala Phe Ser Leu Glu Thr Ser Ala Ser Thr Ala Tyr Leu
            195                 200                 205

Gln Ile Asn Asn Leu Lys Asn Glu Asp Thr Ala Thr Tyr Phe Cys Ala
    210                 215                 220

Ser Ala Tyr Tyr Gly Ser Arg Arg Ala Ser Trp Gly Gln Gly Thr Leu
225                 230                 235                 240

Val Thr Val Ser

<210> SEQ ID NO 22
<211> LENGTH: 248
<212> TYPE: PRT
<213> ORGANISM: Artificial Sequence
<220> FEATURE:
<223> OTHER INFORMATION: Synthetic

<400> SEQUENCE: 22

Gly Gly Gly Gly Ser Asp Ile Lys Leu Gln Gln Ser Gly Ala Glu Leu
1               5                   10                  15

Ala Arg Pro Gly Ala Ser Val Lys Met Ser Cys Lys Thr Ser Gly Tyr
                20                  25                  30

Thr Phe Thr Arg Tyr Thr Met His Trp Val Lys Gln Arg Pro Gly Gln
            35                  40                  45

Gly Leu Glu Trp Ile Gly Tyr Ile Asn Pro Ser Arg Gly Tyr Thr Asn
    50                  55                  60

Tyr Asn Gln Lys Phe Lys Asp Lys Ala Thr Leu Thr Thr Asp Lys Ser
65              70                  75                  80

Ser Ser Thr Ala Tyr Met Gln Leu Ser Ser Leu Thr Ser Glu Asp Ser
                85                  90                  95

Ala Val Tyr Tyr Cys Ala Arg Tyr Tyr Asp Asp His Tyr Cys Leu Asp
                100                 105                 110

Tyr Trp Gly Gln Gly Thr Thr Leu Thr Val Ser Ser Val Glu Gly Gly
            115                 120                 125

Ser Gly Gly Ser Gly Gly Ser Gly Gly Ser Gly Gly Val Asp Asp Ile
    130                 135                 140

Gln Leu Thr Gln Ser Pro Ala Ile Met Ser Ala Ser Pro Gly Glu Lys
145                 150                 155                 160

Val Thr Met Thr Cys Arg Ala Ser Ser Ser Val Ser Tyr Met Asn Trp
                165                 170                 175

Tyr Gln Gln Lys Ser Gly Thr Ser Pro Lys Arg Trp Ile Tyr Asp Thr
```

-continued

|  | 180 |  |  |  |  | 185 |  |  |  |  | 190 |  |  |  |
|---|---|---|---|---|---|---|---|---|---|---|---|---|---|---|
| Ser | Lys | Val | Ala | Ser | Gly | Val | Pro | Tyr | Arg | Phe | Ser | Gly | Ser | Gly | Ser |
|  | 195 |  |  |  |  | 200 |  |  |  |  | 205 |  |  |  |

| Gly | Thr | Ser | Tyr | Ser | Leu | Thr | Ile | Ser | Ser | Met | Glu | Ala | Glu | Asp | Ala |
|---|---|---|---|---|---|---|---|---|---|---|---|---|---|---|---|
|  | 210 |  |  |  |  | 215 |  |  |  |  | 220 |  |  |  |

| Ala | Thr | Tyr | Tyr | Cys | Gln | Gln | Trp | Ser | Ser | Asn | Pro | Leu | Thr | Phe | Gly |
|---|---|---|---|---|---|---|---|---|---|---|---|---|---|---|---|
| 225 |  |  |  |  | 230 |  |  |  |  | 235 |  |  |  |  | 240 |

| Ala | Gly | Thr | Lys | Leu | Glu | Leu | Lys |
|---|---|---|---|---|---|---|---|
|  |  |  | 245 |  |  |  |  |

What is claimed is:

1. An antibody or antigen binding fragment that specifically binds to a CD33 protein, wherein the antibody or antigen binding fragment comprises a heavy chain variable region having the sequence set forth as: SEQ ID NO: 16 and a light chain variable region comprising the sequence set forth as SEQ ID NO: 17.

2. The antibody of claim 1, wherein the antibody specifically binds an epitope consisting of the amino acid sequence of SEQ ID NO: 3.

3. The antibody of claim 1, wherein the CD33 protein is a comprising the amino acid sequence of SEQ ID NO: 2.

4. The antibody of claim 1, wherein the antibody or antigen binding fragment is a chimeric antibody.

5. An antibody, or antigen binding fragment, that specifically binds to cell-surface expressing CD33 antigen and that comprises six complementarity determining regions (CDRs): of a heavy chain CDRH1, CDRH2, CDRH3, and a light chain CDRL1, CDRL2, and CDRL3, wherein CDRH1 comprises a sequence as set forth in SEQ ID NO: 4, CDRH2 comprises a sequence as set forth in SEQ ID NO: 6, CDRH3 comprises a sequence as set forth in SEQ ID NO: 8, CDRL1 comprises a sequence as set forth in SEQ ID NO: 10, CDRL2 comprises a sequence as set forth in SEQ ID NO: 12, and CDRL3 comprises a sequence as set forth in SEQ ID NO: 14.

6. The antibody, or antigen binding fragment, of claim 5, wherein the antibody or antigen binding fragment, is a monoclonal antibody, a humanized antibody, a diabody, a chimeric antibody, a Fab fragment, a F(ab')2 fragment, affibody, or an Fv fragment.

* * * * *